(12) United States Patent
Galley et al.

(10) Patent No.: US 9,840,501 B2
(45) Date of Patent: Dec. 12, 2017

(54) MORPHOLIN-PYRIDINE DERIVATIVES

(71) Applicant: Hoffmann-La Roche Inc., Little Falls, NJ (US)

(72) Inventors: Guido Galley, Rheinfelden (DE); Philippe Pflieger, Schwoben (FR); Roger Norcross, Olsberg (CH); Giuseppe Cecere, Basel (CH); Hong Shen, Shanghai (CN); Yimin Hu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/334,707

(22) Filed: Oct. 26, 2016

(65) Prior Publication Data
US 2017/0044145 A1    Feb. 16, 2017

Related U.S. Application Data

(63) Continuation of application No. PCT/EP2015/059002, filed on Apr. 27, 2015.

(30) Foreign Application Priority Data

Apr. 30, 2014  (CN) ................ PCT/CN2014/076623

(51) Int. Cl.
C07D 413/04 (2006.01)
C07D 413/12 (2006.01)
C07D 413/14 (2006.01)

(52) U.S. Cl.
CPC ......... C07D 413/04 (2013.01); C07D 413/12 (2013.01); C07D 413/14 (2013.01)

(58) Field of Classification Search
CPC ... C07D 413/04; C07D 413/12; C07D 413/14
See application file for complete search history.

(56) References Cited

U.S. PATENT DOCUMENTS

2011/0152245 A1   6/2011   Zbinden et al.
2012/0245172 A1   9/2012   Galley et al.

FOREIGN PATENT DOCUMENTS

| CN | 102686563 A | 9/2012 |
| CN | 103443074 A | 12/2013 |
| WO | 2008/074679 A2 | 6/2008 |
| WO | 2011/076678 A1 | 6/2011 |
| WO | 2012/016879 A1 | 2/2012 |
| WO | 2012/126922 A1 | 9/2012 |
| WO | 2012/168260 | 12/2012 |

OTHER PUBLICATIONS

ISR for PCT/EP2015/059002 dated Jun. 2015.

*Primary Examiner* — Rebecca L Anderson

(57) ABSTRACT

The present invention relates to compounds of formula of formula I wherein X, R, L, Ar, $R^1$ and n are as described herein, compositions containing compounds of formula I, methods of manufacture of compounds of formula I and methods of treating psychiatric disorders with compounds of formula I.

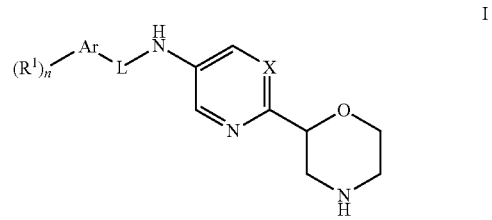

I

12 Claims, No Drawings

MORPHOLIN-PYRIDINE DERIVATIVES

CROSS REFERENCE TO RELATED APPLICATIONS

This application is a continuation of International Application No. PCT/EP2015/059002 having an international filing date of Apr. 27, 2015 and which claims benefit under 35 U.S.C. §119 to International Application PCT/CN2014/076623 filed Apr. 30, 2014. The entire contents of both are incorporated herein by reference.

FIELD OF THE INVENTION

The present invention relates to novel compounds of formula I, wherein $R^1$, Ar, L, X and n are as described herein, having pharmaceutical activity, their manufacture, pharmaceutical compositions containing them and their potential use as medicaments.

BACKGROUND OF THE INVENTION

Aberrant activity of Trace Amine Associated Receptors (TAARs), especially for TAAR1 is associated with psychiatric conditions such as depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well-known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison, and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the etiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

BRIEF SUMMARY OF THE INVENTION

In one aspect, the present invention relates to compounds of formula

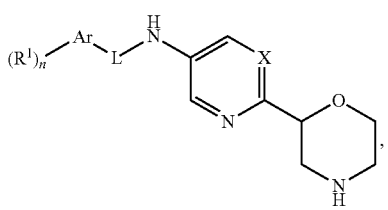

I wherein
X is CR;
R is hydrogen, halogen or lower alkyl;
L is a bond, —C(O)— or —C(O)NH—;
Ar is phenyl or a five or six membered heteroaryl group, containing one or two N atoms;
$R^1$ is halogen, lower alkyl, lower alkyl substituted by halogen, lower alkoxy, lower alkoxy substituted by halogen or is cycloalkyl;
n is 0, 1, 2 or 3;
or, a pharmaceutically suitable acid addition salt thereof, a racemic mixture, an enantiomer or mixture thereof.

In another embodiment, the present inventions provide for pharmaceutical compositions comprising compounds of Formula I.

In another embodiment, the present invention provides for methods of treating disease associated with trace amine associated receptors.

DETAILED DESCRIPTION OF THE INVENTION

There is a broad interest to increase the knowledge about trace amine associated receptors. It has now been found that the compounds of formulas I have a good affinity to the trace amine associated receptors (TAARs), especially for TAAR1.

Objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety, attention deficit hyperactivity disorder (ADHD) and diabetes.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

The term "halogen" denotes chlorine, iodine, fluorine and bromine. The preferred halogen groups are fluorine or chlorine.

As used herein, the term "lower alkyl substituted by halogen" denotes a saturated straight- or branched-chain group containing from 1 to 7 carbon atoms as defined for the term "lower alkyl", wherein at least one hydrogen atom is replaced by a halogen atom. A preferred halogen atom is fluoro. Examples of such groups are $CF_3$, $CHF_2$, $CH_2F$, $CH_2CF_3$ or $CH_2CHF_2$.

As used herein, the term "lower alkoxy substituted by halogen" denotes an alkoxy group as defined above, and wherein at least one hydrogen atom is replaced by halogen.

The term "cycloalkyl" denotes a saturated carbon ring, containing from 3 to 6 carbon atoms, for example cyclopropyl, cyclobutyl, cyclopentyl or cyclohexyl.

The term "five or six membered heteroaryl group, containing one or two N atoms" denotes a cyclic aromatic 5 or six membered ring, wherein at least one carbon atom is replaced by a nitrogen atom, for example the groups pyridinyl, pyrimidinyl or pyrazolyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

It will be appreciated by the skilled artisan that compounds of formula I may contain a chiral center and therefore exist in two stereoisomeric forms. The racemates of these isomers, the individual isomers and mixtures enriched in one enantiomer are within the scope of the present invention. The present invention includes all the individual stereoisomers (e.g. enantiomers), racemic mixtures or partially resolved mixtures of the compounds of formulae I.

One embodiment of the present invention is compounds of formula I wherein X is CR and the remaining variables are as described in the brief summary of the invention.

One embodiment of the present invention is compounds of formula I wherein X is N and the remaining variables are as described in the brief summary of the invention.

One embodiment of the invention are compounds of formula I, in which "L" is a bond, for example the following compounds, (RS)—N-(4-Chlorophenyl)-6-morpholin-2-yl-pyridin-3-amine (RS)—N-(4-Bromophenyl)-6-morpholin-2-yl-pyridin-3-amine (RS)—N-(4-Ethoxyphenyl)-6-morpholin-2-yl-pyridin-3-amine (RS)—N-(3-Chlorophenyl)-6-morpholin-2-yl-pyridin-3-amine
(RS)—N-(4-Fluorophenyl)-6-morpholin-2-yl-pyridin-3-amine
(RS)-6-Morpholin-2-yl-N-[4-(trifluoromethyl)phenyl]pyridin-3-amine
(RS)—N-(6-Morpholin-2-yl-3-pyridyl)-2-(trifluoromethyl)pyrimidin-4-amine
N-(4-Chlorophenyl)-6-[(2S)-morpholin-2-yl]pyridin-3-amine
6-[(2S)-Morpholin-2-yl]-N-[4-(trifluoromethyl)phenyl]pyridin-3-amine
N-(5-Chloro-2-pyridyl)-6-[(2S)-morpholin-2-yl]pyridin-3-amine
N-(5-Bromo-2-pyridyl)-6-[(2S)-morpholin-2-yl]pyridin-3-amine
6-[(2S)-Morpholin-2-yl]-N-[6-(trifluoromethyl)-3-pyridyl]pyridin-3-amine
6-[(2S)-Morpholin-2-yl]-N-[4-(trifluoromethyl)-2-pyridyl]pyridin-3-amine
N-(4-Chlorophenyl)-6-[(2R)-morpholin-2-yl]pyridin-3-amine
6-[(2R)-Morpholin-2-yl]-N-[4-(trifluoromethyl)phenyl]pyridin-3-amine
N-(5-Chloro-2-pyridyl)-6-[(2R)-morpholin-2-yl]pyridin-3-amine
6-[(2R)-Morpholin-2-yl]-N-[6-(trifluoromethyl)-3-pyridyl]pyridin-3-amine
6-[(2R)-Morpholin-2-yl]-N-[4-(trifluoromethyl)-2-pyridyl]pyridin-3-amine
N-[6-[(2S)-Morpholin-2-yl]-3-pyridyl]-5-(trifluoromethyl)pyridin-2-amine
N-[6-[(2S)-Morpholin-2-yl]-3-pyridyl]-6-(trifluoromethyl)pyridin-2-amine
N-(5-Bromo-2-pyridyl)-6-[(2R)-morpholin-2-yl]pyridin-3-amine
N-[6-[(2R)-Morpholin-2-yl]-3-pyridyl]-5-(trifluoromethyl)pyridin-2-amine
N-[6-[(2R)-Morpholin-2-yl]-3-pyridyl]-6-(trifluoromethyl)pyridin-2-amine
(RS)—N-(4-Chlorophenyl)-2-morpholin-2-yl-pyrimidin-5-amine
(RS)-2-Morpholin-2-yl-N-[4-(trifluoromethyl)phenyl]pyrimidin-5-amine
(RS)-5-Chloro-N-(5-chloro-2-pyridyl)-6-morpholin-2-yl-pyridin-3-amine
(RS)-5-Chloro-6-morpholin-2-yl-N-[5-(trifluoromethyl)-2-pyridyl]pyridin-3-amine
(RS)-5-Methyl-6-morpholin-2-yl-N-[5-(trifluoromethyl)-2-pyridyl]pyridin-3-amine
(RS)—N-(5-Chloro-2-pyridyl)-5-fluoro-6-morpholin-2-yl-pyridin-3-amine or
(RS)-5-Fluoro-6-morpholin-2-yl-N-[5-(trifluoromethyl)-2-pyridyl]pyridin-3-amine.

One further embodiment of the invention are compounds of formula I, in which "L" is —C(O)—, for example the following compounds
(RS)-4-Chloro-N-(6-morpholin-2-yl-3-pyridyl)benzamide
(RS)-3-Chloro-N-(6-morpholin-2-yl-3-pyridyl)benzamide
(RS)-4-Ethoxy-N-(6-morpholin-2-yl-3-pyridyl)benzamide
(RS)-4-Fluoro-N-(6-morpholin-2-yl-3-pyridyl)benzamide
(RS)-4-Chloro-N-(6-morpholin-2-yl-3-pyridyl)-3-propyl-1H-pyrazole-5-carboxamide
(RS)—N-(6-Morpholin-2-yl-3-pyridyl)-2-(trifluoromethyl)pyridine-4-carboxamide
4-Chloro-N-[6-[(2S)-morpholin-2-yl]-3-pyridyl]benzamide
3-Chloro-N-[6-[(2S)-morpholin-2-yl]-3-pyridyl]benzamide
N-[6-[(2S)-Morpholin-2-yl]-3-pyridyl]-4-(trifluoromethyl)benzamide
N-[6-[(2S)-Morpholin-2-yl]-3-pyridyl]-2-(trifluoromethyl)pyridine-4-carboxamide
N-[6-[(2S)-Morpholin-2-yl]-3-pyridyl]-3-(trifluoromethyl)benzamide
N-[6-[(2S)-Morpholin-2-yl]-3-pyridyl]-6-(2,2,2-trifluoroethoxy)pyridine-3-carboxamide
2-Ethyl-N-[6-[(2S)-morpholin-2-yl]-3-pyridyl]pyrimidine-5-carboxamide
3-Isopropyl-N-[6-[(2S)-morpholin-2-yl]-3-pyridyl]-1H-pyrazole-5-carboxamide
4-Chloro-N-[6-[(2S)-morpholin-2-yl]-3-pyridyl]-3-propyl-1H-pyrazole-5-carboxamide
4-Chloro-3-cyclopropyl-N-[6-[(2S)-morpholin-2-yl]-3-pyridyl]-1H-pyrazole-5-carboxamide
4-Chloro-N-[6-[(2S)-morpholin-2-yl]-3-pyridyl]-3-(trifluoromethyl)-1H-pyrazole-5-carboxamide
4-Chloro-3-methyl-N-[6-[(2S)-morpholin-2-yl]-3-pyridyl]-1H-pyrazole-5-carboxamide
4-Methyl-N-[6-[(2S)-morpholin-2-yl]-3-pyridyl]-1H-pyrazole-5-carboxamide
4-Chloro-1-methyl-N-[6-[(2S)-morpholin-2-yl]-3-pyridyl]-5-propyl-pyrazole-3-carboxamide
4-Chloro-1-methyl-N-[6-[(2R)-morpholin-2-yl]-3-pyridyl]-5-propyl-pyrazole-3-carboxamide
4-Chloro-N-[6-[(2R)-morpholin-2-yl]-3-pyridyl]benzamide
3-Chloro-N-[6-[(2R)-morpholin-2-yl]-3-pyridyl]benzamide
N-[6-[(2R)-Morpholin-2-yl]-3-pyridyl]-4-(trifluoromethyl)benzamide
N-[6-[(2R)-Morpholin-2-yl]-3-pyridyl]-2-(trifluoromethyl)pyridine-4-carboxamide
N-[6-[(2R)-Morpholin-2-yl]-3-pyridyl]-3-(trifluoromethyl)benzamide
N-[6-[(2R)-Morpholin-2-yl]-3-pyridyl]-6-(2,2,2-trifluoroethoxy)pyridine-3-carboxamide
2-Ethyl-N-[6-[(2R)-morpholin-2-yl]-3-pyridyl]pyrimidine-5-carboxamide
3-Isopropyl-N-[6-[(2R)-morpholin-2-yl]-3-pyridyl]-1H-pyrazole-5-carboxamide
4-Chloro-N-[6-[(2R)-morpholin-2-yl]-3-pyridyl]-3-propyl-1H-pyrazole-5-carboxamide
4-Chloro-3-cyclopropyl-N-[6-[(2R)-morpholin-2-yl]-3-pyridyl]-1H-pyrazole-5-carboxamide
4-Chloro-N-[6-[(2R)-morpholin-2-yl]-3-pyridyl]-3-(trifluoromethyl)-1H-pyrazole-5-carboxamide
4-Chloro-3-methyl-N-[6-[(2R)-morpholin-2-yl]-3-pyridyl]-1H-pyrazole-5-carboxamide
4-Methyl-N-[6-[(2R)-morpholin-2-yl]-3-pyridyl]-1H-pyrazole-5-carboxamide
(R)-3-Ethyl-4-methyl-N-(6-(morpholin-2-yl)pyridin-3-yl)-1H-pyrazole-5-carboxamide
(S)-3-Ethyl-4-methyl-N-(6-(morpholin-2-yl)pyridin-3-yl)-1H-pyrazole-5-carboxamide
(R)-6-Methyl-N-(6-(morpholin-2-yl)pyridin-3-yl)-2-(trifluoromethyl)pyrimidine-4-carboxamide
(S)-6-Methyl-N-(6-(morpholin-2-yl)pyridin-3-yl)-2-(trifluoromethyl)pyrimidine-4-carboxamide
(RS)-4-Chloro-N-(2-morpholin-2-ylpyrimidin-5-yl)benzamide
(RS)-4-Chloro-3-ethoxy-N-(6-morpholin-2-yl-3-pyridyl)-1H-pyrazole-5-carboxamide
(RS)-4-Chloro-N-(6-morpholin-2-yl-3-pyridyl)-3-(2,2,2-trifluoroethoxy)-1H-pyrazole-5-carboxamide
4-Chloro-3-ethyl-N-[6-[(2S)-morpholin-2-yl]-3-pyridyl]-1H-pyrazole-5-carboxamide 3-Ethyl-4-fluoro-N-[6-[(2S)-morpholin-2-yl]-3-pyridyl]-1H-pyrazole-5-carboxamide
4-Bromo-3-ethyl-N-[6-[(2S)-morpholin-2-yl]-3-pyridyl]-1H-pyrazole-5-carboxamide
4-Fluoro-N-[6-[(2S)-morpholin-2-yl]-3-pyridyl]-3-propyl-1H-pyrazole-5-carboxamide
3-Cyclopropyl-4-fluoro-N-[6-[(2S)-morpholin-2-yl]-3-pyridyl]-1H-pyrazole-5-carboxamide
4-Bromo-3-cyclopropyl-N-[6-[(2S)-morpholin-2-yl]-3-pyridyl]-1H-pyrazole-5-carboxamide
4-Chloro-3-ethyl-N-[6-[(2R)-morpholin-2-yl]-3-pyridyl]-1H-pyrazole-5-carboxamide
3-Ethyl-4-fluoro-N-[6-[(2R)-morpholin-2-yl]-3-pyridyl]-1H-pyrazole-5-carboxamide
4-Bromo-3-ethyl-N-[6-[(2R)-morpholin-2-yl]-3-pyridyl]-1H-pyrazole-5-carboxamide
4-Fluoro-N-[6-[(2R)-morpholin-2-yl]-3-pyridyl]-3-propyl-1H-pyrazole-5-carboxamide
3-Cyclopropyl-4-fluoro-N-[6-[(2R)-morpholin-2-yl]-3-pyridyl]-1H-pyrazole-5-carboxamide
4-Bromo-3-cyclopropyl-N-[6-[(2R)-morpholin-2-yl]-3-pyridyl]-1H-pyrazole-5-carboxamide
3-Isobutyl-N-[6-[(2S)-morpholin-2-yl]-3-pyridyl]-1H-pyrazole-5-carboxamide
4-Fluoro-3-isobutyl-N-[6-[(2S)-morpholin-2-yl]-3-pyridyl]-1H-pyrazole-5-carboxamide
3-Butyl-4-fluoro-N-[6-[(2S)-morpholin-2-yl]-3-pyridyl]-1H-pyrazole-5-carboxamide
3-Butyl-N-[6-[(2S)-morpholin-2-yl]-3-pyridyl]-1H-pyrazole-5-carboxamide
5-Isopropyl-N-[6-[(2S)-morpholin-2-yl]-3-pyridyl]-2-(2,2,2-trifluoroethyl)pyrazole-3-carboxamide
2-Isopropyl-N-[6-[(2S)-morpholin-2-yl]-3-pyridyl]-5-(2,2,2-trifluoroethoxy)pyrazole-3-carboxamide
3-Isobutyl-N-[6-[(2R)-morpholin-2-yl]-3-pyridyl]-1H-pyrazole-5-carboxamide
4-Fluoro-3-isobutyl-N-[6-[(2R)-morpholin-2-yl]-3-pyridyl]-1H-pyrazole-5-carboxamide
3-Butyl-4-fluoro-N-[6-[(2R)-morpholin-2-yl]-3-pyridyl]-1H-pyrazole-5-carboxamide
3-Butyl-N-[6-[(2R)-morpholin-2-yl]-3-pyridyl]-1H-pyrazole-5-carboxamide
5-Isopropyl-N-[6-[(2R)-morpholin-2-yl]-3-pyridyl]-2-(2,2,2-trifluoroethyl)pyrazole-3-carboxamide
2-Isopropyl-N-[6-[(2R)-morpholin-2-yl]-3-pyridyl]-5-(2,2,2-trifluoroethoxy)pyrazole-3-carboxamide
4-Chloro-3-ethoxy-N-[6-[(2R)-morpholin-2-yl]-3-pyridyl]-1H-pyrazole-5-carboxamide
4-Chloro-N-[6-[(2S)-morpholin-2-yl]-3-pyridyl]-3-(2,2,2-trifluoroethoxy)-1H-pyrazole-5-carboxamide
4-Chloro-3-ethoxy-N-[6-[(2S)-morpholin-2-yl]-3-pyridyl]-1H-pyrazole-5-carboxamide
(RS)—N-(5-Chloro-6-morpholin-2-yl-3-pyridyl)-2-(trifluoromethyl)pyridine-4-carboxamide
(RS)-4-Chloro-N-(5-chloro-6-morpholin-2-yl-3-pyridyl)-3-propyl-1H-pyrazole-5-carboxamide
(RS)—N-(5-Fluoro-6-morpholin-2-yl-3-pyridyl)-2-(trifluoromethyl)pyridine-4-carboxamide
(RS)-4-Chloro-N-(5-fluoro-6-morpholin-2-yl-3-pyridyl)-3-propyl-1H-pyrazole-5-carboxamide
4-Chloro-3-isopropyl-N-[6-[(2R)-morpholin-2-yl]-3-pyridyl]-1H-pyrazole-5-carboxamide
4-Fluoro-3-isopropyl-N-[6-[(2R)-morpholin-2-yl]-3-pyridyl]-1H-pyrazole-5-carboxamide
(RS)—N-(5-Methyl-6-morpholin-2-yl-3-pyridyl)-2-(trifluoromethyl)pyridine-4-carboxamide
(RS)-4-Chloro-N-(5-methyl-6-morpholin-2-yl-3-pyridyl)-3-propyl-1H-pyrazole-5-carboxamide
4-Chloro-3-isopropyl-N-[6-[(2S)-morpholin-2-yl]-3-pyridyl]-1H-pyrazole-5-carboxamide or
4-Fluoro-3-isopropyl-N-[6-[(2S)-morpholin-2-yl]-3-pyridyl]-1H-pyrazole-5-carboxamide.

One further embodiment of the invention are compounds of formula I, in which "L" is —C(O)NH—, for example the following compounds (RS)-1-(3-Chlorophenyl)-3-(6-morpholin-2-yl-3-pyridyl)urea
(RS)-1-(4-Fluorophenyl)-3-(6-morpholin-2-yl-3-pyridyl)urea
(RS)-1-(6-Morpholin-2-yl-3-pyridyl)-3-[4-(trifluoromethyl)phenyl]urea
(RS)-1-(4-Chlorophenyl)-3-(6-morpholin-2-yl-3-pyridyl)urea
1-(3-Chlorophenyl)-3-[6-[(2S)-morpholin-2-yl]-3-pyridyl]urea
1-[6-[(2S)-Morpholin-2-yl]-3-pyridyl]-3-[3-(trifluoromethyl)phenyl]urea
1-(3-Chlorophenyl)-3-[6-[(2R)-morpholin-2-yl]-3-pyridyl]urea
1-[6-[(2R)-Morpholin-2-yl]-3-pyridyl]-3-[3-(trifluoromethyl)phenyl]urea
(RS)-1-(3-Chlorophenyl)-3-(2-morpholin-2-ylpyrimidin-5-yl)urea
(RS)-1-(5-Chloro-6-morpholin-2-yl-3-pyridyl)-3-(3-chlorophenyl)urea
(RS)-1-(3-Chlorophenyl)-3-(5-fluoro-6-morpholin-2-yl-3-pyridyl)urea or
(RS)-1-(3-Chlorophenyl)-3-(5-methyl-6-morpholin-2-yl-3-pyridyl)urea.

The preparation of compounds of formula I of the present invention may be carried out in sequential or convergent synthetic routes. Syntheses of the compounds of the invention are shown in the following schemes 1, 2, & 3 and in the description of 121 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1, 2, & 3, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods known in the art, for example, by processes described below, which process comprises a) reacting a compound of formula 14

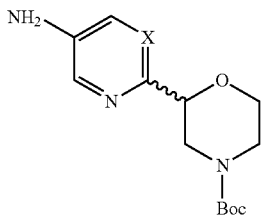

with a compound of formula 15-a

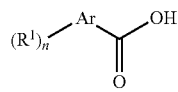

to afford a compound of formula 16-a

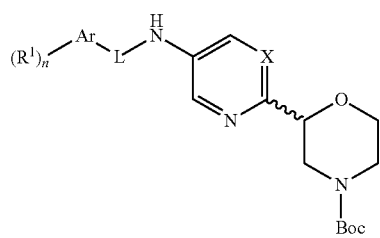

followed by de-protecting the Boc-group to afford compound of formula I

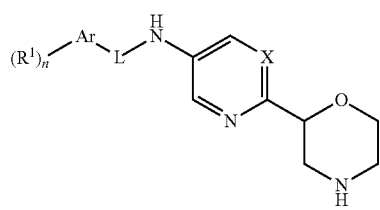

wherein L is —C(O)— and the other substituents are as described above, or b) reacting a compound of formula 14

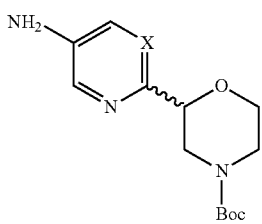

with a compound of formula 15-b

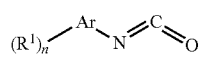

to afford a compound of formula 16-b

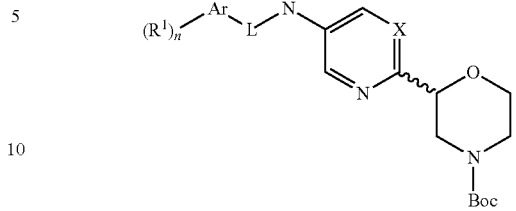

followed by de-protecting the Boc-group to afford a compound of formula I

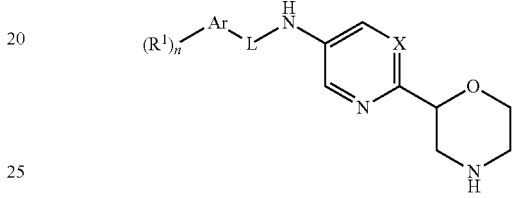

wherein L is —NHC(O)— and the other substituents are as described above, or c) reacting a compound of formula 8, 9 or 10

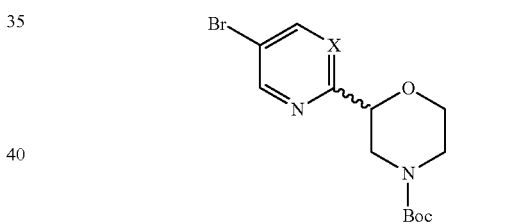

with a compound of formula 11

to afford a compound of formula 12

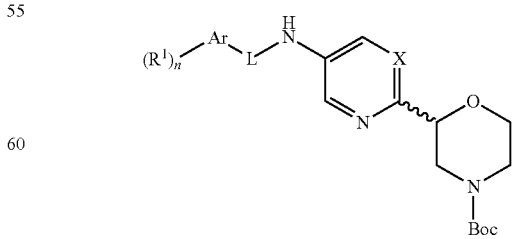

followed by de-protecting the Boc-group to afford a compound of formula I wherein L is a bond and the other substituents are as described above, and optionally, converting a compound of formula I into pharmaceutically acceptable acid addition salts.

GENERAL PROCEDURE

Scheme 1

The substituents are as described above.

Step A:

Conversion of ketone 1 to alpha-halogenated ketone 3 can be accomplished by treatment with halogenating reagents such as chlorine, bromine, N-chlorosuccinimide (NCS), N-bromosuccinimide (NBS) or tetraethylammonium trichloride, optionally with acids such as HBr, HCl, HOAc, p-toluenesulfonic acid as additives, in solvents such as $CH_2Cl_2$, $CHCl_3$, dioxane, THF, acetonitrile at room to elevated temperatures.

Preferred conditions are bromine in HBr/HOAc solution at 70° C. for 3 hours to form alpha-bromoketone 3 (hal=Br).

Step A':

Alternatively, alpha-halogenated ketone 3 can be obtained by a stepwise process involving acyl halide intermediates. Carboxylic acid 2 can be converted to corresponding acyl halides by treatment with halogenating reagents such as $(COCl)_2$, $SOCl_2$, $PCl_3$, $PBr_3$, or $Ph_3P.Br_2$, optionally in solvents such as $CH_2Cl_2$, $CHCl_3$, benzene, or toluene, at 0° C. to elevated temperatures. In the second step, acyl halide intermediate can be treated with (trimethylsilyl)diazomethane and then with concentrated HCl or HBr. The reaction can be carried out using a mixture of acetonitrile, THF, and diethyl ether as solvent at temperature between 0° C. and room temperature.

Preferred conditions are $(COCl)_2$ in $CH_2Cl_2$ at 0° C. to room temperature for the first step and mixing of reactants at 0-5° C. followed by allowing to react for 30 minutes at room temperature to form alpha-chloroketone 3 (hal=Cl).

Step B:

C—N bond formation can be accomplished through a nucleophilic substitution with N-benzylaminoethanol to afford alpha-amino ketone 4. The reaction can be carried out with bases such as triethylamine, diisopropylethylamine, $K_2CO_3$, $Na_2CO_3$, $Cs_2CO_3$, $KO^tBu$, in aprotic solvents such as DMF, acetonitrile, DMSO, THF, DME, or dioxane, at room temperature to elevated temperatures.

Preferred conditions are $K_2CO_3$ as the base in anhydrous DMF at room temperature.

Step C:

Conversion of ketone 4 to diol 5 can be accomplished by treatment by a reducing reagent such as $LiBH_4$, $NaBH_4$, $LiAlH_4$, or DIBAL-H, in a solvent such as MeOH, EtOH, THF, diethylether, or toluene at −78° C. to room temperature.

Preferred conditions are $NaBH_4$ in ethanol at room temperature for 1 hour.

Step D:

Cyclisation of diol 5 can be accomplished by an acid-mediated cation cyclisation or a stepwise process involving sulphonate ester intermediates.

In the acid-mediated cation cyclisation, the conversion can be accomplished by treatment with inorganic acids such as $H_2SO_4$ or $H_3PO_4$ at elevated temperatures.

In the stepwise process, the conversion can be accomplished by treatment of diol 5 with one equivalent of sulfonylating reagent, such as such as 1-(p-toluenesulfonyl) imidazole, methanesulfonyl chloride or toluenesulfonyl chloride, or in the presence of an inorganic base such as NaH, and $KO^tBu$, or an organic base, such as pyridine, triethyl amine, N,N-diisopropylethylamine or N-methylmorpholine, in ethereal solvents such as diethyl ether, dioxane, THF, or TBME, or using organic base as the solvent, at 0° C. to 50° C. The resulting sulphonate ester can be converted to morpholine 6 by treatment with a non-nucleophilic base such as sodium hydride, potassium tert-butoxide, or potassium 2-methyl-2-butoxide, in ethereal solvents such as diethyl ether, dioxane, THF, or TBME.

Preferred conditions are the stepwide process using NaH as the base and 1-(p-toluenesulfonyl) imidazole as the sulfonylating reagent, in THF at room temperature for 16 hours.

Step E:

Removal of benzyl protecting group can be accomplished by either a hydrogenation reaction catalyzed by a Pd catalyst or treatment with chloroformates such as $ClCOOCH_2CH_2Cl$, $ClCOOCH(Cl)Me$, $ClCOOCH_2Ph$, and $ClCOOCH_2CCl_3$, and optionally with a base such as triethylamine, diisopropylethylamine, and sodium hydroxide, in solvents such as dichloromethane, 1,2-dichloroethane, toluene, THF, diethylether, dioxane, TBME, methanol, and ethanol, at room temperature to elevated temperatures.

Preferred conditions are using $ClCOOCH(Cl)Me$ in dichloromethane for 4 hours at room temperature followed by in MeOH and toluene at refluxing temperature for 1 hour.

Step F:

Protection of the morpholine 7 can be accomplished by treatment with di-tert-butyl carbonate, optionally in the presence of an organic or inorganic base such as triethylamine, N,N-diisopropylethylamine, N-methylmorpholine, potassium carbonate, sodium carbonate, or cesium carbonate, in halogenated solvents such as dichloromethane or 1,2-dichloroethane or ethereal solvents such as diethyl ether, dioxane, THF, or TBME.

Preferred conditions are THF in the presence of potassium carbonate as the base at room temperature for 2 hours.

Step G:

Enantiomers of 8 can be separated using chiral HPLC. Preferred conditions are using SFC (Column: Chiralpak AD-3 100×4.6 mm I.D., 3 um) with ethanol (0.05% DEA) in $CO_2$ from 5% to 40% as the mobile phase.

Scheme 2

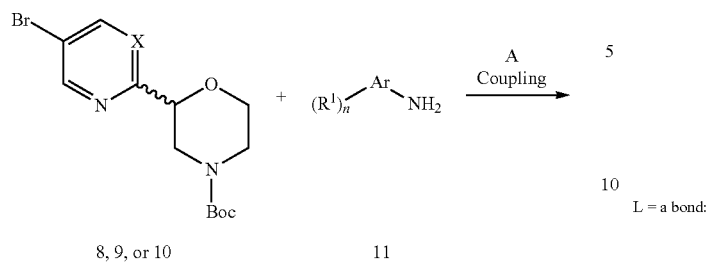

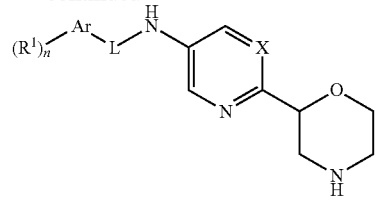

L = a bond:

Step A:
Coupling of aryl bromide 8, 9, or 10 with aryl amine 11 can be accomplished by treatment with a palladium or copper catalyst, a ligand, and a base in solvents such as dioxane, DMF, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic 4,5-bis(diphenylphosphino)-9,9-dimethylxanthene (Xantphos), and $Cs_2CO_3$, in dioxane at 90° C. for 12 hours.

Step B:
Removal of Boc N-protecting group can be effected with mineral acids such as HCl, $H_2SO_4$, or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH, or $H_2O$ at 0-80° C. Preferred conditions are $CF_3COOH$ as the acid in $CH_2Cl_2$ at room temperature for 1 hour.

Scheme 3

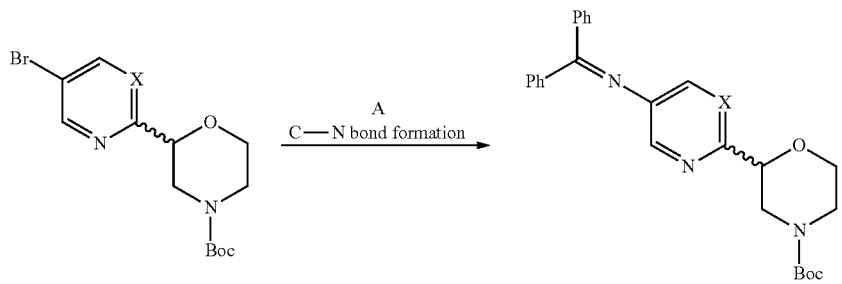

-continued

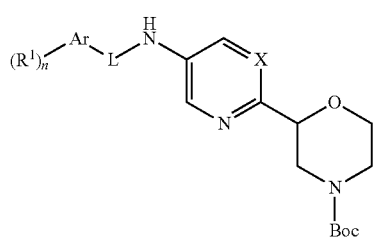

16-a:
L = —(CO)—

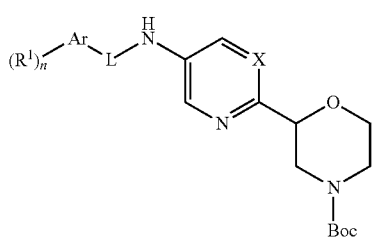

16-b:
L = —NH(CO)—

E
Deprotection

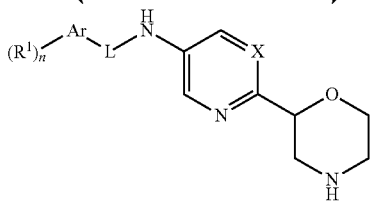

I

Step A:

C—N bond formation can be accomplished by treatment of bromide 8, 9 or 10 with benzophenone imine in the presence of a palladium or copper catalyst, a ligand and a base in solvents such as dioxane, DME, THF, toluene and DMSO at elevated temperatures, for instance using a palladium-catalysed Buchwald-Hartwig reaction.

Preferred conditions are catalytic tris(dibenzylidineacetone)dipalladium(0), catalytic 4,5-bis(diphenylphosphino)-9,9-dimethylxanthene (Xantphos), and $Cs_2CO_3$, in dioxane at 90° C. for 12 hours.

Step B:

Removal of diphenylmethylene N-protecting group can be accomplished by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, EtOAc, dichloromethane, chloroform, DMF or mixtures thereof.

The transformation can also be effected by treatment with hydroxylamine hydrochloride, together with as base such as sodium acetate, potassium acetate, sodium carbonate, potassium carbonate, cesium carbonate in solvents such as MeOH, EtOH, dioxane, THF, DMF or mixture thereof.

Preferred conditions are hydroxylamine hydrochloride, together with sodium acetate, in MeOH at room temperature for 1 hour.

Step C:

Amide formation can be accomplished by treatment with carboxylic acid 15-a and a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, dioxane, THF, DME, or TBME.

Preferred conditions are HATU with N,N-diisopropylethylamine in DMF at room temperature for 16 hours.

Step D:

Urea formation can be accomplished by treatment with isocyanate 15-b in the presence of an organic base such as triethylamine, N,N-diisopropylethylamine or N-methylmorpholine in halogenated solvents such as dichloromethane, 1,2-dichloroethane or chlorobenzene. Preferred conditions are triethylamine as the base in dichloromethane at room temperature.

Step E:

Removal of Boc N-protecting group can be effected with mineral acids such as HCl, $H_2SO_4$, or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH, or $H_2O$ at 0-80° C. Preferred conditions are $CF_3COOH$ as the acid in $CH_2Cl_2$ at room temperature for 1 hour.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Example 1

(RS)—N-(4-Chlorophenyl)-6-morpholin-2-yl-pyridin-3-amine

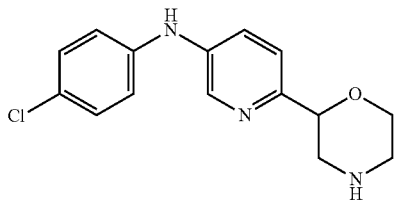

a) 2-Bromo-1-(5-bromo-2-pyridyl)ethanone

2-Acetyl-5-bromopyridine (10.0 g, CAS: 214701-49-2) in HBr/HOAc solution (35%~39%, 80 mL) was stirred at 70° C. for 5 min. $Br_2$ (9.6 g) was added dropwise. The reaction was continued at 70° C. for 3 h, TLC analysis showed complete consumption of the starting material. The mixture was cooled to room temperature and filtered through filtration paper. Volatiles were removed under reduced pressure, and the residue was dried further under high vacuum to give crude 2-bromo-1-(5-bromo-2-pyridyl)ethanone (16.8 g, yield: 93.3%) as a brown oil. The crude product was used in the next step without purification. MS (ESI): 281.9 ($[\{^{81}Br\}M+H]^+$), 277.9 ($[\{^{79}Br\}M+H]^+$).

b) 2-[Benzyl(2-hydroxyethyl)amino]-1-(5-bromo-2-pyridyl)ethanone

To the solution of 2-bromo-1-(5-bromo-2-pyridyl)ethanone (16.8 g) in anhydrous DMF (150 mL) was added $K_2CO_3$ (19.5 g) in portions at room temperature. N-benzylaminoethanol (10.2 g, CAS: 104-63-2) was added dropwise afterwards. The reaction was continued at room temperature until completion of reaction was indicated by TLC analysis. The mixture was poured into water (1000 mL) and extracted with EtOAc (2×1000 mL). The organic layers were combined and dried using $Na_2SO_4$. Volatiles were removed under reduced pressure. The residue was purified by flash chromatography (silica gel, petroleum ether/EtOAc=10:1 by vol) to give 2-[benzyl(2-hydroxyethyl)amino]-1-(5-bromo-2-pyridyl)ethanone as a light-brown oil (9 g, yield: 55%).

c) (RS)-2-[Benzyl(2-hydroxyethyl)amino]-1-(5-bromo-2-pyridyl)ethanol

At room temperature, to the solution of 2-[benzyl(2-hydroxyethyl)amino]-1-(5-bromo-2-pyridyl)ethanone (4.1 g) in EtOH (40 mL) was added $NaBH_4$ (540 mg, 14 mmol) in portions. After the completion of the reaction, indicated by TLC analysis, the reaction was quenched carefully by addition of saturated aqueous $NH_4Cl$ solution (200 mL). EtOH was removed under reduced pressure. The residue was extracted with EtOAc (2×100 mL). The combined organic extracts were dried by $Na_2SO_4$ and concentrated under reduced pressure. The residue was dried further under high vacuum to afford crude (RS)-2-[benzyl(2-hydroxyethyl)amino]-1-(5-bromo-2-pyridyl)ethanol (3 g, 73%), which was used for the next step without purification. MS (ESI): 352.9 ($[\{^{81}Br\}M+H]^+$), 350.9 ($[\{^{79}Br\}M+H]^+$).

d) (RS)-4-Benzyl-2-(5-bromo-2-pyridyl)morpholine

Sodium hydride (60%, 2.7 g) was added in portions to a solution of (RS)-2-[benzyl(2-hydroxyethyl)amino]-1-(5-bromo-2-pyridyl)ethanol (12 g) in THF (100 mL) at room temperature. The reaction mixture was stirred at room temperature for 2 h. The mixture was cooled to 0° C., and 1-(p-toluenesulfonyl)imidazole (7 g, CAS: 2232-08-8) was added in portions. After 30 minutes the mixture was warmed to room temperature. Stirring was continued overnight. The reaction was quenched with saturated aqueous ammonium chloride. The mixture was extracted with ethyl acetate, washed with brine, and dried over with $Na_2SO_4$. Purification by chromatography (silica gel, petroleum ether: ethyl acetate=3:1 by vol) afforded (RS)-4-benzyl-2-(5-bromo-2-pyridyl)morpholine (4 g, yield: 34.5%).

MS (ESI): 335.0 ($[\{^{81}Br\}M+H]^+$), 333.0 ($[\{^{79}Br\}M+H]^+$).

$^1$H NMR (DMSO-d$^6$): 8.60 (1H), 8.05 (1H), 7.42 (1H), 7.30 (5H), 4.51 (1H), 3.97 (1H), 3.82 (1H), 3.59 (1H), 3.47 (1H), 3.07 (1H), 2.75 (1H), 2.19 (1H), 1.91 (m, 1H).

e) (RS)-2-(4-bromophenyl)morpholine

A solution of (RS)-4-benzyl-2-(5-bromo-2-pyridyl)morpholine (4.35 g) and 1-chloroethyl chloroformate (2.5 g, CAS: 50893-53-3) in $CH_2Cl_2$ (50 mL) was stirred at room temperature for 4 h. TLC analysis showed that the starting material was consumed completely. Volatiles were removed under reduced pressure, and the residue was dried further under high vacuum. The residue was dissolved in MeOH (40 mL). The solution was stirred at refluxing temperature for an hour. TLC analysis demonstrated the completion of the reaction. Volatiles were removed under reduced pressure, and the residue was dried further under high vacuum to afford (RS)-2-(4-bromophenyl)morpholine (4.35 g, 13 mmol yield: 100%). The crude product was used for the next step directly.

MS (ESI): 244.9 ($[\{^{81}Br\}M+H]^+$), 242.9 ($[\{^{79}Br\}M+H]^+$).

f) (RS)-tert-Butyl 2-(5-bromo-2-pyridyl)morpholine-4-carboxylate

A solution of $K_2CO_3$ (5.38 g), di-tert-butyl dicarbonate (3.4 g, CAS: 424-99-5), and (RS)-2-(4-bromophenyl)morpholine (4.35 g, 13 mmol) from the above reaction (step e) in THF (50 mL) was stirred at room temperature for 2 hours. TLC analysis indicated the completion of the reaction. Water (200 mL) was added. The mixture was extracted with ethyl acetate (2×100 mL). The combined organic layers were washed with water (200 mL). The organic layer was concentrated under reduced pressure. Flash chromatography (silica gel, petroleum ether/EtOAc=3:1 by vol) gave (RS)-tert-butyl 2-(5-bromo-2-pyridyl)morpholine-4-carboxylate (3.95 g, 89% yield)

MS (ESI): 344.8 ([{$^{81}$Br}M+H]$^+$), 342.8 ([{$^{79}$Br}M+H]$^+$).

$^1$H NMR (DMSO-d$^6$): 8.69 (1H), 8.09 (1H), 7.46 (1H), 4.45 (2H), 4.00 (1H), 3.82 (1H), 3.63 (1H), 2.89 (2H), 1.43 (9H).

g) (RS)-tert-Butyl 2-[5-(4-chloroanilino)-2-pyridyl]morpholine-4-carboxylate A mixture of (RS)-tert-butyl 2-(5-bromo-2-pyridyl)morpholine-4-carboxylate (60 mg), 4-chloroaniline (25 mg, CAS: 106-47-8), 4,5-bis(diphenylphosphino)-9,9-dimethylxanthene (Xantphos, 20 mg, CAS: 161265-03-8), tris(dibenzylidineacetone)dipalladium(0) (16 mg, CAS: 51364-51-3), and Cs$_2$CO$_3$ (170 mg) in dioxane (3 mL) was stirred at 90° C. for 12 hours under N$_2$ atmosphere. LCMS indicated the completion of the reaction. The mixture was diluted with water (100 mL) and extracted with ethyl acetate (2×100 mL). The combined organic layers were washed with water (100 mL). The organic layer was concentrated under reduced pressure to afford crude (RS)-tert-butyl 2-[5-(4-chloroanilino)-2-pyridyl]morpholine-4-carboxylate as a brown oil. The crude product was used in the next step without purification.

h) (RS)—N-(4-Chlorophenyl)-6-morpholin-2-yl-pyridin-3-amine

Crude (RS)-tert-butyl 2-[5-(4-chloroanilino)-2-pyridyl]morpholine-4-carboxylate from the above reaction (step g) was dissolved in CH$_2$Cl$_2$ (3 mL) at room temperature. Trifluoroacetic acid (TFA, 1 mL, CAS: 76-05-1) was added. The reaction continued at room temperature for an hour Volatiles were removed at reduced pressure. Purification by Prep-HPLC (mobile phase A: H$_2$O, B: CH$_3$CN with 0.1% TFA, C18 column) gave (RS)—N-(4-chlorophenyl)-6-morpholin-2-yl-pyridin-3-amine (25 mg) as a light yellow waxy solid.

MS (ESI): 292.1 ([{$^{37}$Cl}M+H]$^+$), 290.1 ([{$^{35}$Cl}M+H]$^+$).

Example 2

(RS)—N-(4-Bromophenyl)-6-morpholin-2-yl-pyridin-3-amine

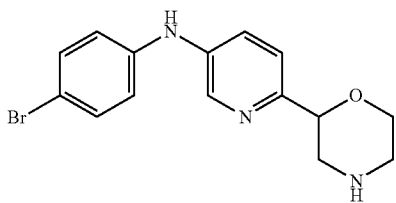 [SMILES: Clc1ccc(Nc2ccc(C3CNCCO3)nc2)cc1]

The title compound was obtained in analogy to example 1 using 4-bromoaniline (CAS: 106-40-1) instead of 4-chloroaniline in step (g). Light yellow waxy solid. MS (ESI): 336.0 ([{$^{81}$Br}M+H]$^+$), 334.1 ([{$^{79}$Br}M+H]$^+$).

Example 3

(RS)—N-(4-Ethoxyphenyl)-6-morpholin-2-yl-pyridin-3-amine

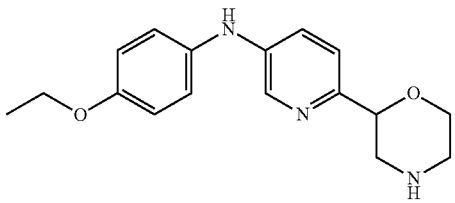 [SMILES: CCOc1ccc(Nc2ccc(C3CNCCO3)nc2)cc1]

The title compound was obtained in analogy to example 1 using 4-ethoxyaniline (CAS: 156-43-4) instead of 4-chloroaniline in step (g). Light yellow oil. MS (ESI): 300.2 ([M+H]$^+$).

Example 4

(RS)—N-(3-Chlorophenyl)-6-morpholin-2-yl-pyridin-3-amine

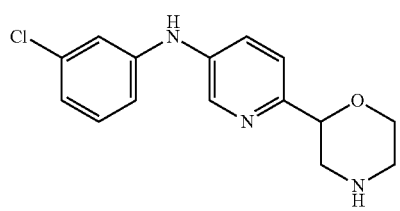 [SMILES: Clc1cccc(Nc2ccc(C3CNCCO3)nc2)c1]

The title compound was obtained in analogy to example 1 using 3-chloroaniline (CAS: 108-42-9) instead of 4-chloroaniline in step (g). Light yellow oil. MS (ESI): 292.0 ([{$^{37}$Cl}M+H]$^+$), 290.0 ([{$^{35}$Cl}M+H]$^+$).

Example 5

(RS)—N-(4-Fluorophenyl)-6-morpholin-2-yl-pyridin-3-amine

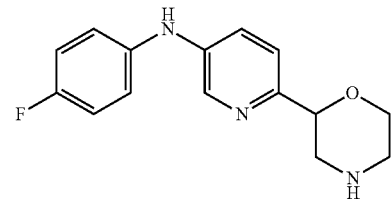 [SMILES: Fc1ccc(Nc2ccc(C3CNCCO3)nc2)cc1]

The title compound was obtained in analogy to example 1 using 4-fluoroaniline (CAS: 371-40-4) instead of 4-chloroaniline in step (g). Light yellow oil. MS (ESI): 274.1 ([M+H]$^+$).

Example 6

(RS)-6-Morpholin-2-yl-N-[4-(trifluoromethyl)phenyl]pyridin-3-amine

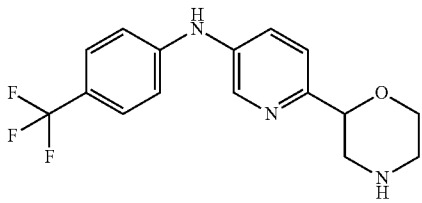 [SMILES: FC(F)(F)c1ccc(Nc2ccc(C3CNCCO3)nc2)cc1]

The title compound was obtained in analogy to example 1 using 4-(trifluoromethyl)aniline (CAS: 455-14-1) instead of 4-chloroaniline in step (g). Light yellow waxy solid. MS (ESI): 324.1 ([M+H]$^+$).

Example 7

(RS)-4-Chloro-N-(6-morpholin-2-yl-3-pyridyl)benzamide

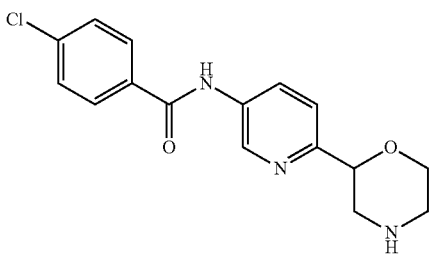 [SMILES: O=C(Nc1ccc(C2CNCCO2)nc1)c1ccc(Cl)cc1]

a) (RS)-tert-Butyl 2-[5-(benzhydrylideneamino)-2-pyridyl]morpholine-4-carboxylate A mixture of (RS)-tert-butyl 2-(5-bromo-2-pyridyl)morpholine-4-carboxylate (1.0 g), Example 1 benzophenone imine (580 mg, CAS: 1013-88-3), 4,5-bis(diphenylphosphino)-9,9-dimethylxanthene (Xantphos, 500 mg, CAS: 161265-03-8), tris(dibenzylidineacetone)dipalladium(0) (265 mg, CAS: 51364-51-3) and Cs$_2$CO$_3$ (2.8 g) in dioxane (40 mL) was degassed by bubbling argon into the mixture for several minutes. The reaction mixture was stirred at 90° C. for 12 hours under Ar atmosphere. TLC analysis showed the completion of the reaction. The crude reaction mixture was cooled to room temperature and filtered. The filtrate was concentrated in vacuo and the residue was diluted with water (100 mL). The mixture was extracted with ethyl acetate (2×100 mL). The combined organic layers were washed with water (100 mL) and concentrated to dryness. The residue was purified by flash chromatography (silica gel, CH$_2$Cl$_2$: MeOH=30:1 by vol) to give (RS)-tert-butyl 2-[5-(benzhydrylideneamino)-2-pyridyl]morpholine-4-carboxylate (1.28 g, yield: 99.9%) as a yellow solid.

b) (RS)-tert-Butyl 2-(5-amino-2-pyridyl)morpholine-4-carboxylate

A mixture of (RS)-tert-butyl 2-[5-(benzhydrylideneamino)-2-pyridyl]morpholine-4-carboxylate (1.28 g) from the above reaction (step a), hydroxylamine hydrochloride (320 mg, CAS: 5470-11-1) and NaOAc (2.38 g, CAS: 127-09-3) in methanol (50 mL) was stirred at room temperature for 3 hours. TLC analysis showed the completion of the reaction. The mixture was filtered and concentrated. Purification by flash chromatography (silica gel, CH$_2$Cl$_2$: MeOH=100:1 to 50:1 by vol) gave (RS)-tert-butyl 2-(5-amino-2-pyridyl)morpholine-4-carboxylate (450 mg, yield: 55.4%) as white solid.

MS (ESI): 280.0 ([M+H]$^+$).

c) (RS)-tert-Butyl 2-[5-[(4-chlorobenzoyl)amino]-2-pyridyl]morpholine-4-carboxylate (RS)-tert-Butyl 2-(5-amino-2-pyridyl)morpholine-4-carboxylate (35 mg), 4-chlorobenzoic acid (23 mg, CAS: 74-11-3), HATU (57 mg, CAS: 148893-10-1), and N,N-diisopropylethylamine (DIPEA, 49 mg, CAS: 7087-68-5) were dissolved in DMF (1.5 mL). The solution was stirred at room temperature until TLC analysis indicated completion of the reaction. The reaction was diluted with water (30 mL). The mixture was extracted with ethyl acetate (2×20 mL). The combined organic layers were dried with Na$_2$SO$_4$ and concentrated under reduced pressure. Further drying under high vacuum afforded crude (RS)-tert-butyl 2-[5-[(4-chlorobenzoyl)amino]-2-pyridyl]morpholine-4-carboxylate as a yellow solid, which was used in the next step without purification.

d) (RS)-4-Chloro-N-(6-morpholin-2-yl-3-pyridyl)benzamide (RS)-tert-Butyl 2-[5-[(4-chlorobenzoyl)amino]-2-pyridyl]morpholine-4-carboxylate from the above reaction (step c) was dissolved in a mixture of CH$_2$Cl$_2$ (2 mL) and trifluoroacetic acid (1 mL). The solution was stirred at room temperature for an hour until LCMS indicated completion of the reaction. The solution was concentrated under reduced pressure. Purification by Prep-HPLC (mobile phase A: H$_2$O, B: CH$_3$CN with 0.1% TFA, C18 column) gave (RS)-4-chloro-N-(6-morpholin-2-yl-3-pyridyl)benzamide (32 mg) as a white solid.

MS (ESI): 320.1 ([{$^{37}$Cl}M+H]$^+$), 318.1 ([{$^{35}$Cl}M+H]$^+$).

Example 8

(RS)-1-(3-Chlorophenyl)-3-(6-morpholin-2-yl-3-pyridyl)urea

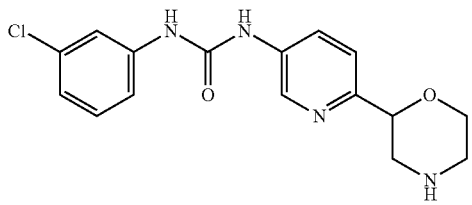 [SMILES: O=C(Nc1ccc(C2CNCCO2)nc1)Nc1cccc(Cl)c1]

a) (RS)-tert-Butyl 2-[5-[(3-chlorophenyl)carbamoylamino]-2-pyridyl]morpholine-4-carboxylate (RS)-tert-Butyl 2-(5-amino-2-pyridyl)morpholine-4-carboxylate (80 mg), Example 7(b), 3-chlorophenyl isocyanate (44 mg, CAS: 2909-38-8) and triethylamine (90 mg, CAS: 121-44-8) were dissolved in CH$_2$Cl$_2$ (1 mL). The solution was stirred at room temperature until TLC analysis indicated the completion of the reaction. Water (20 mL) was added.

The mixture was extracted by ethyl acetate (2×20 mL). The combined organic layers were dried with Na$_2$SO$_4$ and concentrated under reduced pressure. Further drying under high vacuum afforded crude (RS)-tert-butyl 2-[5-[(3-chlorophenyl)carbamoylamino]-2-pyridyl]morpholine-4-carboxylate as a yellow oil, which was used in the next step without purification.

b) (RS)-1-(3-Chlorophenyl)-3-(6-morpholin-2-yl-3-pyridyl)urea (RS)-tert-butyl 2-[5-[(3-chlorophenyl)carbamoylamino]-2-pyridyl]morpholine-4-carboxylate from the above reaction (step a) was dissolved in a mixture of trifluoroacetic acid (0.5 mL) and CH$_2$Cl$_2$ (2 mL). The solution was stirred at room temperature until TLC analysis indicated the completion of the reaction. Water (20 mL) was added. The mixture was extracted with ethyl acetate (2×20 mL). The aqueous layers were neutralized with saturated aqueous NaHCO$_3$ solution until neutral pH, and was extracted with CH$_2$Cl$_2$/CH$_3$OH (10:1 by vol. 20 mL). The combined organic layers were concentrated under reduced pressure. The residue was purified by prep-HPLC (mobile phase A: H$_2$O, B: CH$_3$CN with 0.1% TFA, C18 column) to give (RS)-1-(3-chlorophenyl)-3-(6-morpholin-2-yl-3-pyridyl)urea as a white solid (40 mg).

MS (ESI): 335.1 ([{$^{37}$Cl}M+H]$^+$), 333.1 ([{$^{35}$Cl}M+H]$^+$).

$^1$H NMR (Methanol-d$^4$): 8.75 (1H), 8.10 (1H), 7.68 (1H), 7.59 (1H), 7.30 (2H), 7.16 (1H), 4.91 (1H), 4.15 (1H), 4.37 (1H), 3.67 (1H), 3.36 (1H), 3.29 (2H).

Example 9

(RS)-1-(4-Fluorophenyl)-3-(6-morpholin-2-yl-3-pyridyl)urea

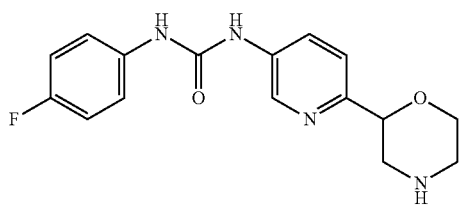 [SMILES: O=C(Nc1ccc(F)cc1)Nc1ccc(C2CNCCO2)nc1]

The title compound was obtained in analogy to example 8 using 4-fluorophenyl isocyanate (CAS: 1195-45-5) instead of 3-chlorophenyl isocyanate in step (a). Light yellow oil. MS (ESI): 317.1 ([M+H]$^+$).

Example 10

(RS)-1-(6-Morpholin-2-yl-3-pyridyl)-3-[4-(trifluoromethyl)phenyl]urea

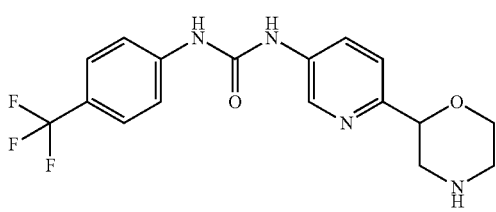 [SMILES: O=C(Nc1ccc(C(F)(F)F)cc1)Nc1ccc(C2CNCCO2)nc1]

The title compound was obtained in analogy to example 8 using 4-(trifluoromethyl)phenyl isocyanate (CAS: 1548-13-6) instead of 3-chlorophenyl isocyanate in step (a). Light yellow solid.

MS (ESI): 367.1 ([M+H]$^+$).

Example 11

(RS)-1-(4-Chlorophenyl)-3-(6-morpholin-2-yl-3-pyridyl)urea

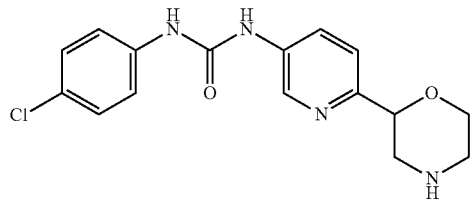 [SMILES: O=C(Nc1ccc(Cl)cc1)Nc1ccc(C2CNCCO2)nc1]

The title compound was obtained in analogy to example 8 using 4-chlorophenyl isocyanate (CAS: 104-12-1) instead of 3-chlorophenyl isocyanate in step (a). Off-white solid. MS (ESI): 335.1 ([{$^{37}$Cl}M+H]$^+$), 333.1 ([{$^{35}$Cl}M+H]$^+$).

Example 12

(RS)-3-Chloro-N-(6-morpholin-2-yl-3-pyridyl)benzamide

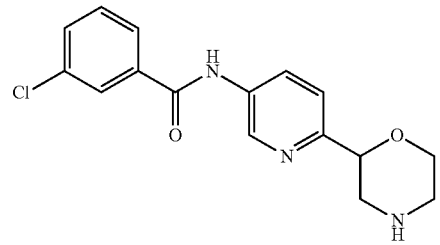 [SMILES: O=C(Nc1ccc(C2CNCCO2)nc1)c1cccc(Cl)c1]

The title compound was obtained in analogy to example 7 using 3-chlorobenzoic acid (CAS: 535-80-8) instead of 4-chlorobenzoic acid in step (c). Light yellow solid. MS (ESI): 320.1 ([{$^{37}$Cl}M+H]$^+$), 318.1 ([{$^{35}$Cl}M+H]$^+$).

Example 13

(RS)-4-Ethoxy-N-(6-morpholin-2-yl-3-pyridyl)benzamide

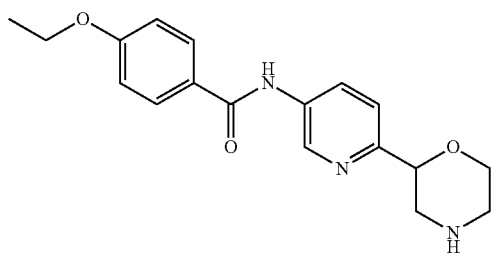 [SMILES: CCOc1ccc(C(=O)Nc2ccc(C3CNCCO3)nc2)cc1]

The title compound was obtained in analogy to example 7 using 4-ethoxybenzoic acid (CAS: 619-86-3) instead of 4-chlorobenzoic acid in step (c). White solid. MS (ESI): 328.2 ([M+H]$^+$).

Example 14

(RS)-4-Fluoro-N-(6-morpholin-2-yl-3-pyridyl)benzamide

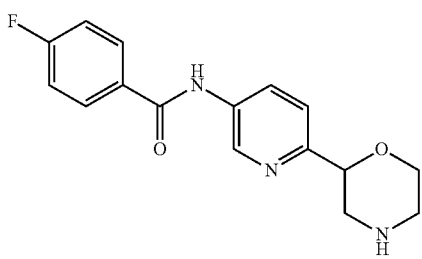 [SMILES: O=C(Nc1ccc(C2CNCCO2)nc1)c1ccc(F)cc1]

The title compound was obtained in analogy to example 7 using 4-fluorobenzoic acid (CAS: 456-22-4) instead of 4-chlorobenzoic acid in step (c). White solid. MS (ESI): 302.1 ([M+H]$^+$).

Example 15

(RS)-4-Chloro-N-(6-morpholin-2-yl-3-pyridyl)-3-propyl-1H-pyrazole-5-carboxamide

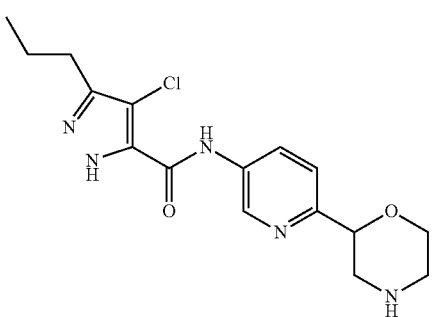 [SMILES: CCCC(=N)/C(Cl)=C(\N)C(=O)Nc1ccc(C2CNCCO2)nc1]

The title compound was obtained in analogy to example 7 using 4-chloro-5-propyl-1H-pyrazole-3-carboxylic acid (CAS: 1340578-20-2) instead of 4-chlorobenzoic acid in step (c). White solid.
MS (ESI): 352.1 ([{$^{37}$Cl}M+H]$^+$), 350.1 ([{$^{35}$Cl}M+H]$^+$).

Example 16

(RS)—N-(6-Morpholin-2-yl-3-pyridyl)-2-(trifluoromethyl)pyridine-4-carboxamide

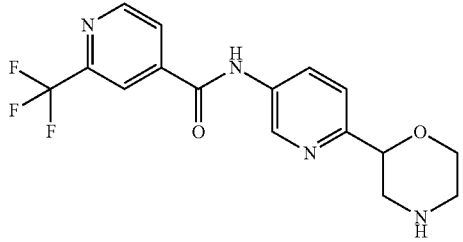 [SMILES: O=C(Nc1ccc(C2CNCCO2)nc1)c1ccnc(C(F)(F)F)c1]

The title compound was obtained in analogy to example 7 using 2-(trifluoromethyl)pyridine-4-carboxylic acid (CAS: 131747-41-6) instead of 4-chlorobenzoic acid in step (c). Light yellow solid. MS (ESI): 353.0 ([M+H]$^+$).

Example 17

(RS)—N-(6-Morpholin-2-yl-3-pyridyl)-2-(trifluoromethyl)pyrimidin-4-amine

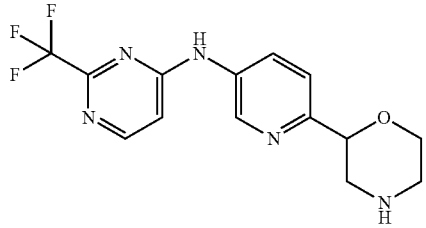 [SMILES: FC(F)(F)c1nccc(Nc2ccc(C3CNCCO3)nc2)n1]

The title compound was obtained in analogy to example 1 using 2-(trifluoromethyl)pyrimidin-4-amine (CAS: 672-42-4) instead of 4-chloroaniline in step (g). White solid. MS (ESI): 326.2 ([M+H]$^+$).

Example 18

N-(4-Chlorophenyl)-6-[(2S)-morpholin-2-yl]pyridin-3-amine

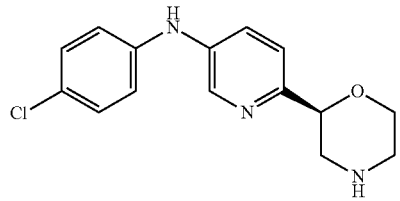

a) tert-Butyl (2R)-2-(5-bromo-2-pyridyl)morpholine-4-carboxylate and tert-butyl (2S)-2-(5-bromo-2-pyridyl)morpholine-4-carboxylate (RS)-tert-Butyl 2-(5-bromo-2-pyridyl)morpholine-4-carboxylate was separated by SFC using the following conditions: Chiralpak AD-3 column (100×4.6 mm I.D.: 3 um); ethanol (0.05% DEA) in CO$_2$ from 5% to 40% as the mobile phase; 3 mL/min flow rate; Wavelength: 220 nm. tert-Butyl (2S)-2-(5-bromo-2-pyridyl)morpholine-4-carboxylate (1.6 g, retention time: 1.421 min) was obtained as the first fraction. tert-Butyl (2R)-2-(5-bromo-2-pyridyl)morpholine-4-carboxylate (1.6 g, retention time: 1.571 min) was obtained as the second fraction.

b) N-(4-Chlorophenyl)-6-[(2S)-morpholin-2-yl]pyridin-3-amine

N-(4-Chlorophenyl)-6-[(2S)-morpholin-2-yl]pyridin-3-amine was obtained in analogy to example 1 using tert-butyl (2S)-2-(5-bromo-2-pyridyl)morpholine-4-carboxylate instead of (RS)-tert-butyl 2-(5-bromo-2-pyridyl)morpholine-4-carboxylate to react with 4-chloroaniline (CAS: 106-47-8) in step (g). Waxy solid. MS (ESI): 292.1 ([{$^{37}$Cl}M+H]$^+$), 290.2 ([{$^{35}$Cl}M+H]$^+$).

Example 19

6-[(2S)-Morpholin-2-yl]-N-[4-(trifluoromethyl)phenyl]pyridin-3-amine

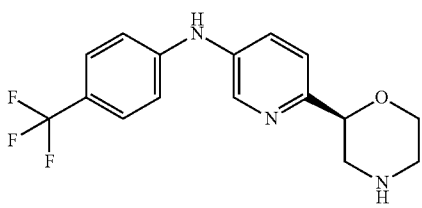 [SMILES: FC(F)(F)c1ccc(Nc2ccc([C@@H]3CNCCO3)nc2)cc1]

The title compound was obtained in analogy to example 18 using 4-(trifluoromethyl)aniline (CAS: 455-14-1) instead of 4-chloroaniline in step (b). White solid. MS (ESI): 324.0 ([M+H]$^+$).

Example 20

N-(5-Chloro-2-pyridyl)-6-[(2S)-morpholin-2-yl]pyridin-3-amine

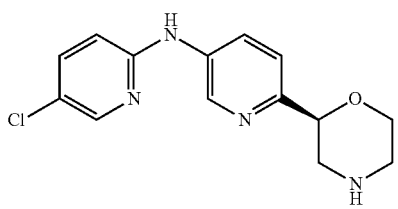 [SMILES: Clc1ccc(Nc2ccc([C@@H]3CNCCO3)nc2)nc1]

The title compound was obtained in analogy to example 18 using 2-amino-5-chloropyridine (CAS: 1072-98-6) instead of 4-chloroaniline in step (b). White solid. MS (ESI): 293.0 ([{$^{37}$Cl}M+H]$^+$), 291.0 ([{$^{35}$Cl}M+H]$^+$).

Example 21

N-(5-Bromo-2-pyridyl)-6-[(2S)-morpholin-2-yl]pyridin-3-amine

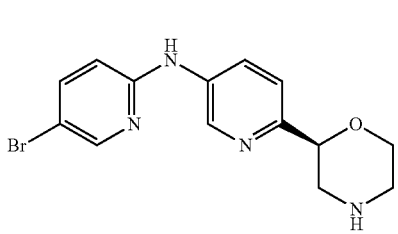 [SMILES: Brc1ccc(Nc2ccc([C@@H]3CNCCO3)nc2)nc1]

The title compound was obtained in analogy to example 18 using 2-amino-5-bromopyridine (CAS: 1072-97-5) instead of 4-chloroaniline in step (b). White solid. MS (ESI): 337.0 ([{$^{81}$Br}M+H]$^+$), 335.0 ([{$^{79}$Br}M+H]$^+$).

Example 22

6-[(2S)-Morpholin-2-yl]-N-[6-(trifluoromethyl)-3-pyridyl]pyridin-3-amine

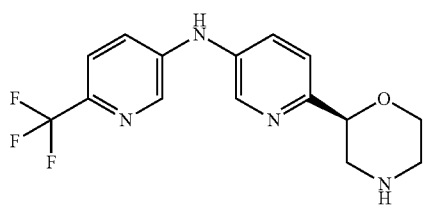 [SMILES: FC(F)(F)c1ccc(Nc2ccc([C@@H]3CNCCO3)nc2)cn1]

The title compound was obtained in analogy to example 18 using 5-amino-2-(trifluoromethyl) pyridine (CAS: 106877-33-2) instead of 4-chloroaniline in step (b). White solid. MS (ESI): 325.1 ([M+H]$^+$).

Example 23

6-[(2S)-Morpholin-2-yl]-N-[4-(trifluoromethyl)-2-pyridyl]pyridin-3-amine

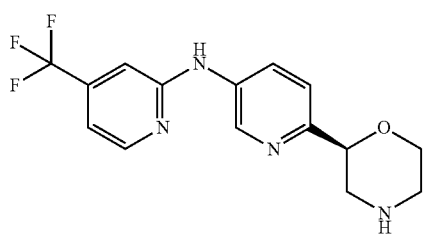 [SMILES: FC(F)(F)c1ccnc(Nc2ccc([C@@H]3CNCCO3)nc2)c1]

The title compound was obtained in analogy to example 18 using 2-amino-4-(trifluoromethyl) pyridine (CAS: 106447-97-6) instead of 4-chloroaniline in step (b). White solid. MS (ESI): 325.1 ([M+H]$^+$).

Example 24

N-(4-Chlorophenyl)-6-[(2R)-morpholin-2-yl]pyridin-3-amine

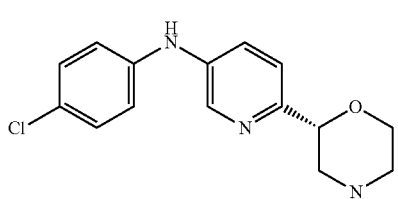

The title compound was obtained in analogy to example 1 using tert-butyl (2R)-2-(5-bromo-2-pyridyl)morpholine-4-carboxylate instead of (RS)-tert-butyl 2-(5-bromo-2-pyridyl)morpholine-4-carboxylate to react with 4-chloroaniline (CAS: 106-47-8) in step (g). Waxy solid. MS (ESI): 292.1 ([{³⁷Cl}M+H]⁺), 290.1 ([{³⁵Cl}M+H]⁺).

Example 25

6-[(2R)-Morpholin-2-yl]-N-[4-(trifluoromethyl)phenyl]pyridin-3-amine

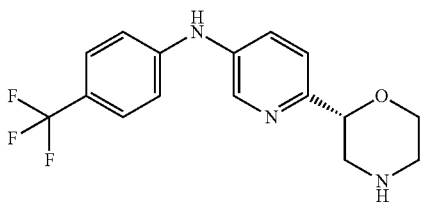 [SMILES: FC(F)(F)c1ccc(Nc2ccc([C@H]3CNCCO3)nc2)cc1]

The title compound was obtained in analogy to example 24 using 4-(trifluoromethyl)aniline (CAS: 455-14-1) instead of 4-chloroaniline. White solid. MS (ESI): 324.0 ([M+H]⁺).

Example 26

N-(5-Chloro-2-pyridyl)-6-[(2R)-morpholin-2-yl]pyridin-3-amine

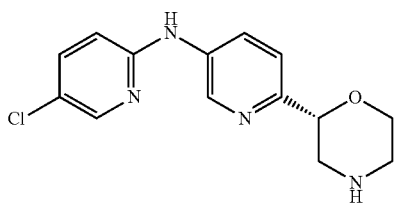 [SMILES: Clc1ccc(Nc2ccc([C@H]3CNCCO3)nc2)nc1]

The title compound was obtained in analogy to example 24 using 2-amino-5-chloropyridine (CAS: 1072-98-6) instead of 4-chloroaniline. White solid. MS (ESI): 293.1 ([{³⁷Cl}M+H]⁺), 291.1 ([{³⁵Cl}M+H]⁺).

Example 27

6-[(2R)-Morpholin-2-yl]-N-[6-(trifluoromethyl)-3-pyridyl]pyridin-3-amine

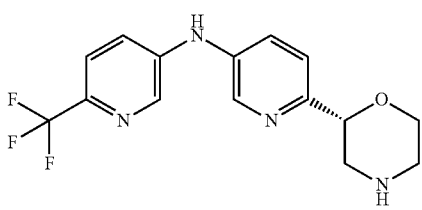 [SMILES: FC(F)(F)c1ccc(Nc2ccc([C@H]3CNCCO3)nc2)cn1]

The title compound was obtained in analogy to example 24 using 5-amino-2-(trifluoromethyl) pyridine (CAS: 106877-33-2) instead of 4-chloroaniline. White solid. MS (ESI): 325.0 ([M+H]⁺).

Example 28

6-[(2R)-Morpholin-2-yl]-N-[4-(trifluoromethyl)-2-pyridyl]pyridin-3-amine

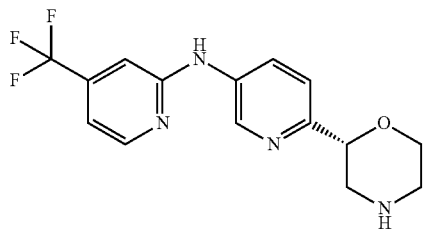 [SMILES: FC(F)(F)c1ccnc(Nc2ccc([C@H]3CNCCO3)nc2)c1]

The title compound was obtained in analogy to example 24 using 2-amino-4-(trifluoromethyl) pyridine (CAS: 106447-97-6) instead of 4-chloroaniline. White solid. MS (ESI): 325.0 ([M+H]⁺).

Example 29

N-[6-[(2S)-Morpholin-2-yl]-3-pyridyl]-5-(trifluoromethyl)pyridin-2-amine

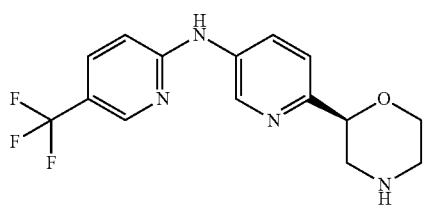 [SMILES: FC(F)(F)c1ccc(Nc2ccc([C@@H]3CNCCO3)nc2)nc1]

The title compound was obtained in analogy to example 18 using 2-amino-5-(trifluoromethyl) pyridine (CAS: 74784-70-6) instead of 4-chloroaniline in step (b). White solid. MS (ESI): 325.1 ([M+H]⁺).

Example 30

N-[6-[(2S)-Morpholin-2-yl]-3-pyridyl]-6-(trifluoromethyl)pyridin-2-amine

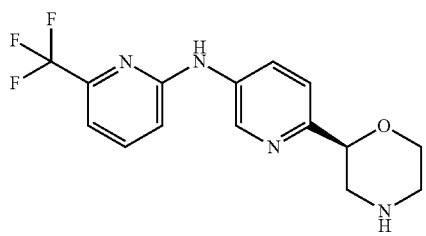 [SMILES: FC(F)(F)c1cccc(Nc2ccc([C@@H]3CNCCO3)nc2)n1]

The title compound was obtained in analogy to example 18 using 2-amino-6-(trifluoromethyl) pyridine (CAS: 34486-24-3) instead of 4-chloroaniline in step (b). White solid. MS (ESI): 325.0 ([M+H]⁺).

Example 31

4-Chloro-N-[6-[(2S)-morpholin-2-yl]-3-pyridyl]benzamide

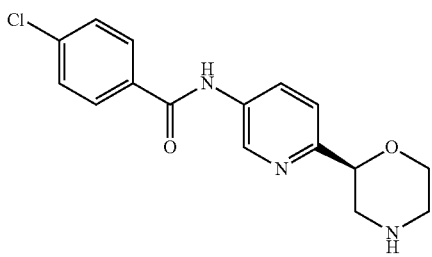 [SMILES: O=C(Nc1ccc([C@@H]2CNCCO2)nc1)c1ccc(Cl)cc1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a). White solid. MS (ESI): 319.9 ([{$^{37}$Cl}M+H]$^+$), 317.9 ([{$^{35}$Cl}M+H]$^+$).

Example 32

3-Chloro-N-[6-[(2S)-morpholin-2-yl]-3-pyridyl]benzamide

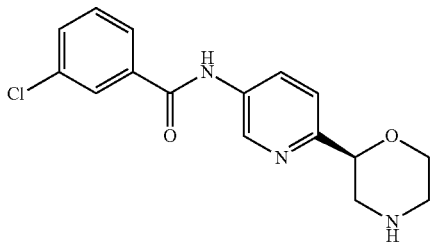 [SMILES: O=C(Nc1ccc([C@@H]2CNCCO2)nc1)c1cccc(Cl)c1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 3-chlorobenzoic acid (CAS: 535-80-8) instead of 4-chlorobenzoic acid in step (c). White solid. MS (ESI): 319.9 ([{$^{37}$Cl}M+H]$^+$), 317.9 ([{$^{35}$Cl}M+H]$^+$).

Example 33

N-[6-[(2S)-Morpholin-2-yl]-3-pyridyl]-4-(trifluoromethyl)benzamide

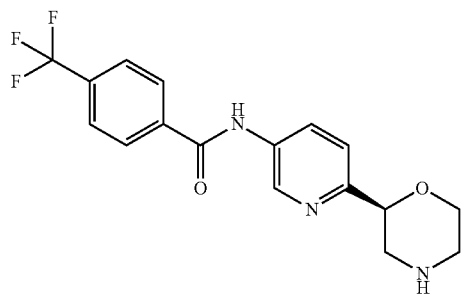 [SMILES: O=C(Nc1ccc([C@@H]2CNCCO2)nc1)c1ccc(C(F)(F)F)cc1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 4-(trifluoromethyl)benzoic acid (CAS: 455-24-3) instead of 4-chlorobenzoic acid in step (c). White solid. MS (ESI): 352.0 ([M+H]$^+$).

Example 34

N-[6-[(2S)-Morpholin-2-yl]-3-pyridyl]-2-(trifluoromethyl)pyridine-4-carboxamide

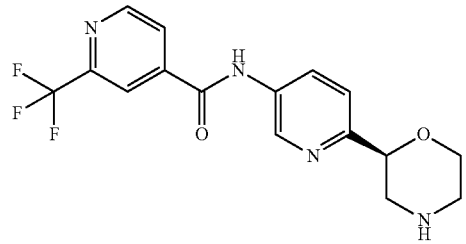 [SMILES: O=C(Nc1ccc([C@@H]2CNCCO2)nc1)c1ccnc(C(F)(F)F)c1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 2-(trifluoromethyl)pyridine-4-carboxylic acid (CAS: 131747-41-6) instead of 4-chlorobenzoic acid in step (c). White solid. MS (ESI): 352.9 ([M+H]$^+$).

Example 35

N-[6-[(2S)-Morpholin-2-yl]-3-pyridyl]-3-(trifluoromethyl)benzamide

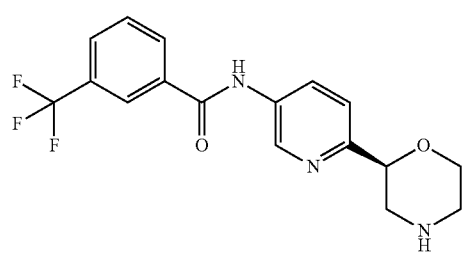 [SMILES: O=C(Nc1ccc([C@@H]2CNCCO2)nc1)c1cccc(C(F)(F)F)c1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 3-(trifluoromethyl)benzoic acid (CAS: 454-92-2) instead of 4-chlorobenzoic acid in step (c). White solid. MS (ESI): 352.0 ([M+H]$^+$).

Example 36

N-[6-[(2S)-Morpholin-2-yl]-3-pyridyl]-6-(2,2,2-trifluoroethoxy)pyridine-3-carboxamide

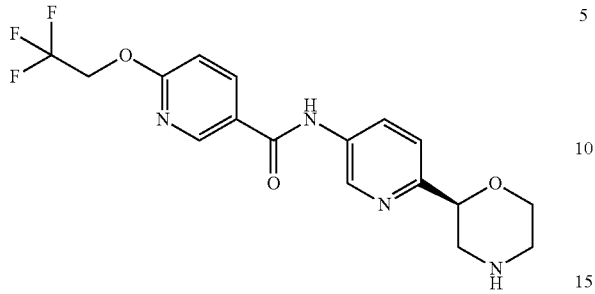

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 6-(2,2,2-trifluoroethoxy)nicotinic acid (CAS: 175204-90-7) instead of 4-chlorobenzoic acid in step (c). White solid. MS (ESI): 382.9 ([M+H]$^+$).

Example 37

2-Ethyl-N-[6-[(2S)-morpholin-2-yl]-3-pyridyl]pyrimidine-5-carboxamide

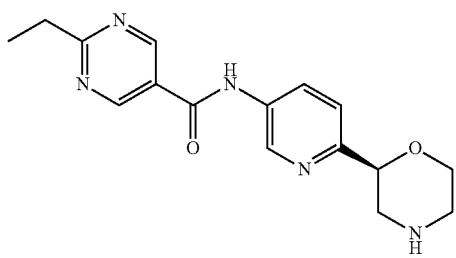 [SMILES: CCc1ncc(C(=O)Nc2ccc([C@@H]3CNCCO3)nc2)cn1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 2-ethylpyrimidine-5-carboxylic acid (CAS: 72790-16-0) instead of 4-chlorobenzoic acid in step (c). White solid. MS (ESI): 314.0 ([M+H]$^+$).

Example 38

3-Isopropyl-N-[6-[(2S)-morpholin-2-yl]-3-pyridyl]-1H-pyrazole-5-carboxamide

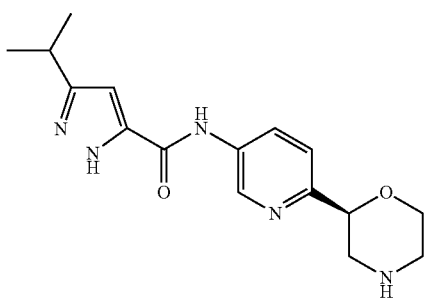 [SMILES: CC(C)C(=N)/C=C(\N)C(=O)Nc1ccc([C@@H]2CNCCO2)nc1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 3-isopropylpyrazole-5-carboxylic acid (CAS: 92933-47-6) instead of 4-chlorobenzoic acid in step (c). White solid. MS (ESI): 316.0 ([M+H]$^+$).

Example 39

4-Chloro-N-[6-[(2S)-morpholin-2-yl]-3-pyridyl]-3-propyl-1H-pyrazole-5-carboxamide

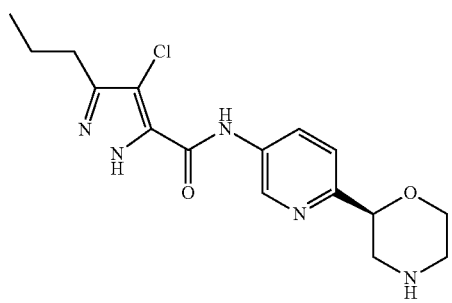 [SMILES: CCCC(=N)/C(Cl)=C(\N)C(=O)Nc1ccc([C@@H]2CNCCO2)nc1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 4-chloro-5-propyl-1H-pyrazole-3-carboxylic acid (CAS: 1340578-20-2) instead of 4-chlorobenzoic acid in step (c). White solid. MS (ESI): 352.1 ([{$^{37}$Cl}M+H]$^+$), 350.1 ([{$^{35}$Cl}M+H]$^+$).

Example 40

4-Chloro-3-cyclopropyl-N-[6-[(2S)-morpholin-2-yl]-3-pyridyl]-1H-pyrazole-5-carboxamide

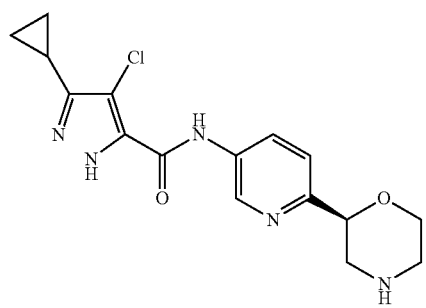 [SMILES: N=C(/C(Cl)=C(\N)C(=O)Nc1ccc([C@@H]2CNCCO2)nc1)C1CC1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 4-chloro-3-cyclopropyl-1H-pyrazole-5-carboxylic acid (CAS: 1291275-83-6) instead of 4-chlorobenzoic acid in step (c). White solid. MS (ESI): 349.9 ([{$^{37}$Cl}M+H]$^+$), 347.9 ([{$^{35}$Cl}M+H]$^+$).

Example 41

1-(3-Chlorophenyl)-3-[6-[(2S)-morpholin-2-yl]-3-pyridyl]urea

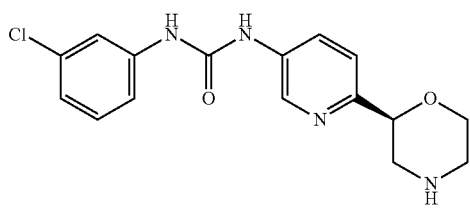 [SMILES: O=C(Nc1ccc([C@@H]2CNCCO2)nc1)Nc1cccc(Cl)c1]

The title compound was obtained in analogy to example 8 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a). White solid. MS (ESI): 335.0 ([{$^{37}$Cl}M+H]$^+$), 333.0 ([{$^{35}$Cl}M+H]$^+$).

Example 42

1-[6-[(2S)-Morpholin-2-yl]-3-pyridyl]-3-[3-(trifluoromethyl)phenyl]urea

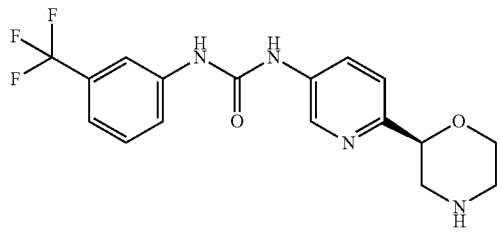 [SMILES: O=C(Nc1ccc([C@@H]2CNCCO2)nc1)Nc1cccc(C(F)(F)F)c1]

The title compound was obtained in analogy to example 8 using tert-butyl (2S)-2-(5-bromo-2-pyridyl)morpholine-4-carboxylate instead of (RS)-tert-butyl 2-(5-bromo-2-pyridyl)morpholine-4-carboxylate, and 3-(trifluoromethyl)phenyl isocyanate (CAS: 329-01-1) instead of 3-chlorophenyl isocyanate in step (a). White solid. MS (ESI): 367.0 ([M+H]$^+$).

Example 43

4-Chloro-N-[6-[(2S)-morpholin-2-yl]-3-pyridyl]-3-(trifluoromethyl)-1H-pyrazole-5-carboxamide

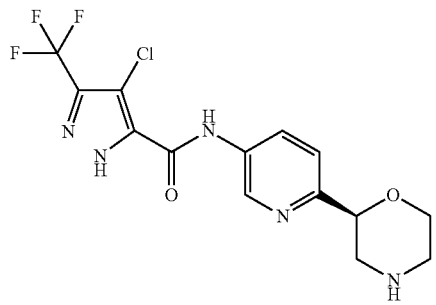 [SMILES: N=C(/C(Cl)=C(\N)C(=O)Nc1ccc([C@@H]2CNCCO2)nc1)C(F)(F)F]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 4-chloro-5-(trifluoromethyl)-2H-pyrazole-3-carboxylic acid (CAS: 934758-95-9) instead of 4-chlorobenzoic acid in step (c). White solid. MS (ESI): 377.9 ([{$^{37}$Cl}M+H]$^+$), 375.9 ([{$^{35}$Cl}M+H]$^+$).

Example 44

4-Chloro-3-methyl-N-[6-[(2S)-morpholin-2-yl]-3-pyridyl]-1H-pyrazole-5-carboxamide

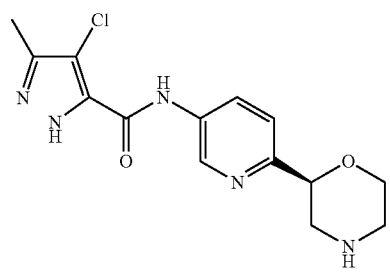 [SMILES: CC(=N)/C(Cl)=C(\N)C(=O)Nc1ccc([C@@H]2CNCCO2)nc1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 4-chloro-3-methyl-1H-pyrazole-5-carboxylic acid (CAS: 29400-84-8) instead of 4-chlorobenzoic acid in step (c). White solid. MS (ESI): 324.1 ([{$^{37}$Cl}M+H]$^+$), 322.2 ([{$^{35}$Cl}M+H]$^+$).

Example 45

4-Methyl-N-[6-[(2S)-morpholin-2-yl]-3-pyridyl]-1H-pyrazole-5-carboxamide

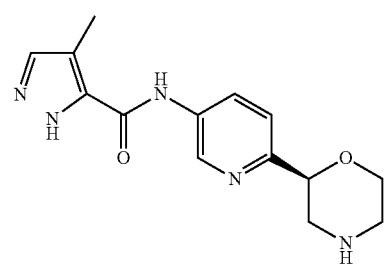 [SMILES: C/C(C=N)=C(/N)C(=O)Nc1ccc([C@@H]2CNCCO2)nc1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 4-methyl-1H-pyrazole-3-carboxylic acid (CAS: 82231-51-4) instead of 4-chlorobenzoic acid in step (c). White solid. MS (ESI): 288.2 ([M+H]$^+$).

Example 46

4-Chloro-1-methyl-N-[6-[(2S)-morpholin-2-yl]-3-pyridyl]-5-propyl-pyrazole-3-carboxamide

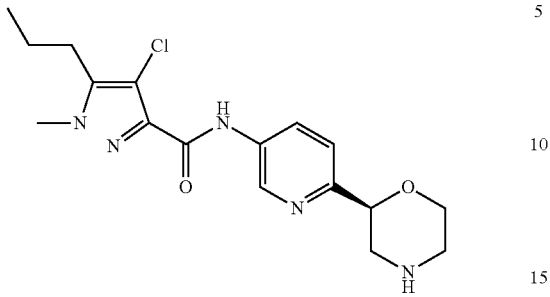

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 4-chloro-1-methyl-5-propyl-1H-pyrazole-3-carboxylic acid (CAS: 1248078-41-2) instead of 4-chlorobenzoic acid in step (c). White solid. MS (ESI): 366.0 ([$\{^{37}Cl\}$M+H]$^+$), 364.0 ([$\{^{35}Cl\}$M+H]$^+$).

Example 47

N-(5-Bromo-2-pyridyl)-6-[(2R)-morpholin-2-yl]pyridin-3-amine

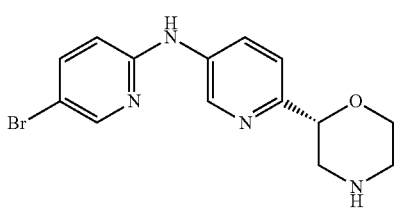

The title compound was obtained in analogy to example 1 using tert-butyl (2R)-2-(5-bromo-2-pyridyl)morpholine-4-carboxylate instead of (RS)-tert-butyl 2-(5-bromo-2-pyridyl)morpholine-4-carboxylate, and 2-amino-5-bromopyridine (CAS: 1072-97-5) instead of 4-chloroaniline (CAS: 106-47-8) in step (g). Waxy solid. MS (ESI): 337.0 ([$\{^{81}Br\}$M+H]$^+$), 335.1 ([$\{^{79}Br\}$M+H]$^+$).

Example 48

4-Chloro-1-methyl-N-[6-[(2R)-morpholin-2-yl]-3-pyridyl]-5-propyl-pyrazole-3-carboxamide

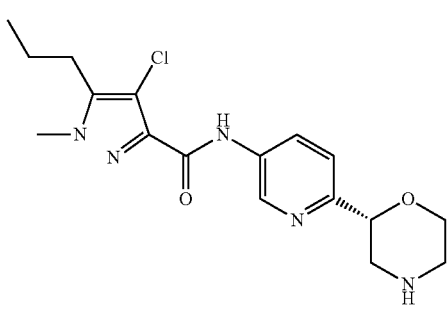 [SMILES: CCC/C(NC)=C(\Cl)C(=N)C(=O)Nc1ccc([C@H]2CNCCO2)nc1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 4-chloro-1-methyl-5-propyl-1H-pyrazole-3-carboxylic acid (CAS: 1248078-41-2) instead of 4-chlorobenzoic acid in step (c). White solid. MS (ESI): 366.2 ([$\{^{37}Cl\}$M+H]$^+$), 364.2 ([$\{^{35}Cl\}$M+H]$^+$).

Example 49

N-[6-[(2R)-Morpholin-2-yl]-3-pyridyl]-5-(trifluoromethyl)pyridin-2-amine

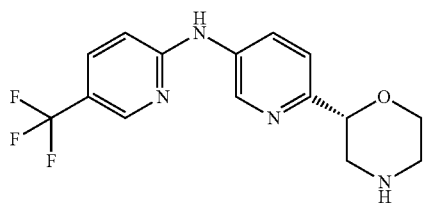 [SMILES: FC(F)(F)c1ccc(Nc2ccc([C@H]3CNCCO3)nc2)nc1]

The title compound was obtained in analogy to example 1 using tert-butyl (2R)-2-(5-bromo-2-pyridyl)morpholine-4-carboxylate instead of (RS)-tert-butyl 2-(5-bromo-2-pyridyl)morpholine-4-carboxylate, and 2-amino-5-(trifluoromethyl)pyridine (CAS: 74784-70-6) instead of 4-chloroaniline (CAS: 106-47-8) in step (g). White solid. MS (ESI): 325.2 ([M+H]$^+$).

Example 50

N-[6-[(2R)-Morpholin-2-yl]-3-pyridyl]-6-(trifluoromethyl)pyridin-2-amine

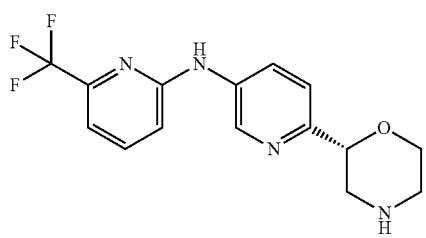 [SMILES: FC(F)(F)c1cccc(Nc2ccc([C@H]3CNCCO3)nc2)n1]

The title compound was obtained in analogy to example 1 using tert-butyl (2R)-2-(5-bromo-2-pyridyl)morpholine-4-carboxylate instead of (RS)-tert-butyl 2-(5-bromo-2-pyridyl)morpholine-4-carboxylate, and 2-amino-6-(trifluoromethyl)pyridine (CAS: 34486-24-3) instead of 4-chloroaniline (CAS: 106-47-8) in step (g). White solid. MS (ESI): 325.2 ([M+H]$^+$).

Example 51

4-Chloro-N-[6-[(2R)-morpholin-2-yl]-3-pyridyl]benzamide

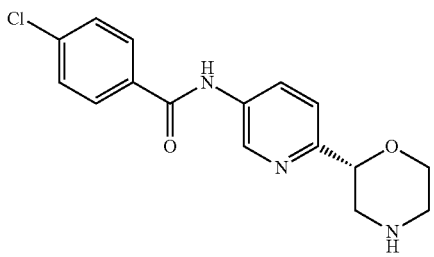 [SMILES: O=C(Nc1ccc([C@H]2CNCCO2)nc1)c1ccc(Cl)cc1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a). White solid. MS (ESI): 320.1 ([{$^{37}$Cl}M+H]$^+$), 318.1 ([{$^{35}$Cl}M+H]$^+$).

Example 52

3-Chloro-N-[6-[(2R)-morpholin-2-yl]-3-pyridyl]benzamide

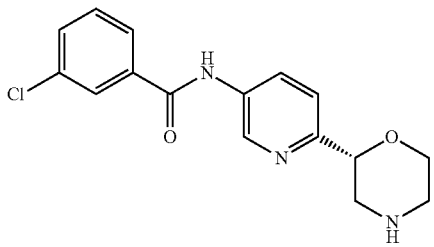

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 3-chlorobenzoic acid (CAS: 535-80-8) instead of 4-chlorobenzoic acid in step (c). White solid. MS (ESI): 320.1 ([{$^{37}$Cl}M+H]$^+$), 318.1 ([{$^{35}$Cl}M+H]$^+$).

Example 53

N-[6-[(2R)-Morpholin-2-yl]-3-pyridyl]-4-(trifluoromethyl)benzamide

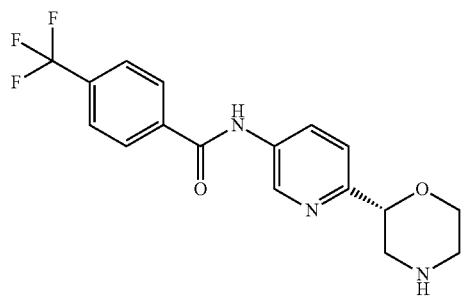 [SMILES: O=C(Nc1ccc([C@H]2CNCCO2)nc1)c1ccc(C(F)(F)F)cc1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 4-(trifluoromethyl)benzoic acid (CAS: 455-24-3) instead of 4-chlorobenzoic acid in step (c). White solid. MS (ESI): 352.2 ([M+H]$^+$).

Example 54

N-[6-[(2R)-Morpholin-2-yl]-3-pyridyl]-2-(trifluoromethyl)pyridine-4-carboxamide

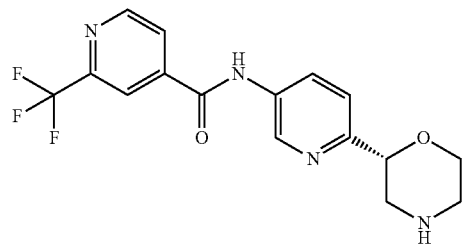

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 2-(trifluoromethyl)pyridine-4-carboxylic acid (CAS: 131747-41-6) instead of 4-chlorobenzoic acid in step (c). White solid. MS (ESI): 353.1 ([M+H]$^+$).

Example 55

N-[6-[(2R)-Morpholin-2-yl]-3-pyridyl]-3-(trifluoromethyl)benzamide

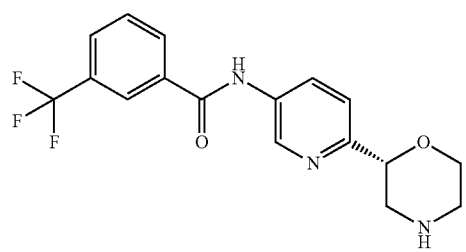 [SMILES: O=C(Nc1ccc([C@H]2CNCCO2)nc1)c1cccc(C(F)(F)F)c1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 3-(trifluoromethyl)benzoic acid (CAS: 454-92-2) instead of 4-chlorobenzoic acid in step (c). White solid. MS (ESI): 352.1 ([M+H]$^+$).

Example 56

N-[6-[(2R)-Morpholin-2-yl]-3-pyridyl]-6-(2,2,2-trifluoroethoxy)pyridine-3-carboxamide

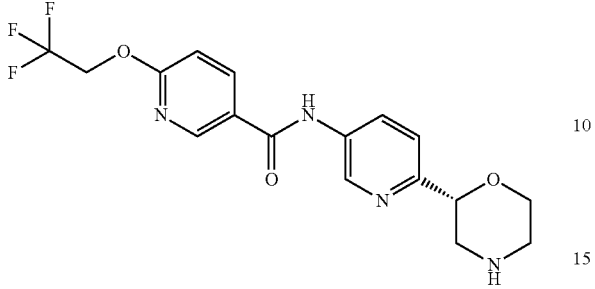

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 6-(2,2,2-trifluoroethoxy)nicotinic acid (CAS: 175204-90-7) instead of 4-chlorobenzoic acid in step (c). Waxy solid. MS (ESI): 383.2 ([M+H]$^+$).

Example 57

2-Ethyl-N-[6-[(2R)-morpholin-2-yl]-3-pyridyl]pyrimidine-5-carboxamide

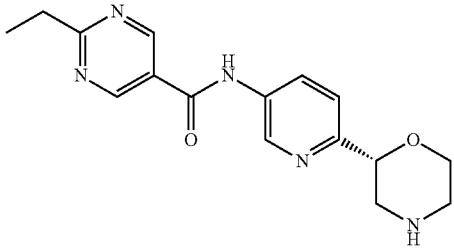 [SMILES: CCc1ncc(C(=O)Nc2ccc([C@H]3CNCCO3)nc2)cn1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 2-ethylpyrimidine-5-carboxylic acid (CAS: 72790-16-0) instead of 4-chlorobenzoic acid in step (c). Waxy solid. MS (ESI): 314.2 ([M+H]$^+$).

Example 58

3-Isopropyl-N-[6-[(2R)-morpholin-2-yl]-3-pyridyl]-1H-pyrazole-5-carboxamide

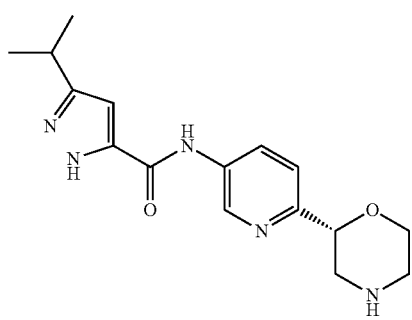 [SMILES: CC(C)C(=N)/C=C(\N)C(=O)Nc1ccc([C@H]2CNCCO2)nc1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 3-isopropylpyrazole-5-carboxylic acid (CAS: 92933-47-6) instead of 4-chlorobenzoic acid in step (c). Waxy solid. MS (ESI): 316.2 ([M+H]$^+$).

Example 59

4-Chloro-N-[6-[(2R)-morpholin-2-yl]-3-pyridyl]-3-propyl-1H-pyrazole-5-carboxamide

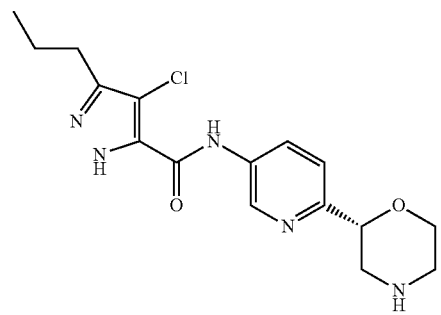 [SMILES: CCCC(=N)/C(Cl)=C(\N)C(=O)Nc1ccc([C@H]2CNCCO2)nc1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 4-chloro-5-propyl-1H-pyrazole-3-carboxylic acid (CAS: 1340578-20-2) instead of 4-chlorobenzoic acid in step (c). White solid. MS (ESI): 352.2 ([{$^{37}$Cl}M+H]$^+$), 350.2 ([{$^{35}$Cl}M+H]$^+$).

Example 60

4-Chloro-3-cyclopropyl-N-[6-[(2R)-morpholin-2-yl]-3-pyridyl]-1H-pyrazole-5-carboxamide

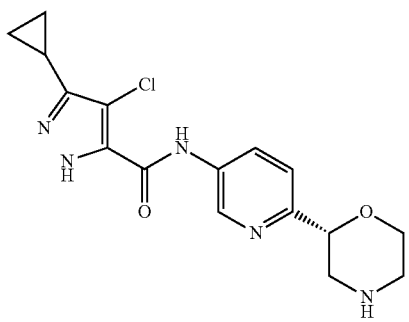 [SMILES: N=C(/C(Cl)=C(\N)C(=O)Nc1ccc([C@H]2CNCCO2)nc1)C1CC1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 4-chloro-3-cyclopropyl-1H-pyrazole-5-carboxylic acid (CAS: 1291275-83-6) instead of 4-chlorobenzoic acid in step (c). White solid. MS (ESI): 350.2 ([{$^{37}$Cl}M+H]$^+$), 348.2 ([{$^{35}$Cl}M+H]$^+$).

Example 61

1-(3-Chlorophenyl)-3-[6-[(2R)-morpholin-2-yl]-3-pyridyl]urea

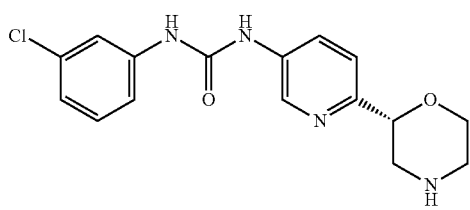 [SMILES: O=C(Nc1ccc([C@H]2CNCCO2)nc1)Nc1cccc(Cl)c1]

The title compound was obtained in analogy to example 8 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a). White solid. MS (ESI): 335.1 ([$^{37}$Cl]M+H]$^+$), 333.2 ([$^{35}$Cl]M+H]$^+$).

Example 62

1-[6-[(2R)-Morpholin-2-yl]-3-pyridyl]-3-[3-(trifluoromethyl)phenyl]urea

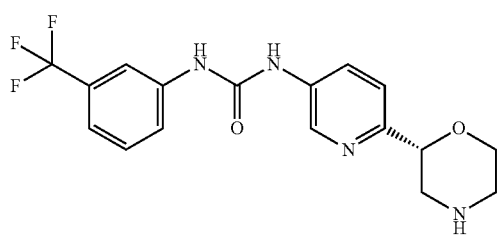 [SMILES: O=C(Nc1ccc([C@H]2CNCCO2)nc1)Nc1cccc(C(F)(F)F)c1]

The title compound was obtained in analogy to example 8 using tert-butyl (2R)-2-(5-bromo-2-pyridyl)morpholine-4-carboxylate instead of (RS)-tert-butyl 2-(5-bromo-2-pyridyl)morpholine-4-carboxylate, and 3-(trifluoromethyl)phenyl isocyanate (CAS: 329-01-1) instead of 3-chlorophenyl isocyanate in step (a). White solid. MS (ESI): 367.1 ([M+H]$^+$).

Example 63

4-Chloro-N-[6-[(2R)-morpholin-2-yl]-3-pyridyl]-3-(trifluoromethyl)-1H-pyrazole-5-carboxamide

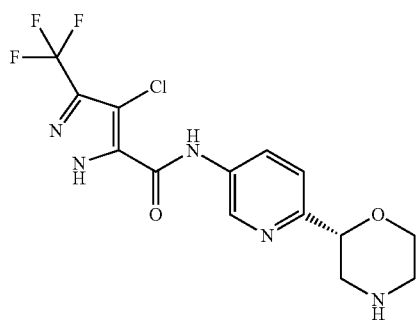 [SMILES: N=C(/C(Cl)=C(\N)C(=O)Nc1ccc([C@H]2CNCCO2)nc1)C(F)(F)F]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 4-chloro-5-(trifluoromethyl)-2H-pyrazole-3-carboxylic acid (CAS: 934758-95-9) instead of 4-chlorobenzoic acid in step (c). White solid. MS (ESI): 378.1 ([$^{37}$Cl]M+H]$^+$), 376.1 ([$^{35}$Cl]M+H]$^+$).

Example 64

4-Chloro-3-methyl-N-[6-[(2R)-morpholin-2-yl]-3-pyridyl]-1H-pyrazole-5-carboxamide

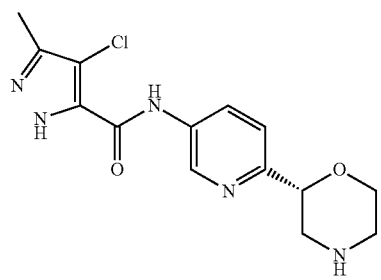 [SMILES: CC(=N)/C(Cl)=C(\N)C(=O)Nc1ccc([C@H]2CNCCO2)nc1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 4-chloro-3-methyl-1H-pyrazole-5-carboxylic acid (CAS: 29400-84-8) instead of 4-chlorobenzoic acid in step (c). White solid. MS (ESI): 324.1 ([$^{37}$Cl]M+H]$^+$), 322.1 ([$^{35}$Cl]M+H]$^+$).

Example 65

4-Methyl-N-[6-[(2R)-morpholin-2-yl]-3-pyridyl]-1H-pyrazole-5-carboxamide

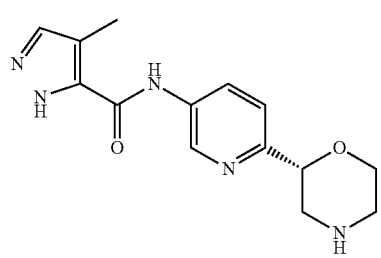 [SMILES: C/C(C=N)=C(/N)C(=O)Nc1ccc([C@H]2CNCCO2)nc1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 4-methyl-1H-pyrazole-3-carboxylic acid (CAS: 82231-51-4) instead of 4-chlorobenzoic acid in step (c). White solid. MS (ESI): 288.2 ([M+H]$^+$).

Example 66

(R)-3-Ethyl-4-methyl-N-(6-(morpholin-2-yl)pyridin-3-yl)-1H-pyrazole-5-carboxamide

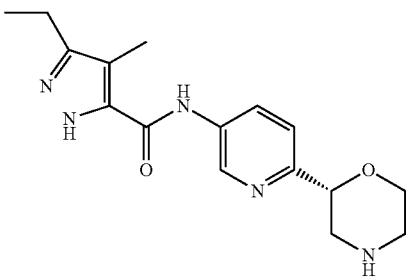 [SMILES: CCC(=N)/C(C)=C(\N)C(=O)Nc1ccc([C@H]2CNCCO2)nc1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 3-ethyl-4-methyl-1H-pyrazole-5-carboxylic acid (CAS: 957129-38-3) instead of 4-chlorobenzoic acid in step (c). White solid. MS (ESI): 316.2 ([M+H]$^+$).

Example 67

(S)-3-Ethyl-4-methyl-N-(6-(morpholin-2-yl)pyridin-3-yl)-1H-pyrazole-5-carboxamide

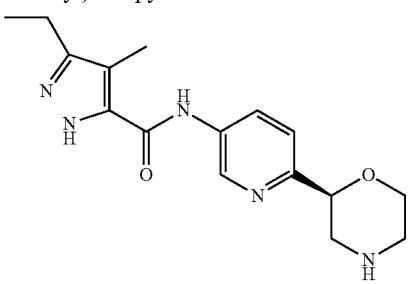

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 3-ethyl-4-methyl-1H-pyrazole-5-carboxylic acid (CAS: 957129-38-3) instead of 4-chlorobenzoic acid in step (c). White solid. MS (ESI): 316.2 ([M+H]$^+$).

Example 68

(R)-6-Methyl-N-(6-(morpholin-2-yl)pyridin-3-yl)-2-(trifluoromethyl)pyrimidine-4-carboxamide

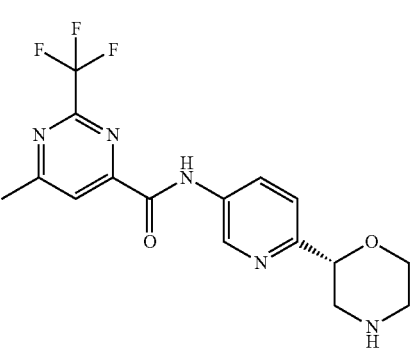 [SMILES: Cc1cc(C(=O)Nc2ccc([C@H]3CNCCO3)nc2)nc(C(F)(F)F)n1]

The title compound was obtained in analogy to example 7 using tert-butyl (2R)-2-(5-bromo-2-pyridyl)morpholine-4-carboxylate instead of (RS)-tert-butyl 2-(5-bromo-2-pyridyl)morpholine-4-carboxylate in step (a), and 6-methyl-2-(trifluoromethyl)pyrimidine-4-carboxylic acid (CAS: 945717-59-9) instead of 4-chlorobenzoic acid in step (c). White solid. MS (ESI): 368.1 ([M+H]$^+$).

Example 69

(S)-6-Methyl-N-(6-(morpholin-2-yl)pyridin-3-yl)-2-(trifluoromethyl)pyrimidine-4-carboxamide

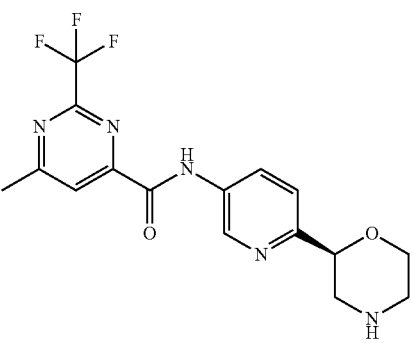 [SMILES: Cc1cc(C(=O)Nc2ccc([C@@H]3CNCCO3)nc2)nc(C(F)(F)F)n1]

The title compound was obtained in analogy to example 7 using tert-butyl (2S)-2-(5-bromo-2-pyridyl)morpholine-4-carboxylate instead of (RS)-tert-butyl 2-(5-bromo-2-pyridyl)morpholine-4-carboxylate in step (a), and 6-methyl-2-(trifluoromethyl)pyrimidine-4-carboxylic acid (CAS: 945717-59-9) instead of 4-chlorobenzoic acid in step (c). White solid. MS (ESI): 368.1 ([M+H]$^+$).

Example 70

(RS)—N-(4-Chlorophenyl)-2-morpholin-2-yl-pyrimidin-5-amine

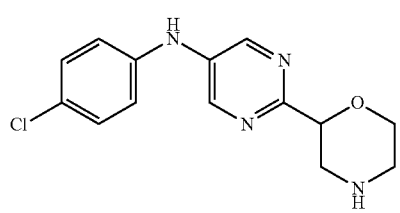

a) 5-Bromopyrimidine-2-carbonyl chloride

To a solution of 5-bromopyrimidine-2-carboxylic acid (10.0 g, CAS: 37131-87-6) in CH$_2$Cl$_2$ (100 mL) was added oxalyl chloride (6.4 g) at room temperature. DMF (0.5 mL) was added. The reaction continued at room temperature for 5 hours. The mixture was filtered. The filtrate was concentrated under reduced pressure and dried further under high vacuum to give crude 5-bromopyrimidine-2-carbonyl chloride (10.9 g, yield: 100%) as a grey solid, which was used for the next step without purification.

b) 2-Bromo-1-(5-bromopyrimidin-2-yl)ethanone

To a solution of 5-bromopyrimidine-2-carbonyl chloride from step (a) (10.9 g, 49.5 mmol) in $CH_3CN$ (200 mL) was added $TMSCHN_2$ in hexane (2 M, 74.3 mL) dropwise at 0° C. under $N_2$ atmosphere. The solution was stirred at room temperature for 16 hours. Then a solution of HBr in AcOH (48%, 20 mL) was added at 0° C. The solution was stirred at room temperature for 3 hours. EtOAc (500 ml) and water (100 ml) was added. The organic layer was washed with brine, dried over $Na_2SO_4$, and concentrated under reduced pressure. The crude product was purified by flash chromatography (silica gel, petroleum ether: EtOAc=30/1~10/1 by vol) to give 2-bromo-1-(5-bromopyrimidin-2-yl)ethanone (13.8 g, yield: 100%) as a yellow oil.

MS (ESI): 282.8 ($\{^{81}Br+^{81}Br\}M+H)^+$, 280.8 ($\{^{79}Br+^{81}Br\}M+H)^+$, 278.8 ($\{^{79}Br+^{79}Br\}M+H)^+$.

c) 2-[Benzyl(2-hydroxyethyl)amino]-1-(5-bromopyrimidin-2-yl)ethanone

To a solution of 2-bromo-1-(5-bromopyrimidin-2-yl)ethanone from step (b) (13.8 g, 49.5 mmol) in $CH_3CN$ (200 mL) were added N-benzylaminoethanol (7.5 g, CAS: 104-63-2) and $K_2CO_3$ (13.7 g). The mixture was stirred at room temperature overnight. The reaction solution was poured into water and extracted with $CH_2Cl_2$ (3×200 mL). The combined organic layers were dried over $Na_2SO_4$ and concentrated under reduced pressure. The crude product was purified by flash chromatography (silica gel, $CH_2Cl_2$: MeOH=200/1~50/1 by vol) to give 2-[benzyl(2-hydroxyethyl)amino]-1-(5-bromopyrimidin-2-yl)ethanone (3.3 g, yield: 18.7% in total from step (a) in three steps) as a yellow oil.

MS (ESI): 349.9 ($\{^{79}Br\}M+H)^+$, 351.9 ($\{^{81}Br\}M+H)^+$.

d) (RS)-2-[Benzyl(2-hydroxyethyl)amino]-1-(5-bromopyrimidin-2-yl)ethanol

To a solution of 2-[benzyl(2-hydroxyethyl)amino]-1-(5-bromopyrimidin-2-yl)ethanone (3.3 g) in MeOH (70 mL) was added $NaBH_4$ (394 mg) at 0° C. The solution was stirred at room temperature for an hour until TLC analysis indicated the consumption of the starting material. The reaction solution was poured into water and was extracted with $CH_2Cl_2$ (2×200 ml). The combined organic layers were dried over $Na_2SO_4$ and concentrated under reduced pressure to give crude (RS)-2-[benzyl(2-hydroxyethyl)amino]-1-(5-bromopyrimidin-2-yl)ethanol (3.5 g, yield: 100%), which was used for the next step without purification.

e) (RS)-4-benzyl-2-(5-bromopyrimidin-2-yl)morpholine

To a solution of (RS)-2-[benzyl(2-hydroxyethyl)amino]-1-(5-bromopyrimidin-2-yl)ethanol (3.5 g, 9.93 mmol, directly from step d) in THF (80 mL) were added $Et_3N$ (1.5 g) and methanesulfonyl chloride (1.14 g) at 0° C. The mixture was stirred at room temperature for 2 hours and then filtered. To the filtrate was added a solution of potassium tert-pentoxide (1.5 g) in THF (20 mL) at 0° C. The mixture was stirred at room temperature for an hour. The reaction solution was poured into EtOAc (500 mL), washed with brine (50 mL), and concentrated under reduced pressure. The crude product was purified flash chromatography (silica gel, $CH_2Cl_2$/MeOH=200/1~50/1 by vol) to give (RS)-4-benzyl-2-(5-bromopyrimidin-2-yl)morpholine (0.5 g, 16% yield from step d in two steps).

MS (ESI): 333.9 ($\{^{79}Br\}M+H)^+$, 335.9 ($\{^{81}Br\}M+H)^+$.

f) (RS)-2-(5-Bromopyrimidin-2-yl)morpholine

To a solution of (RS)-4-benzyl-2-(5-bromopyrimidin-2-yl)morpholine (0.5 g) in $CH_2Cl_2$ (10 mL) was added 2-chloroethyl chloroformate (643 mg, CAS: 627-11-2). Then the solution was stirred at refluxing temperature for 4 hours until TLC indicated the consumption of the starting material. Volatiles were removed under reduced pressure. The residue was dissolved in methanol (10 mL) and stirred at refluxing temperature for an hour. The reaction solution was concentrated under reduced pressure. Further drying under high vacuum gave crude (RS)-2-(5-bromopyrimidin-2-yl)morpholine (365 mg, yield: 100%), which was used for the next step without purification.

g) (RS)-tert-Butyl 2-(5-bromopyrimidin-2-yl)morpholine-4-carboxylate

To a solution of (RS)-2-(5-bromopyrimidin-2-yl)morpholine (365 mg, 1.5 mmol) from step (f) and $K_2CO_3$ (414 mg) in a mixture of THF (10 mL) and water (5 mL) was added di-tert-butyl dicarbonate (486 mg, CAS: 24424-99-5) at room temperature. The reaction continued overnight. The mixture was extracted with $CH_2Cl_2$ (2×50 mL). The combined organic layers were washed with brine (20 mL), dried over $Na_2SO_4$, and concentrated under reduced pressure. Purification by flash chromatography (silica gel, $CH_2Cl_2$/MeOH=200/1~50/1 by vol) gave (RS)-tert-butyl 2-(5-bromopyrimidin-2-yl)morpholine-4-carboxylate (300 mg, 58% yield) as a yellow oil.

MS (ESI): 366.0 ($\{^{79}Br\}M+Na)^+$, 368.0 ($\{^{81}Br\}M+Na)^+$, 287.8 ($\{^{79}Br\}M-C_4H_8+H)^+$, 289.8 ($\{^{81}Br\}M-C_4H_8+H)^+$.

h) (RS)—N-(4-Chlorophenyl)-2-morpholin-2-yl-pyrimidin-5-amine

To a solution of (RS)-tert-butyl 2-(5-bromopyrimidin-2-yl)morpholine-4-carboxylate (30 mg) and 4-chloroaniline (11 mg, CAS: 106-47-8) in dioxane (1 mL) were added 4,5-bis(diphenylphosphino)-9,9-dimethylxanthene (Xantphos, 15 mg, CAS: 161265-03-8), $Cs_2CO_3$ (85 mg, CAS: 534-17-8), and tris(dibenzylidineacetone)dipalladium(0) (8 mg, CAS: 51364-51-3). The reaction proceeded at 90° C. under $N_2$ atmosphere overnight. The solution was diluted with $CH_2Cl_2$ (10 mL), washed with brine (20 mL), dried over $Na_2SO_4$, and concentrated under reduced pressure. The residue was dissolved in the mixture of $CH_2Cl_2$ (1 mL) and TFA (1 mL). The solution was stirred at room temperature for 3 hours. Volatiles were removed under reduced pressure. The residue was purified by Prep-HPLC (mobile phase A: $H_2O$, B: $CH_3CN$ with 0.1% TFA, C18 column) to give (RS)—N-(4-chlorophenyl)-2-morpholin-2-yl-pyrimidin-5-amine (10 mg, 40% yield in two steps) as a white solid.

$^1H$ NMR (400 MHz, Methanol-$d^4$): δ 8.54 (2H), 7.33 (2H), 7.17 (2H), 4.9 (1H), 4.1 (1H), 3.97 (1H), 3.63 (1H), 3.51 (1H), 3.35~3.23 (2H).

MS (ESI): 290.9 ($\{^{35}Cl\}M+H)^+$, 292.9 ($\{^{37}Cl\}M+H)^+$.

Example 71

(RS)-2-Morpholin-2-yl-N-[4-(trifluoromethyl)phenyl]pyrimidin-5-amine

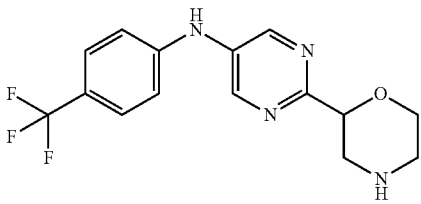 [SMILES: FC(F)(F)c1ccc(Nc2cnc(C3CNCCO3)nc2)cc1]

The title compound was obtained in analogy to example 70 using 4-(trifluoromethyl)aniline (CAS: 455-14-1) instead of 4-chloroaniline in step (h). White solid. MS (ESI): 325.0 ([M+H]$^+$).

Example 72

(RS)-4-Chloro-N-(2-morpholin-2-ylpyrimidin-5-yl)benzamide

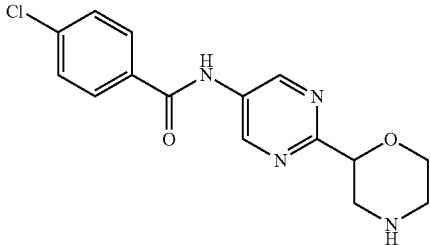 [SMILES: O=C(Nc1cnc(C2CNCCO2)nc1)c1ccc(Cl)cc1]

a) (RS)-tert-Butyl 2-[5-(benzhydrylideneamino)pyrimidin-2-yl]morpholine-4-carboxylate To a solution of (RS)-tert-butyl 2-(5-bromopyrimidin-2-yl)morpholine-4-carboxylate (230 mg) and benzophenone imine (127 mg, CAS: 1013-88-3) in dioxane (10 mL) were added 4,5-bis(diphenylphosphino)-9,9-dimethylxanthene (Xantphos, 116 mg, CAS: 161265-03-8), tris(dibenzylideneacetone)dipalladium(0) (61.3 mg, CAS: 51364-51-3), and Cs$_2$CO$_3$ (653 mg, CAS: 534-17-8). The reaction proceeded at 90° C. under N$_2$ atmosphere overnight. The solution was poured into water (100 mL) and extracted with CH$_2$Cl$_2$ (2×150 mL). The combined organic layers were dried over Na$_2$SO$_4$ and concentrated under reduced pressure to give crude (RS)-tert-butyl 2-[5-(benzhydrylideneamino)pyrimidin-2-yl]morpholine-4-carboxylate (297 mg, yield: 100%), which was used for the next step without purification.

b) (RS)-tert-Butyl 2-(5-aminopyrimidin-2-yl)morpholine-4-carboxylate

To a solution of (RS)-tert-butyl 2-[5-(benzhydrylideneamino)pyrimidin-2-yl]morpholine-4-carboxylate (297 mg, 0.668 mmol) in MeOH (10 mL) were added sodium acetate (274 mg, CAS: 127-09-3) and hydroxylamine hydrochloride (69.6 mg, CAS: 5470-11-1). The mixture was stirred at room temperature for 2 hours until TLC analysis indicated complete consumption of the starting material. The solution was poured into water (50 mL), extracted with CH$_2$Cl$_2$ (2×100 mL). The combined organic layers were dried over Na$_2$SO$_4$, concentrated under reduced pressure, and purified by flash chromatography (silica gel, CH$_2$Cl$_2$/MeOH=100/1~50/1 by vol) to give (RS)-tert-butyl 2-(5-aminopyrimidin-2-yl)morpholine-4-carboxylate (100 mg, yield: 55.6%) as a yellow solid.

MS (ESI): 281.2 (M+H)$^+$.

c) (RS)-4-Chloro-N-(2-morpholin-2-ylpyrimidin-5-yl)benzamide

To a solution of 4-chlorobenzoic acid (16.7 mg, CAS: 74-11-3) in DMF (1 mL) were added HATU (40.3 mg, CAS: CAS: 148893-10-1) and DIPEA (37.2 mg, CAS: 7087-68-5). The mixture was stirred at room temperature for 30 minutes. (RS)-tert-Butyl 2-(5-aminopyrimidin-2-yl)morpholine-4-carboxylate (27 mg) was added. The reaction continued at room temperature overnight. Then the solution was diluted with CH$_2$Cl$_2$ (10 mL), washed with brine (20 mL), dried over Na$_2$SO$_4$, and concentrated under reduced pressure. The residue was dissolved in a mixture of CH$_2$Cl$_2$ (1 mL) and trifluoroacetic acid (TFA, 1 mL, CAS: 76-05-1). The solution was stirred at room temperature for 2 hours. Volatiles were removed under reduced pressure. The residue was purified by Prep-HPLC (mobile phase A: H$_2$O, B: CH$_3$CN with 0.1% TFA, C18 column) to give (RS)-4-chloro-N-(2-morpholin-2-ylpyrimidin-5-yl)benzamide (8 mg, 26% yield in two steps) as a white solid.

$^1$H NMR (400 MHz, Methanol-d$^4$): δ 9.24 (2H), 7.98 (2H), 7.57 (2H), 4.97 (1H), 4.21 (1H), 4.02 (1H), 3.73 (1H), 3.54 (1H), 3.73~3.30 (2H).

MS (ESI): 319.0 ({$^{35}$Cl}M+H)$^+$, 321.0 ({$^{37}$Cl}M+H)$^+$.

Example 73

(RS)-1-(3-Chlorophenyl)-3-(2-morpholin-2-ylpyrimidin-5-yl)urea

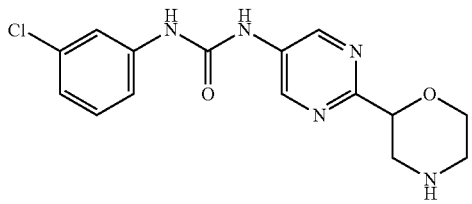 [SMILES: O=C(Nc1cnc(C2CNCCO2)nc1)Nc1cccc(Cl)c1]

To a solution of (RS)-tert-butyl 2-(5-aminopyrimidin-2-yl)morpholine-4-carboxylate (27 mg) in CH$_2$Cl$_2$ (1 mL) were added Et$_3$N (19.4 mg, CAS: 121-44-8) and 3-chlorophenyl isocyanate (14.7 mg, CAS: 2909-38-8). The reaction proceeded at room temperature for overnight. The solution was diluted with CH$_2$Cl$_2$ (10 mL), washed with citric acid aqueous solution (2×20 mL) and brine (20 mL), dried over Na$_2$SO$_4$, and concentrated under reduced pressure. The residue was dissolved in the mixture of CH$_2$Cl$_2$ (1 mL) and trifluoroacetic acid (TFA, 1 mL, CAS: 76-05-1). The solution was stirred at room temperature for 2 hours. Volatiles were removed under reduced pressure. The residue was purified by Prep-HPLC (mobile phase A: H$_2$O, B: CH$_3$CN with 0.1% TFA, C18 column) to give the title compound (7 mg, 22% yield in two steps) as a white solid.

¹H NMR (400 MHz, Methanol-d⁴): δ 9.00 (2H), 7.67 (1H), 7.32~7.26 (2H), 7.05 (1H), 4.95 (1H), 4.18 (1H), 4.01 (1H), 3.67 (1H), 3.53 (1H), 3.36~3.30 (2H).
MS (ESI): 334.1 ({³⁵Cl}M+H)⁺, 336.1 ({³⁷Cl}M+H)⁺.

Example 74

(RS)-4-Chloro-3-ethoxy-N-(6-morpholin-2-yl-3-pyridyl)-1H-pyrazole-5-carboxamide

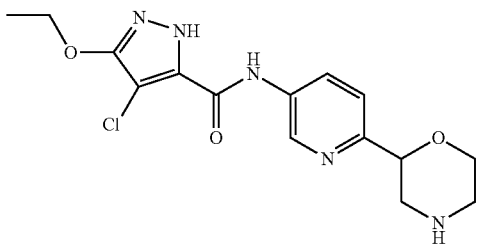 [SMILES: CCOc1n[nH]c(C(=O)Nc2ccc(C3CNCCO3)nc2)c1Cl]

a) Methyl 5-hydroxy-1H-pyrazole-3-carboxylate

To the solution of hydrazine monohydrate (3.85 g, 0.077 mol, CAS: 7803-57-8) in toluene (30 mL) was added acetic acid (15 mL) and dimethyl acetylenedicarboxylate (10 g, 0.07 mol, CAS: 762-42-5) was added. The solution was stirred at room temperature for 3 hours. Then the mixture was poured into iced water. The precipitate was collected by filtration and washed with cold water. Further drying under high vacuum gave methyl 5-hydroxy-1H-pyrazole-3-carboxylate (7.5 g, 75% yield) as a white solid.
¹H NMR (400 MHz, DMSO-d⁶): δ 12.81 (s, 1H), 10.04 (br, 1H), 5.96 (br, 1H), 3.77 (s, 3H).

b) Methyl 5-ethoxy-1H-pyrazole-3-carboxylate

To the solution of methyl 5-hydroxy-1H-pyrazole-3-carboxylate (4 g, 28.17 mmol) in DMF (25 mL) was added K₂CO₃ (5.83 g, 42.2 mmol) and iodoethane (4.8 g, 31 mmol). The solution was stirred at room temperature for 15 hrs. Then the mixture was poured into iced water. The mixture was extracted with ethyl acetate (100 mL). The organic layer was washed with brine (30 mL), dried over Na₂SO₄, and concentrated under reduced pressure. Recrystallization from dichloromethane (10 ml) gave methyl 5-ethoxy-1H-pyrazole-3-carboxylate (2.2 g, 46% yield) as a white solid.
¹H NMR (400 MHz, DMSO-d⁶): δ 13.13 (s, 1H), 6.23 (s, 1H), 4.11 (d, 2H), 3.81 (s, 3H), 1.28 (m, 3H).

c) Methyl 4-chloro-5-ethoxy-1H-pyrazole-3-carboxylate

To the solution of methyl 5-ethoxy-1H-pyrazole-3-carboxylate (2.2 g, 12.94 mmol) in DMF (40 mL) was added N-chlorosuccinimide (2.06 g, 15.53 mmol, CAS: 128-09-6) at 0° C. Then the mixture was warmed to 50° C. Stirring was continued for 15 hours. The reaction solution was concentrated under reduced pressure to remove about 50% amount of DMF. Then the solution was poured into iced water. The precipitate was collected by filtration and washed by cold water. Further drying under high vacuum gave methyl 4-chloro-5-ethoxy-1H-pyrazole-3-carboxylate (1.65 g, 63% yield) as a white solid.
¹H NMR (400 MHz, DMSO-d⁶): δ 13.44 (br, 1H), 4.24 (d, 2H), 3.85 (s, 3H), 1.32 (t, 3H).

d) 4-Chloro-5-ethoxy-1H-pyrazole-3-carboxylic acid

To the solution of methyl 4-chloro-5-ethoxy-1H-pyrazole-3-carboxylate (1.65 g, 8.06 mmol) in THF (30 mL) was added 1M aqueous NaOH solution (16.1 mL, 16.1 mmol) at 0° C. Then the solution was refluxed for 3 hours. The reaction mixture was cooled to room temperature and poured into water. The pH was adjusted to ~1 with concentrated HCl. The precipitate was collected by filtration and washed with cold water. Further drying under high vacuum gave 4-chloro-5-ethoxy-1H-pyrazole-3-carboxylic acid (1.4 g, 91.5% yield) as a white solid.
¹H NMR (400 MHz, DMSO-d⁶): δ 13.25 (s, 1H), 4.23 (d, 2H), 1.32 (t, 3H).

e) (RS)-4-Chloro-3-ethoxy-N-(6-morpholin-2-yl-3-pyridyl)-1H-pyrazole-5-carboxamide The title compound was obtained in analogy to example 7 using 4-chloro-5-ethoxy-1H-pyrazole-3-carboxylic acid instead of 4-chlorobenzoic acid in step (c). White solid.
¹H NMR (400 MHz, Methanol-d⁴): δ 8.91 (d, 1H), 8.26 (dd, 1H), 7.62 (d, 1H), 4.90 (s, 1H), 4.33 (m, 2H), 4.25 (m, 1H), 4.04 (m, 1H), 3.70 (d, 1H), 3.36 (d, 1H), 3.29 (m, 2H), 1.43 (t, 3H).
MS (ESI): 352.1 ({³⁵Cl}M+H)⁺, 354.1 ({³⁷Cl}M+H)⁺.

Example 75

(RS)-4-Chloro-N-(6-morpholin-2-yl-3-pyridyl)-3-(2,2,2-trifluoroethoxy)-1H-pyrazole-5-carboxamide

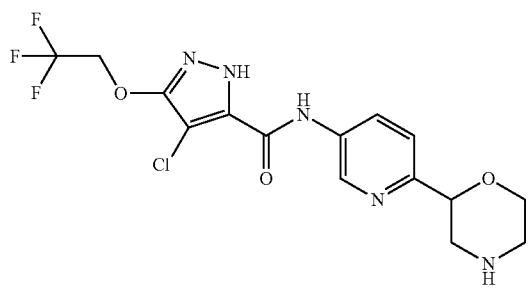 [SMILES: O=C(Nc1ccc(C2CNCCO2)nc1)c1[nH]nc(OCC(F)(F)F)c1Cl]

a) Methyl 5-(2,2,2-trifluoroethoxy)-1H-pyrazole-3-carboxylate

To a solution of methyl 5-hydroxy-1H-pyrazole-3-carboxylate (10 g, 70.4 mmol), Cs₂CO₃ (25 g, 77.5 mmol) in DMF (100 ml) was added 2,2,2-trifluoroethyl trifluoromethanesulfonate (16.3 g, 70.4 mmol, CAS: 6226-25-1) in portions. The solution was stirred at room temperature overnight. The reaction mixture was poured into 500 ml icewater carefully. The precipitate was collected by filtration and washed with cooled water. Further drying under high vacuum gave methyl 5-(2,2,2-trifluoroethoxy)-1H-pyrazole-3-carboxylate (12 g, 76% yield) as a white solid.
¹H NMR (400 MHz, DMSO-d⁶): δ 13.41 (s, 1H), 6.43 (s, 1H), 4.86 (m, 2H), 3.84 (s, 3H)
MS (ESI): 225.1 ([M+H]⁺).

b) Methyl 4-chloro-5-(2,2,2-trifluoroethoxy)-1H-pyrazole-3-carboxylate

To the solution of methyl 5-(2,2,2-trifluoroethoxy)-1H-pyrazole-3-carboxylate (1.9 g, 8.47 mmol) in DMF (30 mL) was added N-chlorosuccinimide (1.35 g, 10.17 mmol) at 0° C. Then the solution was stirred at 50° C. for 15 hours. The reaction solution was concentrated under vacuum to remove 50% of DMF. Then the solution was poured into water. The precipitate was collected by filtration, washed with water, and dried under high vacuum to give methyl 4-chloro-5-(2,2,2-trifluoroethoxy)-1H-pyrazole-3-carboxylate (1.9 g, 87% yield) as a white solid.

c) 4-Chloro-5-(2,2,2-trifluoroethoxy)-1H-pyrazole-3-carboxylic acid

To the solution of methyl 4-chloro-5-(2,2,2-trifluoroethoxy)-1H-pyrazole-3-carboxylate (1.9 g, 7.35 mmol) in a mixture of THF (15 mL) and MeOH (15 mL) was added 1M aqueous NaOH (14.7 mL, 14.7 mmol) at 0° C. Then the solution was stirring at refluxing temperature for 3 hours. The reaction solution was poured into water. The pH was adjusted to about 1 with concentrated HCl solution. The precipitate was collected by filtration, washed with water, and dried under high vacuum to give 4-chloro-5-(2,2,2-trifluoroethoxy)-1H-pyrazole-3-carboxylic acid (1.5 g, 83% yield) as a white solid.
$^1$H NMR (400 MHz, DMSO-d$^6$): δ 13.91 (br, 1H), 13.56 (s, 1H), 4.91 (m, 2H).
MS (ESI): 245.0 ($\{^{35}Cl\}$M+H)$^+$, 247.0 ($\{^{37}Cl\}$M+H)$^+$.

d) (RS)-4-chloro-N-(6-morpholin-2-yl-3-pyridyl)-3-(2,2,2-trifluoroethoxy)-1H-pyrazole-5-carboxamide The title compound was obtained in analogy to example 7 using 4-chloro-5-(2,2,2-trifluoroethoxy)-1H-pyrazole-3-carboxylic acid instead of 4-chlorobenzoic acid in step (c). White solid.
$^1$H NMR (400 MHz, Methanol-d$^4$): δ 8.90 (d, 1H), 8.26 (dd, 1H), 7.63 (d, 1H), 4.91 (s, 1H), 4.81 (m, 2H), 4.25 (d, 1H), 4.03 (m, 1H), 3.70 (d, 1H), 3.36 (d, 1H), 3.29 (m, 2H).
MS (ESI): 406.1 ($\{^{35}Cl\}$M+H)$^+$, 408.1 ($\{^{37}Cl\}$M+H)$^+$.

Example 76

4-Chloro-3-ethyl-N-[6-[(2S)-morpholin-2-yl]-3-pyridyl]-1H-pyrazole-5-carboxamide

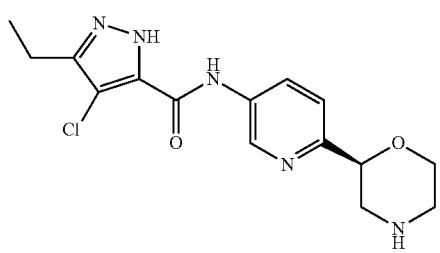 [SMILES: CCc1n[nH]c(C(=O)Nc2ccc([C@@H]3CNCCO3)nc2)c1Cl]

The title compound was obtained in analogy to example 67 using 4-chloro-3-ethyl-1H-pyrazole-5-carboxylic acid (CAS: 158668-22-5) instead of 3-ethyl-4-methyl-1H-pyrazole-5-carboxylic acid. White solid.
MS (ESI): 336.0 ($\{^{35}Cl\}$M+H)$^+$, 338.0 ($\{^{37}Cl\}$M+H)$^+$.

Example 77

3-Ethyl-4-fluoro-N-[6-[(2S)-morpholin-2-yl]-3-pyridyl]-1H-pyrazole-5-carboxamide

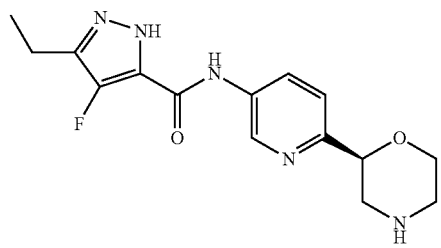 [SMILES: CCc1n[nH]c(C(=O)Nc2ccc([C@@H]3CNCCO3)nc2)c1F]

The title compound was obtained in analogy to example 67 using 5-ethyl-4-fluoro-1H-pyrazole-3-carboxylic acid (CAS: 681034-63-9) instead of 3-ethyl-4-methyl-1H-pyrazole-5-carboxylic acid. White solid.
MS (ESI): 320.0 (M+H)$^+$.

Example 78

4-Bromo-3-ethyl-N-[6-[(2S)-morpholin-2-yl]-3-pyridyl]-1H-pyrazole-5-carboxamide

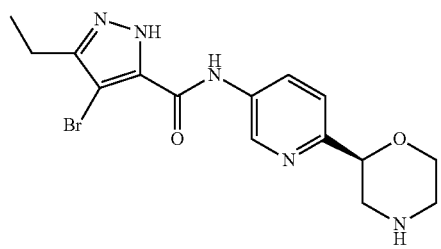 [SMILES: CCc1n[nH]c(C(=O)Nc2ccc([C@@H]3CNCCO3)nc2)c1Br]

The title compound was obtained in analogy to example 67 using 4-bromo-5-ethyl-1H-pyrazole-3-carboxylic acid (CAS: 1291177-22-4) instead of 3-ethyl-4-methyl-1H-pyrazole-5-carboxylic acid. Waxy solid.
MS (ESI): 381.9 ($[\{^{81}Br\}M+H]^+$), 379.9 ($[\{^{79}Br\}M+H]^+$).

Example 79

4-Fluoro-N-[6-[(2S)-morpholin-2-yl]-3-pyridyl]-3-propyl-1H-pyrazole-5-carboxamide

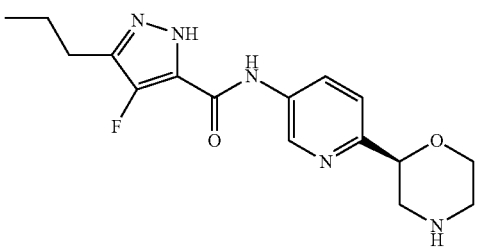 [SMILES: CCCc1n[nH]c(C(=O)Nc2ccc([C@@H]3CNCCO3)nc2)c1F]

The title compound was obtained in analogy to example 67 using 4-fluoro-5-propyl-1H-pyrazole-3-carboxylic acid (CAS: 681034-64-0), instead of 3-ethyl-4-methyl-1H-pyrazole-5-carboxylic acid. White solid.
MS (ESI): 334.0 (M+H)+.

Example 80

3-Cyclopropyl-4-fluoro-N-[6-[(2S)-morpholin-2-yl]-3-pyridyl]-1H-pyrazole-5-carboxamide

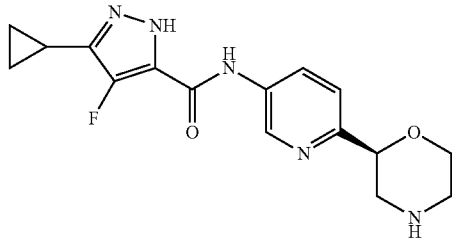 [SMILES: O=C(Nc1ccc([C@@H]2CNCCO2)nc1)c1[nH]nc(C2CC2)c1F]

The title compound was obtained in analogy to example 67 using 5-cyclopropyl-4-fluoro-1H-pyrazole-3-carboxylic acid (CAS: 681034-74-2) instead of 3-ethyl-4-methyl-1H-pyrazole-5-carboxylic acid. Waxy solid.
MS (ESI): 332.0 (M+H)+.

Example 81

4-Bromo-3-cyclopropyl-N-[6-[(2S)-morpholin-2-yl]-3-pyridyl]-1H-pyrazole-5-carboxamide

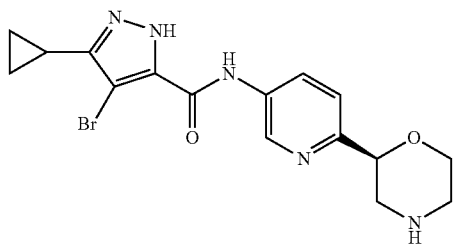 [SMILES: O=C(Nc1ccc([C@@H]2CNCCO2)nc1)c1[nH]nc(C2CC2)c1Br]

The title compound was obtained in analogy to example 67 using 4-bromo-5-cyclopropyl-2H-pyrazole-3-carboxylic acid (CAS: 1290764-98-5) instead of 3-ethyl-4-methyl-1H-pyrazole-5-carboxylic acid. White solid.
MS (ESI): 394.0 ([{81Br}M+H]+), 392.0 ([{79Br}M+H]+).

Example 82

4-Chloro-3-ethyl-N-[6-[(2R)-morpholin-2-yl]-3-pyridyl]-1H-pyrazole-5-carboxamide

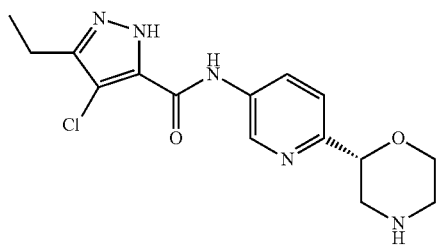 [SMILES: CCc1n[nH]c(C(=O)Nc2ccc([C@H]3CNCCO3)nc2)c1Cl]

The title compound was obtained in analogy to example 66 using 4-chloro-3-ethyl-1H-pyrazole-5-carboxylic acid (CAS: 158668-22-5) instead of 3-ethyl-4-methyl-1H-pyrazole-5-carboxylic acid. White solid.
MS (ESI): 336.1 ({35Cl}M+H)+, 338.1 ({37Cl}M+H)+.

Example 83

3-Ethyl-4-fluoro-N-[6-[(2R)-morpholin-2-yl]-3-pyridyl]-1H-pyrazole-5-carboxamide

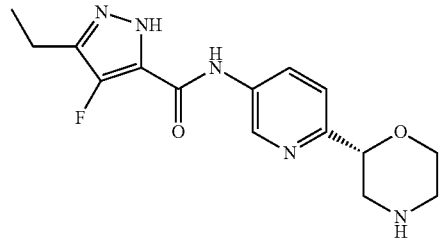 [SMILES: CCc1n[nH]c(C(=O)Nc2ccc([C@H]3CNCCO3)nc2)c1F]

The title compound was obtained in analogy to example 66 using 5-ethyl-4-fluoro-1H-pyrazole-3-carboxylic acid (CAS: 681034-63-9) instead of 3-ethyl-4-methyl-1H-pyrazole-5-carboxylic acid. White solid.
MS (ESI): 320.2 (M+H)+.

Example 84

4-Bromo-3-ethyl-N-[6-[(2R)-morpholin-2-yl]-3-pyridyl]-1H-pyrazole-5-carboxamide

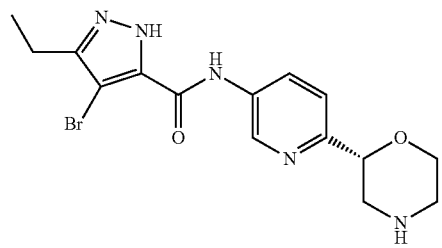 [SMILES: CCc1n[nH]c(C(=O)Nc2ccc([C@H]3CNCCO3)nc2)c1Br]

The title compound was obtained in analogy to example 66 using 4-bromo-5-ethyl-1H-pyrazole-3-carboxylic acid (CAS: 1291177-22-4) instead of 3-ethyl-4-methyl-1H-pyrazole-5-carboxylic acid. White solid.
MS (ESI): 382.1 ([{81Br}M+H]+), 380.1 ([{79Br}M+H]+).

Example 85

4-Fluoro-N-[6-[(2R)-morpholin-2-yl]-3-pyridyl]-3-propyl-1H-pyrazole-5-carboxamide

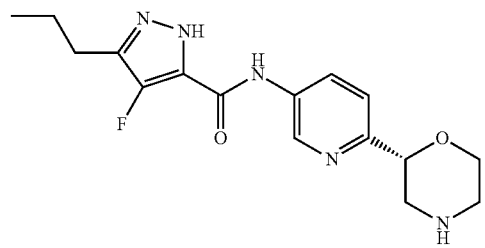

The title compound was obtained in analogy to example 66 using 4-fluoro-5-propyl-1H-pyrazole-3-carboxylic acid (CAS: 681034-64-0), instead of 3-ethyl-4-methyl-1H-pyrazole-5-carboxylic acid. White solid.
MS (ESI): 334.2 (M+H)+.

Example 86

3-Cyclopropyl-4-fluoro-N-[6-[(2R)-morpholin-2-yl]-3-pyridyl]-1H-pyrazole-5-carboxamide

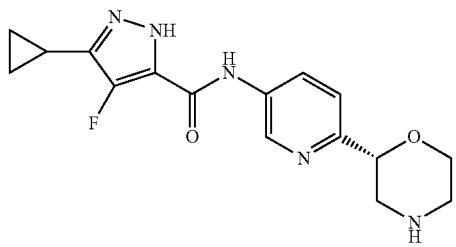 [SMILES: O=C(Nc1ccc([C@H]2CNCCO2)nc1)c1[nH]nc(C2CC2)c1F]

The title compound was obtained in analogy to example 66 using 5-cyclopropyl-4-fluoro-1H-pyrazole-3-carboxylic acid (CAS: 681034-74-2) instead of 3-ethyl-4-methyl-1H-pyrazole-5-carboxylic acid. Waxy solid.
MS (ESI): 332.2 (M+H)+.

Example 87

4-Bromo-3-cyclopropyl-N-[6-[(2R)-morpholin-2-yl]-3-pyridyl]-1H-pyrazole-5-carboxamide

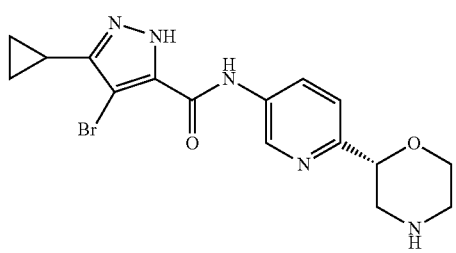 [SMILES: O=C(Nc1ccc([C@H]2CNCCO2)nc1)c1[nH]nc(C2CC2)c1Br]

The title compound was obtained in analogy to example 66 using 4-bromo-5-cyclopropyl-2H-pyrazole-3-carboxylic acid (CAS: 1290764-98-5) instead of 3-ethyl-4-methyl-1H-pyrazole-5-carboxylic acid. White solid.
MS (ESI): 394.0 ([{$^{81}$Br}M+H]+), 392.0 ([{$^{79}$Br}M+H]+).

Example 88

3-Isobutyl-N-[6-[(2S)-morpholin-2-yl]-3-pyridyl]-1H-pyrazole-5-carboxamide

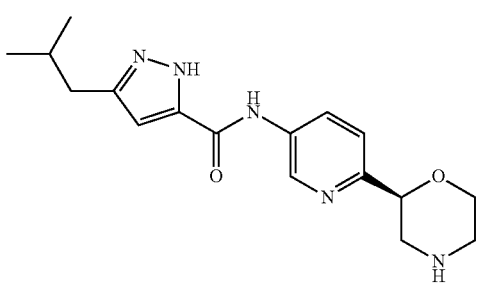 [SMILES: CC(C)Cc1cc(C(=O)Nc2ccc([C@@H]3CNCCO3)nc2)[nH]n1]

The title compound was obtained in analogy to example 67 using 3-isobutyl-1H-pyrazole-5-carboxylic acid (CAS: 92933-49-8) instead of 3-ethyl-4-methyl-1H-pyrazole-5-carboxylic acid. White solid.
MS (ESI): 330.2 (M+H)+.

Example 89

4-Fluoro-3-isobutyl-N-[6-[(2S)-morpholin-2-yl]-3-pyridyl]-1H-pyrazole-5-carboxamide

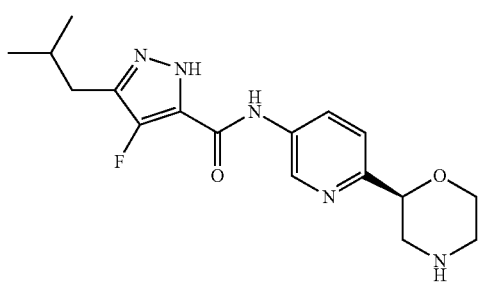 [SMILES: CC(C)Cc1n[nH]c(C(=O)Nc2ccc([C@@H]3CNCCO3)nc2)c1F]

a) Ethyl 6-methyl-2,4-dioxo-heptanoate

To a solution of sodium ethoxide (7 g, 0.1 mol) in anhydrous ethanol (150 mL) was added diethyl oxalate (15 g, 0.1 mol, CAS: 95-92-1) at 0° C. 4-Methyl-2-pentanone (10 g, 0.1 mol, CAS: 108-10-1) was added in portions afterwards. The mixture was stirred at 50° C. for 20 hours. The solution was cooled to room temperature and used in the next step directly.

b) Ethyl 5-isobutyl-1H-pyrazole-3-carboxylate

To the solution of ethyl 6-methyl-2,4-dioxo-heptanoate (0.1 mol) in ethanol (150 mL) from step (a) was added acetic acid (9 g, 0.15 mol) and hydrazine monohydrate (8.1 g, 0.15 mol, CAS: 7803-57-8). The reaction mixture was stirred for 12 hours. Then the reaction solution was concentrated under reduced pressure, diluted with water, and extracted twice with ethyl acetate (2×300 mL). The combined organic layers were washed with brine (50 mL), dried over Na$_2$SO$_4$, filtered through thin silica pad, and concentrated under reduced pressure. The crude product was purified by silica gel chromatography to give ethyl 5-isobutyl-1H-pyrazole-3-carboxylate as a white solid (13 g, 68% yield).
MS (ESI): 197.2 (M+H)+.

c) Ethyl 4-fluoro-5-isobutyl-1H-pyrazole-3-carboxylate

To a solution of ethyl 5-isobutyl-1H-pyrazole-3-carboxylate (5.0 g, 25.5 mmol) in CH$_3$CN (300 mL) was added Selectfluor® (18.0 g, 51.0 mmol, CAS: 140681-55-6) at 0° C. Then the solution was heated to 70° C. Stirring was continued for 15 hours. The reaction solution was cooled to room temperature and concentrated under reduced pressure. The residue was diluted with aqueous HCl (3N, 200 mL) and extracted with dichloromethane (100 mL×2). The combined organic layers were washed with brine (20 mL), dried over Na$_2$SO$_4$, and concentrated under reduced pressure. Purification through silica gel column chromatography (dichloromethane/MeOH=200/1~100/1 by volume) gave ethyl 4-fluoro-5-isobutyl-1H-pyrazole-3-carboxylate (1.4 g, 26% of yield) as a yellow oil.

$^1$H NMR (400 MHz, DMSO-d$^6$): δ 4.42 (q, 2H), 2.55 (d, 2H), 2.00 (m, 1H), 1.40 (t, 3H), 0.96 (d, 6H).

MS (ESI): 215.1 (M+H)$^+$.

d) 4-Fluoro-5-isobutyl-1H-pyrazole-3-carboxylic acid

To a solution of 4-fluoro-5-isobutyl-1H-pyrazole-3-carboxylic acid (1.4 g, 6.54 mmol) in THF/MeOH (V/V=1:1, 20 mL) was added 1M aq NaOH (13.1 mL, 13.1 mmol) at 0° C. Then the solution was refluxed for 3 hours. The reaction solution was poured into water. The pH was adjusted to about 1 with concentrated HCl. The mixture was extracted with ethyl acetate (100 mL×2). The combined organic layers were washed with brine (20 mL), concentrated under reduced pressure and recrystallized from ethyl acetate (30 mL) to give 4-fluoro-5-isobutyl-1H-pyrazole-3-carboxylic acid (1.2 g, 99% yield) as a yellow solid.

$^1$H NMR (400 MHz, DMSO-d$^6$): δ 2.44 (d, 2H), 1.90 (m, 1H), 0.87 (d, 6H).

MS (ESI): 187.1 (M+H)$^+$.

e) 4-Fluoro-3-isobutyl-N-[6-[(2S)-morpholin-2-yl]-3-pyridyl]-1H-pyrazole-5-carboxamide The title compound was obtained in analogy to example 67 using 4-fluoro-5-isobutyl-1H-pyrazole-3-carboxylic acid instead of 3-ethyl-4-methyl-1H-pyrazole-5-carboxylic acid. Waxy solid.

MS (ESI): 348.2 (M+H)$^+$.

Example 90

3-Butyl-4-fluoro-N-[6-[(2S)-morpholin-2-yl]-3-pyridyl]-1H-pyrazole-5-carboxamide

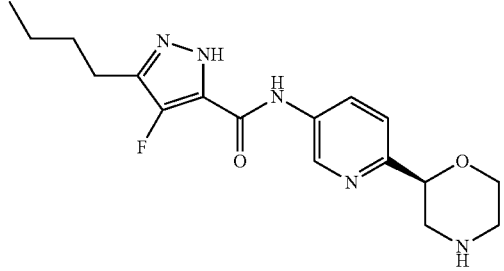 [SMILES: CCCCc1n[nH]c(C(=O)Nc2ccc([C@@H]3CNCCO3)nc2)c1F]

The title compound was obtained in analogy to example 67 using 5-butyl-4-fluoro-1H-pyrazole-3-carboxylic acid (CAS: 681034-65-1) instead of 3-ethyl-4-methyl-1H-pyrazole-5-carboxylic acid. Waxy solid.

MS (ESI): 348.2 (M+H)$^+$.

Example 91

3-Butyl-N-[6-[(2S)-morpholin-2-yl]-3-pyridyl]-1H-pyrazole-5-carboxamide

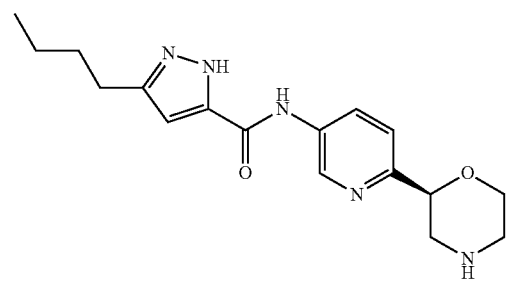 [SMILES: CCCCc1cc(C(=O)Nc2ccc([C@@H]3CNCCO3)nc2)[nH]n1]

The title compound was obtained in analogy to example 67 using 5-butyl-1H-pyrazole-3-carboxylic acid (CAS: 92933-48-7) instead of 3-ethyl-4-methyl-1H-pyrazole-5-carboxylic acid. Waxy solid.

MS (ESI): 330.2 (M+H)$^+$.

Example 92

5-Isopropyl-N-[6-[(2S)-morpholin-2-yl]-3-pyridyl]-2-(2,2,2-trifluoroethyl)pyrazole-3-carboxamide

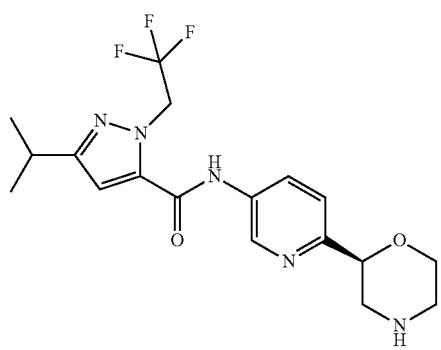 [SMILES: CC(C)c1cc(C(=O)Nc2ccc([C@@H]3CNCCO3)nc2)n(CC(F)(F)F)n1]

a) Ethyl 5-isopropyl-1H-pyrazole-3-carboxylate

To a solution of ethyl 4-methyl-3-oxopentanoate (4 g, 21.6 mmol, CAS: 7152-15-0) in ethanol (100 mL), was added acetic acid (1.9 g, 32.4 mmol) and hydrazine monohydrate (1.7 g, 0.032 mol, CAS: 7803-57-8). The reaction mixture was stirred for 12 hours until LCMS analysis indicated the completion of the reaction. The reaction solution was concentrated under reduced pressure and diluted with water. The mixture was extracted twice with dichloromethane (2×100 mL). The combined organic layers were washed with brine (40 mL), dried over Na$_2$SO$_4$, filtered through thin silica pad, and concentrated under vacuum to give ethyl 5-isopropyl-1H-pyrazole-3-carboxylate (2.1 g, 54% yield) as a yellow oil.

MS (ESI): 183.2 (M+H)$^+$.

b) Ethyl 5-isopropyl-2-(2,2,2-trifluoroethyl)pyrazole-3-carboxylate

To a solution of ethyl 5-isopropyl-1H-pyrazole-3-carboxylate (1 g, 5.5 mmol) in DMF (10 mL), were added 2,2,2-trifluoroethyl iodide (1.7 g, 8.3 mmol, CAS: 353-83-3) and Cs$_2$CO$_3$ (2.1 g, 11 mmol). The reaction mixture was stirred at 50° C. for 12 hours. Then the reaction solution was concentrated under reduced pressure and diluted with water. The mixture was extracted with ethyl acetate (2×100 mL). The combined organic layers were washed with brine (50 mL), dried over Na$_2$SO$_4$, filtered through a thin silica pad, and concentrated under vacuum. The crude product was purified by silica gel chromatography to give ethyl 5-isopropyl-2-(2,2,2-trifluoroethyl)pyrazole-3-carboxylate (500 mg, 36% yield) as a white solid.
MS (ESI): 265.2 (M+H)$^+$.

c) 5-Isopropyl-2-(2,2,2-trifluoroethyl)pyrazole-3-carboxylic acid

To a solution of ethyl 5-isopropyl-2-(2,2,2-trifluoroethyl)pyrazole-3-carboxylate (2 g, 7.6 mmol) in MeOH/H$_2$O (V/V=3:1, 12 mL) was added NaOH (1.2 g, 30.3 mmol). The reaction mixture was stirred at 30° C. for 2 hours. The reaction solution was concentrated under reduced pressure and diluted with water. The mixture was acidified to about pH=2 with 2N HCl (30 mL). The mixture was extracted with ethyl acetate (2×100 mL). The combined organic layers were washed with brine (100 mL), dried over Na$_2$SO$_4$, filtered through thin silica pad, and concentrated under reduced pressure. Further drying under high vacuum gave 5-isopropyl-2-(2,2,2-trifluoroethyl)pyrazole-3-carboxylic acid (1.6 g, 89% yield) as a white solid.
$^1$H NMR (CDCl$_3$, 400 Mhz): δ 6.91 (s, 1H), 5.25 (q, 2H), 3.04 (m, 1H), 1.29 (d, 6H).
MS (ESI): 237.2 (M+H)$^+$.

d) 5-Isopropyl-N-[6-[(2S)-morpholin-2-yl]-3-pyridyl]-2-(2,2,2-trifluoroethyl)pyrazole-3-carboxamide The title compound was obtained in analogy to example 67 using 5-isopropyl-2-(2,2,2-trifluoroethyl)pyrazole-3-carboxylic acid instead of 3-ethyl-4-methyl-1H-pyrazole-5-carboxylic acid. White solid.
MS (ESI): 398.2 (M+H)$^+$.

Example 93

2-Isopropyl-N-[6-[(2S)-morpholin-2-yl]-3-pyridyl]-5-(2,2,2-trifluoroethoxy)pyrazole-3-carboxamide

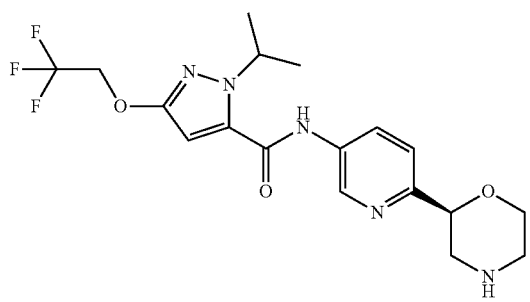 [SMILES: CC(C)n1nc(OCC(F)(F)F)cc1C(=O)Nc1ccc([C@@H]2CNCCO2)nc1]

a) Methyl 5-hydroxy-1H-pyrazole-3-carboxylate

To a solution of hydrazine monohydrate (44.8 g, 0.894 mol, CAS: 7803-57-8) in toluene (300 mL) were added acetic acid (180 mL) and acetylenedicarboxylic acid dimethyl ester (100 mL, 0.813 mol, CAS: 762-42-5). The solution was stirred at room temperature for 3 hours. The mixture was poured into iced water. The precipitate was collected by filtration, washed with cold water, and dried under high vacuum to give methyl 5-hydroxy-1H-pyrazole-3-carboxylate (67.5 g, 59% yield) as a white solid.
$^1$H NMR (400 MHz, DMSO-d$^6$): δ 12.81 (bra, 1H), 10.03 (br, 1H), 5.91 (s, 1H), 3.78 (s, 3H).

b) Methyl 5-(2,2,2-trifluoroethoxy)-1H-pyrazole-3-carboxylate

To a solution of methyl 5-hydroxy-1H-pyrazole-3-carboxylate (10 g, 70.4 mmol), Cs$_2$CO$_3$ (25 g, 77.5 mmol) in DMF (100 ml) was added 2,2,2-trifluoroethyl trifluoromethanesulfonate (16.3 g, 70.4 mmol) in portions. The solution was stirred at room temperature overnight. Then the reaction mixture was poured into 500 ml iced water. The precipitate was collected by filtration, washed with cooled water, and dried under high vacuum to give methyl 5-(2,2,2-trifluoroethoxy)-1H-pyrazole-3-carboxylate (12 g, 76% yield) as a white solid.
$^1$H NMR (400 MHz, DMSO-d$^6$): δ 13.41 (s, 1H), 6.43 (s, 1H), 4.86 (m, 2H), 3.84 (s, 3H) MS (ESI): 225.1 (M+H)$^+$.

c) Methyl 2-isopropyl-5-(2,2,2-trifluoroethoxy)pyrazole-3-carboxylate

To a solution of methyl 5-(2,2,2-trifluoroethoxy)-1H-pyrazole-3-carboxylate (12.0 g, 53.4 mmol) and Cs$_2$CO$_3$ (52.0 g, 161 mmol) in DMF (100.0 ml) was added 2-bromopropane (7.2 g, 56.0 mmol) in portions. The solution was stirred at room temperature overnight. Then the reaction solution was concentrated in vacuum to remove at least 50% of DMF. The remaining mixture was poured into water. The precipitate was collected by filtration, washed with cold water, dried under high vacuum to give methyl 2-isopropyl-5-(2,2,2-trifluoroethoxy)pyrazole-3-carboxylate (10.3 g, 74% yield) as a white solid.
$^1$H NMR (400 MHz, DMSO-d$^6$): δ 6.45 (s, 1H), 5.35 (m, 1H), 4.82 (q, 2H), 3.83 (s, 3H), 1.371 (d, 6H).
MS (ESI): 267.0 (M+H)$^+$.

d) 2-Isopropyl-5-(2,2,2-trifluoroethoxy)pyrazole-3-carboxylic acid

A solution of methyl 2-isopropyl-5-(2,2,2-trifluoroethoxy)pyrazole-3-carboxylate (4.3 g, 16.2 mmol) and NaOH (1.9 g, 48.5 mmol) in MeOH/H2O (V/V=3:1, 50.0 ml) was stirred at room temperature overnight. The reaction mixture was acidified to pH=4~5 by adding concentrated HCl (about 5 ml) at 0° C. The solution was poured into 500 ml iced water. The precipitate was collected by filtration, washed with cooled water, and dried under high vacuum to give 2-isopropyl-5-(2,2,2-trifluoroethoxy)pyrazole-3-carboxylic acid (3.86 g, 95% yield) as a white solid.
$^1$H NMR (400 MHz, DMSO-d$^6$): δ 6.37 (s, 1H), 5.38 (m, 1H), 4.79 (q, 2H), 1.34 (d, 6H).
MS (ESI): 252.9 (M+H)$^+$.

e) 2-Isopropyl-N-[6-[(2S)-morpholin-2-yl]-3-pyridyl]-5-(2,2,2-trifluoroethoxy)pyrazole-3-carboxamide The title compound was obtained in analogy to example 67 using 2-isopropyl-5-(2,2,2-trifluoroethoxy)pyrazole-3-carboxylic acid instead of 3-ethyl-4-methyl-1H-pyrazole-5-carboxylic acid. White solid.
MS (ESI): 414.2 (M+H)$^+$.

Example 94

3-Isobutyl-N-[6-[(2R)-morpholin-2-yl]-3-pyridyl]-1H-pyrazole-5-carboxamide

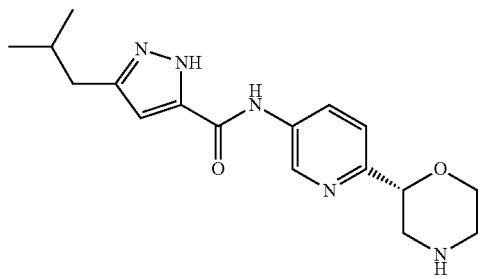 [SMILES: CC(C)Cc1cc(C(=O)Nc2ccc([C@H]3CNCCO3)nc2)[nH]n1]

The title compound was obtained in analogy to example 66 using 3-isobutyl-1H-pyrazole-5-carboxylic acid (CAS: 92933-49-8) instead of 3-ethyl-4-methyl-1H-pyrazole-5-carboxylic acid. White solid.
MS (ESI): 330.2 (M+H)$^+$.

Example 95

4-Fluoro-3-isobutyl-N-[6-[(2R)-morpholin-2-yl]-3-pyridyl]-1H-pyrazole-5-carboxamide

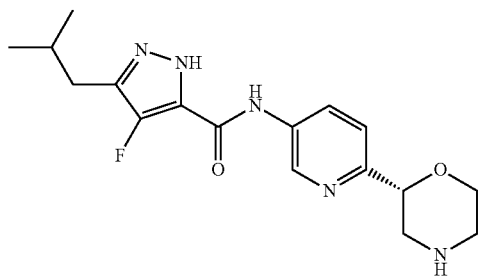 [SMILES: CC(C)Cc1n[nH]c(C(=O)Nc2ccc([C@H]3CNCCO3)nc2)c1F]

The title compound was obtained in analogy to example 66 using 4-fluoro-5-isobutyl-1H-pyrazole-3-carboxylic acid instead of 3-ethyl-4-methyl-1H-pyrazole-5-carboxylic acid. Waxy solid.
MS (ESI): 348.2 (M+H)$^+$.

Example 96

3-Butyl-4-fluoro-N-[6-[(2R)-morpholin-2-yl]-3-pyridyl]-1H-pyrazole-5-carboxamide

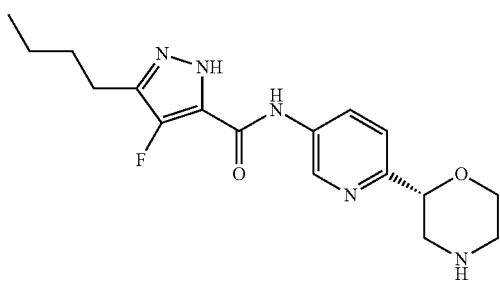 [SMILES: CCCCc1n[nH]c(C(=O)Nc2ccc([C@H]3CNCCO3)nc2)c1F]

The title compound was obtained in analogy to example 66 using 5-butyl-4-fluoro-1H-pyrazole-3-carboxylic acid (CAS: 681034-65-1) instead of 3-ethyl-4-methyl-1H-pyrazole-5-carboxylic acid. Waxy solid.
MS (ESI): 348.2 (M+H)$^+$.

Example 97

3-Butyl-N-[6-[(2R)-morpholin-2-yl]-3-pyridyl]-1H-pyrazole-5-carboxamide

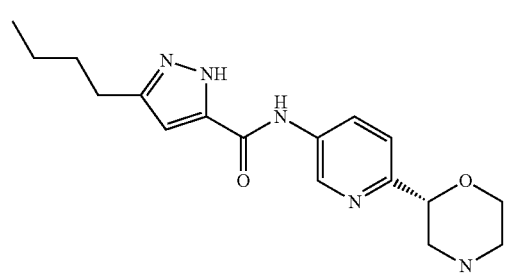

The title compound was obtained in analogy to example 66 using 5-butyl-1H-pyrazole-3-carboxylic acid (CAS: 92933-48-7) instead of 3-ethyl-4-methyl-1H-pyrazole-5-carboxylic acid. White solid.
MS (ESI): 330.2 (M+H)$^+$.

Example 98

5-Isopropyl-N-[6-[(2R)-morpholin-2-yl]-3-pyridyl]-2-(2,2,2-trifluoroethyl)pyrazole-3-carboxamide

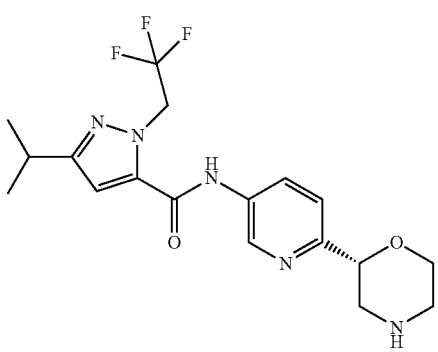 [SMILES: CC(C)c1cc(C(=O)Nc2ccc([C@H]3CNCCO3)nc2)n(CC(F)(F)F)n1]

The title compound was obtained in analogy to example 66 using 5-isopropyl-2-(2,2,2-trifluoroethyl)pyrazole-3-carboxylic acid instead of 3-ethyl-4-methyl-1H-pyrazole-5-carboxylic acid. White solid.
MS (ESI): 398.1 (M+H)$^+$.

Example 99

2-Isopropyl-N-[6-[(2R)-morpholin-2-yl]-3-pyridyl]-5-(2,2,2-trifluoroethoxy)pyrazole-3-carboxamide

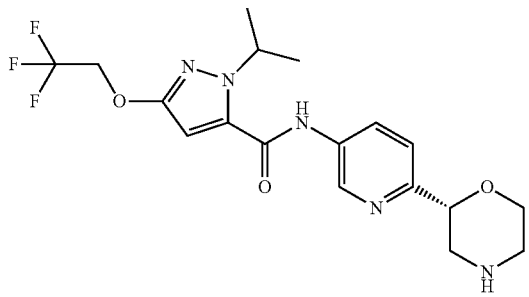 [SMILES: CC(C)n1nc(OCC(F)(F)F)cc1C(=O)Nc1ccc([C@H]2CNCCO2)nc1]

The title compound was obtained in analogy to example 66 using 2-isopropyl-5-(2,2,2-trifluoroethoxy)pyrazole-3-carboxylic acid instead of 3-ethyl-4-methyl-1H-pyrazole-5-carboxylic acid. White solid.
MS (ESI): 414.2 (M+H)$^+$.

Example 100

4-Chloro-3-ethoxy-N-[6-[(2R)-morpholin-2-yl]-3-pyridyl]-1H-pyrazole-5-carboxamide

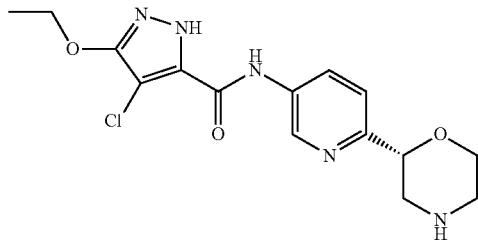 [SMILES: CCOc1n[nH]c(C(=O)Nc2ccc([C@H]3CNCCO3)nc2)c1Cl]

The title compound was obtained in analogy to example 66 using 4-chloro-5-ethoxy-1H-pyrazole-3-carboxylic acid instead of 3-ethyl-4-methyl-1H-pyrazole-5-carboxylic acid. White solid.
MS (ESI): 352.1 ($\{^{35}Cl\}$M+H)$^+$, 354.1 ($\{^{37}Cl\}$M+H)$^+$.

Example 101

4-Chloro-N-[6-[(2R)-morpholin-2-yl]-3-pyridyl]-3-(2,2,2-trifluoroethoxy)-1H-pyrazole-5-carboxamide

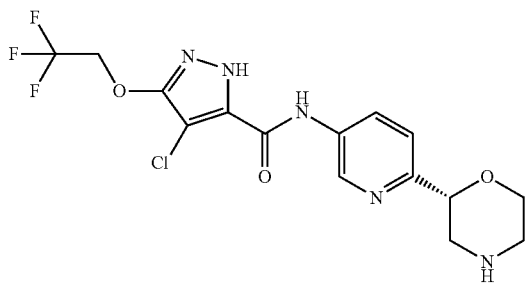 [SMILES: O=C(Nc1ccc([C@H]2CNCCO2)nc1)c1[nH]nc(OCC(F)(F)F)c1Cl]

The title compound was obtained in analogy to example 66 using 4-chloro-5-(2,2,2-trifluoroethoxy)-1H-pyrazole-3-carboxylic acid instead of 3-ethyl-4-methyl-1H-pyrazole-5-carboxylic acid. White solid.
MS (ESI): 406.1 ($\{^{35}Cl\}$M+H)$^+$, 408.0 ($\{^{37}Cl\}$M+H)$^+$.

Example 102

(RS)-5-Chloro-N-(5-chloro-2-pyridyl)-6-morpholin-2-yl-pyridin-3-amine

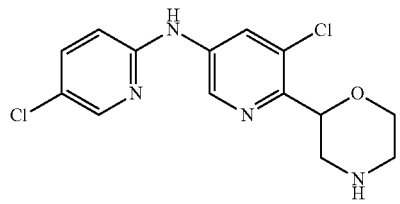

a) 5-Bromo-3-chloro-pyridine-2-carbonyl chloride

To a suspension of 5-bromo-3-chloropyridine-2-carboxylic acid (5.0 g, 21.06 mmol, CAS: 1189513-51-6) in dichloromethane (50 mL) were added oxalyl chloride (3.38 g, 31.6 mmol, CAS: 79-37-8) and DMF (0.1 mL) at room temperature. The reaction was continued for 5 hours. The solution was concentrated under reduced pressure and dried under high vacuum to give crude 5-bromo-3-chloro-pyridine-2-carbonyl chloride (5.4 g, 100% of yield) as a yellow solid, which was used for the next step directly.

b) 2-Bromo-1-(5-bromo-3-chloro-2-pyridyl)ethanone

To a solution of crude 5-bromo-3-chloro-pyridine-2-carbonyl chloride (5.4 g, 21.06 mmol) in CH$_3$CN (100 mL) was added (trimethylsilyl)diazomethane solution (2 M in hexane, 31.6 mL, 63.2 mmol, CAS: 18107-18-1) dropwise at 0~5° C. The mixture was stirred at room temperature overnight. HBr (48% in water, 10 mL) was added at 0~5° C. The solution was stirred for an hour. The reaction solution was poured into water (200 mL). The mixture was extracted with EtOAc (200 mL). The organic layer was washed with brine (100 mL), dried over Na$_2$SO$_4$, and concentrated under reduced pressure. The residue was purified through column chromatography (Petroleum ether/ethyl acetate=100/1 by volume) to give 5-bromo-3-chloro-pyridine-2-carbonyl chloride (5.17 g, 78.3% yield) as a yellow solid.
MS (ESI): 315.8 ([$\{^{81}Br+^{81}Br\}$M+H]$^+$), 313.8 ([$\{^{81}Br+^{79}Br\}$M+H]$^+$), 311.8 ([$\{^{79}Br+^{79}Br\}$M+H]$^+$).

c) 5-Bromo-3-chloro-2-(oxiran-2-yl)pyridine

To a solution of 5-bromo-3-chloro-pyridine-2-carbonyl chloride (5.17 g, 16.5 mmol) in ethanol (100 mL) was added NaBH$_4$ (752.4 mg, 19.8 mmol) at 0~5° C. The solution was stirred at room temperature for an hour. K$_2$CO$_3$ (2.3 g, 16.5 mmol) was added. The reaction was continued overnight. The reaction mixture was poured into water (200 mL) and extracted with ethyl acetate (200 mL). The organic layer was washed with brine (100 mL), dried over Na$_2$SO$_4$, and concentrated under reduced pressure. Further drying under high vacuum gave 5-bromo-3-chloro-2-(oxiran-2-yl)pyridine (3.86 g, 100% yield) as a yellow oil, which was used for the next step directly.

MS (ESI): 235.9 ([{$^{81}$Br}M+H]$^+$), 233.9 ([{$^{79}$Br}M+H]$^+$).

d) 1-(5-Bromo-3-chloro-2-pyridyl)-2-(2-hydroxyethylamino)ethanol

To a solution of 5-bromo-3-chloro-2-(oxiran-2-yl)pyridine (3.86 g, 16.5 mmol) in THF (20 mL) was added ethanolamine (10 mL, CAS: 141-43-5). The solution was stirred at room temperature overnight. Then the solution was diluted with ethyl acetate (200 mL). The organic layer was washed with brine (100 mL), dried over Na$_2$SO$_4$, and concentrated under reduced pressure. Further drying under high vacuum gave crude 1-(5-bromo-3-chloro-2-pyridyl)-2-(2-hydroxyethylamino)ethanol (3.0 g, 61.6% yield) as a yellow oil, which was used for the next step directly.

e) tert-Butyl N-[2-(5-bromo-3-chloro-2-pyridyl)-2-hydroxy-ethyl]-N-(2-hydroxyethyl)carbamate To a solution of 1-(5-bromo-3-chloro-2-pyridyl)-2-(2-hydroxyethylamino)ethanol (3.0 g, 16.5 mmol) in a mixture of THF (30 mL) and water (20 mL) were added di-tert-butyl dicarbonate (3.29 g, 15.22 mmol, CAS: 24424-99-5) and K$_2$CO$_3$ (2.8 g, 20.3 mmol). The solution was stirred at room temperature overnight. The reaction solution was diluted with water (50 mL). The mixture was extracted with ethyl acetate (200 mL). The organic layer was washed with brine (100 mL), dried over Na$_2$SO$_4$, and concentrated under reduced pressure. The residue was purified through column chromatography (CH$_2$Cl$_2$/MeOH=100/1~50/1 by volume) to give tert-butyl N-[2-(5-bromo-3-chloro-2-pyridyl)-2-hydroxy-ethyl]-N-(2-hydroxyethyl)carbamate (1.5 g, 37.5% yield) as a yellow oil.

MS (ESI): 295.0 ([{$^{79}$Br}M-Boc+H]$^+$), 296.9 ([{$^{81}$Br}M-Boc+H]$^+$), 338.9 ([{$^{79}$Br}M-56+H]$^+$), 340.9 ([{$^{81}$Br}M-56+H]$^+$), f) tert-Butyl 2-(5-bromo-3-chloro-2-pyridyl)morpholine-4-carboxylate

To a solution of tert-butyl N-[2-(5-bromo-3-chloro-2-pyridyl)-2-hydroxy-ethyl]-N-(2-hydroxyethyl)carbamate (1.5 g, 3.79 mmol) in toluene (20 mL) were added PPh$_3$ (1.19 g, 4.55 mmol) and Et$_3$N (957 mg, 9.47 mmol) at room temperature. Then a solution of diisopropyl azodicarboxylate (0.92 g, 4.55 mmol, CAS: 2446-83-5) in toluene (10 mL) was added at 0~5° C. The solution was stirred at room temperature overnight. Then the reaction solution was diluted with ethyl acetate (200 mL). The mixture was washed with aqueous NaHCO$_3$ (100 mL×3) and brine (100 mL×2), dried over Na$_2$SO$_4$, and concentrated under reduced pressure. The residue was purified through column chromatography (Petroleum ether/ethyl acetate=20/1~5/1 by volume) to give tert-butyl 2-(5-bromo-3-chloro-2-pyridyl)morpholine-4-carboxylate (1.0 g, 70% yield) as a white solid.

$^1$H NMR (400 MHz, Methanol-d$^4$): δ 8.62 (d, J=2 Hz, 1H), 7.89 (d, J=2 Hz, 1H), 4.89 (d, J=10 Hz, 1H), 4.30~3.8 (m, 3H), 3.76 (m, 1H), 3.13 (br, 2H), 1.49 (s, 9H).

g) (RS)-5-Chloro-N-(5-chloro-2-pyridyl)-6-morpholin-2-yl-pyridin-3-amine

To a solution of tert-butyl 2-(5-bromo-3-chloro-2-pyridyl)morpholine-4-carboxylate (80 mg, 0.211 mmol) and 2-amino-5-chloropyridine (27 mg, 0.211 mmol, CAS: 1072-98-6) in dioxane (1 mL) were added Xantphos (4,5-bis(diphenylphosphino)-9,9-dimethylxanthene, 36.7 mg, 0.063 mmol, CAS: 161265-03-8), Cs$_2$CO$_3$ (206.2 mg, 0.633 mmol), and tris(dibenzylideneacetone) dipalladium(0) (19.3 mg, 0.021 mmol, CAS: 51364-51-3) under N$_2$ atmosphere. The mixture was stirred at 80° C. overnight. Then the solution was poured into water (100 mL). The mixture was extracted with CH$_2$Cl$_2$ (150 mL×2). The combined organic layers were dried over Na$_2$SO$_4$ and concentrated under reduced pressure. The residue was dissolved in CH$_2$Cl$_2$ (1 mL). Then trifluoroacetic acid (1 mL) was added. The solution was stirred at room temperature for 3 hours. The reaction solution was concentrated under reduced pressure. The residue was purified through Prep-HPLC (0.5% TFA in CH$_3$CN) to give (RS)-5-chloro-N-(5-chloro-2-pyridyl)-6-morpholin-2-yl-pyridin-3-amine (50 mg) as a white solid.

$^1$H NMR (400 MHz, Methanol-d$^4$): δ 8.62 (dd, 2H), 8.21 (s, 1H), 7.64 (dd, 1H), 6.87 (d, 1H), 5.23 (dd, 1H), 4.11 (m, 1H), 3.98 (m, 1H), 3.67 (m, 1H), 3.49 (m, 1H), 3.35~3.30 (m, 2H).

MS (ESI): 325.1 ({$^{35}$Cl}M+H)$^+$, 327.0 ({$^{37}$Cl}M+H)$^+$.

Example 103

(RS)-5-Chloro-6-morpholin-2-yl-N-[5-(trifluoromethyl)-2-pyridyl]pyridin-3-amine

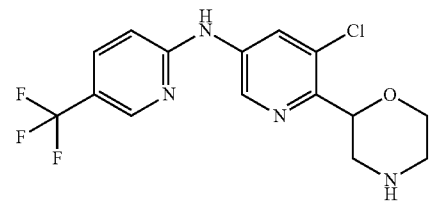 [SMILES: FC(F)(F)c1ccc(Nc2cnc(C3CNCCO3)c(Cl)c2)nc1]

The title compound was obtained in analogy to example 102 using 2-amino-5-trifluoromethylpyridine (CAS: 74784-70-6) instead of 2-amino-5-chloropyridine in step (g). White solid. MS (ESI): 361.0 ([{$^{37}$Cl}M+H]$^+$), 359.1 ([{$^{35}$Cl}M+H]$^+$).

Example 104

(RS)-5-Methyl-6-morpholin-2-yl-N-[5-(trifluoromethyl)-2-pyridyl]pyridin-3-amine

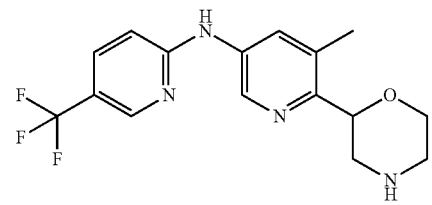 [SMILES: Cc1cc(Nc2ccc(C(F)(F)F)cn2)cnc1C1CNCCO1]

a) 2-Bromo-1-(5-bromo-3-methyl-2-pyridyl)ethanone

A solution of 5-bromo-3-methylpyridine-2-carbonyl chloride (4 g, 17 mmol, CAS: 1114809-24-3) in CH$_3$CN (60 mL)

was stirred at 0° C. (Trimethylsilyl)diazomethane (2M in hexanes, 21 mL, 42 mmol, CAS: 18107-18-1) was added. The mixture was stirred at room temperature overnight until TLC analysis indicated the complete consumption of the starting material. HBr (12 mL, 48% aqueous solution) was added. The resulting solution was stirred at room temperature overnight. The mixture was treated with saturated aqueous NaHCO$_3$ to adjust the pH to about 7. The layers were separated. The aqueous layer was extracted with ethyl acetate (200 mL×2). The combined organic layers were washed with brine (200 mL), dried over sodium sulfate, and concentrated under reduced pressure. The residue (4.5 g) was used for the next step without purification.

b) 5-Bromo-3-methyl-2-(oxiran-2-yl)pyridine

A solution of 2-bromo-1-(5-bromo-3-methyl-2-pyridyl)ethanone (4 g, 13.7 mmol) in EtOH (80 mL) was stirred at 0° C. NaBH$_4$ (623 mg, 16.4 mmol) was added. The mixture was stirred at room temperature for 4 hours. K$_2$CO$_3$ (945 mg, 6.9 mmol) was added. The resulting solution was stirred at room temperature overnight. The mixture was diluted with water (300 ml). The layers were separated. The aqueous layer was extracted with EtOAc (300 mL×2). The combined organic layers were washed with brine (300 mL), dried over sodium sulfate, and concentrated under reduced pressure. The residue was used for the next step without purification.

c) 1-(5-Bromo-3-methyl-2-pyridyl)-2-(2-hydroxyethylamino)ethanol

To a stirred solution of 5-bromo-3-methyl-2-(oxiran-2-yl)pyridine (3.5 g, 16.4 mmol) in THF (15 mL) was added 2-aminoethanol (15 mL, CAS: 41-43-5). The mixture was stirred at room temperature overnight. The reaction mixture was then poured into THF/EtOAc (1:1, 200 mL) and washed with brine (100 mL). The organic layer was dried over Na$_2$SO$_4$ and concentrated to give crude 1-(5-bromo-3-methyl-2-pyridyl)-2-(2-hydroxyethylamino)ethanol (2.6 g, 58% yield) as an oil which was used in the next step without purification.

MS (ESI): 277.0 ([{$^{81}$Br}M+H]$^+$), 275.0 ([{$^{79}$Br}M+H]$^+$).

d) tert-Butyl N-[2-(5-bromo-3-methyl-2-pyridyl)-2-hydroxy-ethyl]-N-(2-hydroxyethyl)carbamate A mixture of 1-(5-bromo-3-methyl-2-pyridyl)-2-(2-hydroxyethylamino)ethanol (2.6 g, 9.5 mmol, crude), K$_2$CO$_3$ (3.0 g, 22 mmol) and (Boc)$_2$O (1.9 g, 7.3 mmol, CAS: 24424-99-5) in THF (30 mL) was stirred at room temperature for 12 hours. The mixture was then diluted with water (200 mL) and extracted with ethyl acetate (200 mL×2). The combined organic layers were washed with water (100 mL) and brine (100 mL), and concentrated under reduced pressure. Purification by silica gel chromatography gave tert-butyl N-[2-(5-bromo-3-methyl-2-pyridyl)-2-hydroxyethyl]-N-(2-hydroxyethyl)carbamate (1.31 g, 37% yield) as a light yellow oil.

e) tert-Butyl 2-(5-bromo-3-methyl-2-pyridyl)morpholine-4-carboxylate

A mixture of tert-butyl N-[2-(5-bromo-3-methyl-2-pyridyl)-2-hydroxy-ethyl]-N-(2-hydroxyethyl)carbamate (1.3 g, 3.5 mmol), PPh$_3$ (1.02 g, 4.2 mmol), and Et$_3$N (900 mg, 9 mmol) was stirred at 0° C. for 10 minutes. Diisopropyl azodicarboxylate (848 mg, 4.2 mmol, CAS: 2446-83-5) was added dropwise. The reaction was continued overnight. The mixture was concentrated under reduced pressure. Purification by flash chromatography on silica gel gave tert-butyl 2-(5-bromo-3-methyl-2-pyridyl)morpholine-4-carboxylate (600 mg, 48% yield) as an off-white solid.

$^1$H NMR (400 MHz, Methanol-d$^4$): δ 8.46 (d, 1H), 7.87 (d, 1H), 4.65 (m, 1H), 4.11 (m, 1H), 3.98 (m, 2H), 3.72 (t, 1H), 3.32 (m, 2H), 2.43 (s, 3H), 1.52 (s, 9H).

MS (ESI): 359.0 ([{$^{81}$Br}M+H]$^+$), 357.0 ([{$^{79}$Br}M+H]$^+$).

(RS)-5-Methyl-6-morpholin-2-yl-N-[5-(trifluoromethyl)-2-pyridyl]pyridin-3-amine

A mixture of tert-butyl 2-(5-bromo-3-methyl-2-pyridyl)morpholine-4-carboxylate (60 mg, 0.17 mmol), 2-amino-5-trifluoromethylpyridine (26 mg, CAS: 74784-70-6), Xantphos (20 mg, 0.034 mmol, CAS: 161265-03-8), Pd$_2$(dba)$_3$ (16 mg, 0.017 mmol, CAS: 51364-51-3) and Cs$_2$CO$_3$ (166 mg, 0.51 mmol) in dioxane (5 mL) was stirred at 90° C. for 12 hours under N$_2$ atmosphere. Then the mixture was diluted with water (100 mL) and extracted with ethyl acetate (100 mL×2). The combined organic layers were washed with water (100 mL), and concentrated under reduced pressure. The residue was dried further under high vacuum.

Then the residue was dissolved in dichloromethane (2 mL). Triethylamine (0.5 ml) was added. The resulting mixture was stirred at room temperature for an hour. Volatiles were removed under reduced pressure. Purification silica gel chromatography gave (RS)-5-methyl-6-morpholin-2-yl-N-[5-(trifluoromethyl)-2-pyridyl]pyridin-3-amine (15 mg) as a white solid.

$^1$H NMR (400 MHz, Methanol-d$^4$): δ 9.05 (d, 1H), 8.54 (s, 1H), 8.24 (d, 1H), 7.89 (dd, 1H), 7.01 (d, 1H), 5.21 (dd, 1H), 4.17 (m, 1H), 4.04 (m, 1H), 3.60 (m, 2H), 3.41 (m, 1H), 3.34 (m, 1H), 2.50 (s, 3H).

MS (ESI): 339.1 (M+H)$^+$.

Example 105

4-Chloro-N-[6-[(2S)-morpholin-2-yl]-3-pyridyl]-3-(2,2,2-trifluoroethoxy)-1H-pyrazole-5-carboxamide

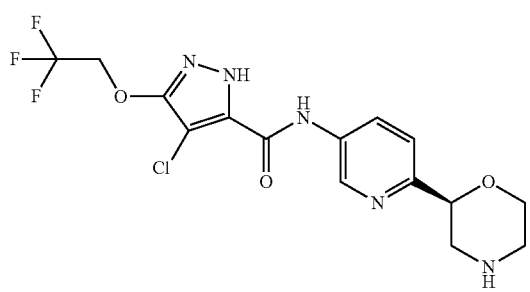 [SMILES: O=C(Nc1ccc([C@@H]2CNCCO2)nc1)c1[nH]nc(OCC(F)(F)F)c1Cl]

The title compound was obtained in analogy to example 67 using 4-chloro-5-(2,2,2-trifluoroethoxy)-1H-pyrazole-3-carboxylic acid instead of 3-ethyl-4-methyl-1H-pyrazole-5-carboxylic acid. White solid.

MS (ESI): 406.1 ({$^{35}$Cl}M+H)$^+$, 408.1 ({$^{37}$Cl}M+H)$^+$.

Example 106

4-Chloro-3-ethoxy-N-[6-[(2S)-morpholin-2-yl]-3-pyridyl]-1H-pyrazole-5-carboxamide

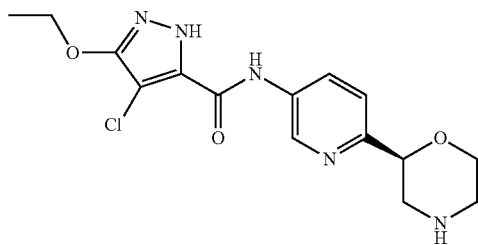 [SMILES: CCOc1n[nH]c(C(=O)Nc2ccc([C@@H]3CNCCO3)nc2)c1Cl]

The title compound was obtained in analogy to example 67 using 4-chloro-5-ethoxy-1H-pyrazole-3-carboxylic acid instead of 3-ethyl-4-methyl-1H-pyrazole-5-carboxylic acid. White solid.

MS (ESI): 352.1 ($\{^{35}Cl\}M+H)^+$, 354.1 ($\{^{37}Cl\}M+H)^+$.

Example 107

(RS)—N-(5-Chloro-6-morpholin-2-yl-3-pyridyl)-2-(trifluoromethyl)pyridine-4-carboxamide

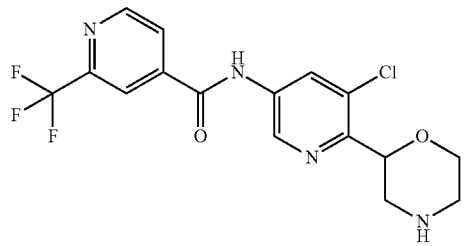

a) tert-Butyl 2-[5-(benzhydrylideneamino)-3-chloro-2-pyridyl]morpholine-4-carboxylate To a solution of tert-butyl 2-(5-bromo-3-chloro-2-pyridyl)morpholine-4-carboxylate (0.4 g, 1.057 mmol) and benzophenone imine (191.3 mg, 1.057 mmol, CAS: 1013-88-3) in dioxane (15 mL) were added Xantphos (4,5-bis(diphenylphosphino)-9,9-dimethylxanthene, 183.5 mg, 0.317 mmol, CAS: 161265-03-8), Cs$_2$CO$_3$ (1.03 g, 3.17 mmol) and tris(dibenzylideneacetone) dipalladium(0) (96.8 mg, 0.1 mmol, CAS: 51364-51-3) under N$_2$ atmosphere. The mixture was stirred at 85° C. overnight. Then the reaction mixture was filtered. The filtrate was concentrated in vacuum to give crude tert-butyl 2-[5-(benzhydrylideneamino)-3-chloro-2-pyridyl]morpholine-4-carboxylate (505 mg, 100% of yield) as a yellow oil, which was used for the next step directly.

b) tert-Butyl 2-(5-amino-3-chloro-2-pyridyl)morpholine-4-carboxylate

To a solution of tert-butyl 2-[5-(benzhydrylideneamino)-3-chloro-2-pyridyl]morpholine-4-carboxylate (505 mg, 1.057 mmol) in methanol (10 mL) were added sodium acetate (433.4 mg, 5.28 mmol) and hydroxylamine hydrochloride (110.2 mg, 1.58 mmol). The mixture was stirred at room temperature for 2 hours. The solution was poured into water (50 mL) and extracted with CH$_2$Cl$_2$ (100 mL×2). The combined organic layers were dried over Na$_2$SO$_4$, concentrated in vacuum, and purified through column chromatography (CH$_2$Cl$_2$/methanol=100/1~50/1 by volume) to give tert-butyl 2-(5-amino-3-chloro-2-pyridyl)morpholine-4-carboxylate (270 mg, 81% yield) as a yellow solid.

MS (ESI): 258.0 ($[\{^{35}Cl\}M-56+H]^+$), 314.0 ($[\{^{35}Cl\}M+H]^+$), 316.0 ($[\{^{37}Cl\}M+H]^+$), 336.0 ($[\{^{35}Cl\}M+Na]^+$).

c) (RS)—N-(5-Chloro-6-morpholin-2-yl-3-pyridyl)-2-(trifluoromethyl)pyridine-4-carboxamide To a solution of 2-(trifluoromethyl)pyridine-4-carboxylic acid (40 mg, 0.21 mmol, CAS: 131747-41-6) in DMF (1 mL) were added HATU (79.7 mg, 0.21 mmol, CAS: 148893-10-1), diisopropylethyl amine (73.7 mg, 0.57 mmol), and tert-butyl 2-(5-amino-3-chloro-2-pyridyl)morpholine-4-carboxylate (60 mg, 0.19 mmol). The solution was stirred at room temperature overnight. Then the reaction mixture was diluted with CH$_2$Cl$_2$ (50 mL). The solution was washed with brine (50 mL×2), dried over Na$_2$SO$_4$, and concentrated under vacuum. The residue was dissolved in CH$_2$Cl$_2$ (1 mL) and trifluoroacetic acid (1 mL). The solution was stirred at room temperature for 2 hours. The reaction solution was concentrated under vacuum. The residue was purified through prep-HPLC (0.5% trifluoroacetic acid in CH$_3$CN) to give (RS)—N-(5-chloro-6-morpholin-2-yl-3-pyridyl)-2-(trifluoromethyl)pyridine-4-carboxamide (11 mg) as a white solid.

$^1$H NMR (400 MHz, Methanol-d$^4$): δ 8.95 (d, 1H), 8.90 (d, 1H), 8.50 (d, 1H), 8.34 (s, 1H), 8.15 (m, 1H), 5.28 (dd, 1H), 4.07 (m, 1H), 4.01 (m, 1H), 3.72 (m, 1H), 3.56 (m, 1H), 3.36~3.30 (m, 2H).

MS (ESI): 387.1 ($[\{^{35}Cl\}M+H]^+$), 389.1 ($[\{^{37}Cl\}M+H]^+$).

Example 108

(RS)-4-Chloro-N-(5-chloro-6-morpholin-2-yl-3-pyridyl)-3-propyl-1H-pyrazole-5-carboxamide

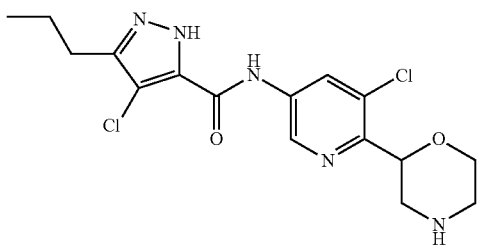

The title compound was obtained in analogy to example 107 using 4-chloro-5-propyl-1H-pyrazole-3-carboxylic acid (CAS: 1340578-20-2) instead of 2-(trifluoromethyl)pyridine-4-carboxylic acid in step (c). White solid. MS (ESI): 386.1 ($[\{^{37}Cl\}M+H]^+$), 384.1 ($[\{^{35}Cl\}M+H]^+$).

Example 109

(RS)-1-(5-Chloro-6-morpholin-2-yl-3-pyridyl)-3-(3-chlorophenyl)urea

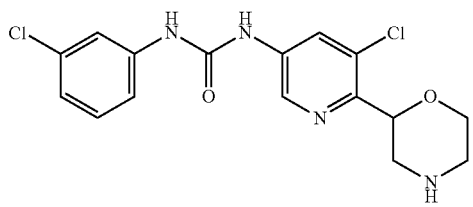

To a solution of tert-butyl 2-(5-amino-3-chloro-2-pyridyl)morpholine-4-carboxylate (60 mg, 0.19 mmol) in CH$_2$Cl$_2$ (1 mL) was added triethyl amine (38.4 mg, 0.38 mmol) and 3-chlorophenyl isocyana (29.2 mg, 0.19 mmol, CAS: 2909-38-8). The solution was stirred at room temperature overnight. The reaction solution was diluted with CH$_2$Cl$_2$ (50 mL), washed with brine (50 mL×2), dried over Na$_2$SO$_4$, and concentrated under vacuum. The residue was dissolved in a mixture of CH$_2$Cl$_2$ (1 mL) and trifluoroacetic acid (1 mL). The solution was stirred at room temperature for 2 hours. Volatiles were removed under reduced pressure. The residue was purified through prep-HPLC (0.5% trifluoroacetic acid in CH$_3$CN) to give the title compound (20 mg) as a white solid.

$^1$H NMR (400 MHz, Methanol-d$^4$): δ 8.58 (s, 1H), 8.25 (s, 1H), 7.67 (s, 1H), 7.31~7.27 (m, 2H), 7.08~7.06 (m, 1H), 5.27~5.24 (dd, J=12 Hz, 1H), 4.10~4.00 (m, 1H), 4.99~3.98 (m, 1H), 3.71~3.68 (m, 1H), 3.55~3.54 (m, 1H), 3.36~3.30 (m, 2H).

LCMS for compound RW-04-035-05: MS (ESI): 367.1 ({35Cl}M+H)+, 369.0 ({37Cl}M+H)+.

Example 110

(RS)—N-(5-Chloro-2-pyridyl)-5-fluoro-6-morpholin-2-yl-pyridin-3-amine

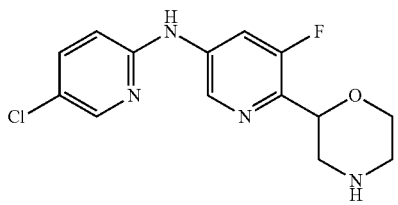 [SMILES: Fc1cc(Nc2ccc(Cl)cn2)cnc1C1CNCCO1]

a) 2-Bromo-1-(5-bromo-3-fluoro-2-pyridyl)ethanone

To a solution of 1-(5-bromo-3-fluoropyridin-2-yl)ethanone (5.5 g, 25.2 mmol, CAS: 1160936-52-6) in acetic acid (30 mL) were added hydrobromic acid solution (33 wt. % in acetic acid, 30 mL) and pyrrolidone hydrotribromide (8.4 g, 26.4 mmol, CAS: 22580-55-8) at room temperature. The solution was stirred at room temperature overnight. The solution was concentrated under reduced pressure. The residue was diluted with ethyl acetate (800 mL). The precipitate was collected by filtration and dried under high vacuum to give 2-bromo-1-(5-bromo-3-fluoro-2-pyridyl)ethanone (7.52 g, 79% yield) as an HBr salt.

b) 5-Bromo-3-fluoro-2-(oxiran-2-yl)pyridine

To a solution of 2-bromo-1-(5-bromo-3-fluoro-2-pyridyl)ethanone (7.52 g, 20 mmol, HBr salt) in ethanol (140 mL) was added NaBH$_4$ (910 mg, 24 mmol) at 0~5° C. Then the solution was stirred at room temperature for an hour. Sodium ethoxide (660 mg, 10 mmol) was added. The solution was stirred at room temperature overnight. The reaction solution was poured into water (100 mL) and extracted with ethyl acetate (100 mL×3). The combined organic layers were washed with brine (200 mL), dried over Na$_2$SO$_4$, and concentrated in vacuum to give 5-bromo-3-fluoro-2-(oxiran-2-yl)pyridine (4.4 g, 100% yield) as a yellow oil, which was used for the next step directly.

MS (ESI): 219.9 ([{$^{81}$Br}M+H]$^+$), 217.9 ([{$^{79}$Br}M+H]$^+$).

c) 1-(5-Bromo-3-fluoro-2-pyridyl)-2-(2-hydroxyethylamino)ethanol

To a solution of 5-bromo-3-fluoro-2-(oxiran-2-yl)pyridine (4.8 g, 22.12 mmol) in THF (20 mL) was added 2-aminoethanol (10 mL, CAS: 41-43-5). The solution was stirred at room temperature overnight. The reaction solution was diluted with ethyl acetate (200 mL). The organic layer was washed with brine (100 mL), dried over Na$_2$SO$_4$, and concentrated in vacuum to give crude 1-(5-bromo-3-fluoro-2-pyridyl)-2-(2-hydroxyethylamino)ethanol (5.0 g, 81% yield) as a yellow solid, which was used for the next step directly.

d) tert-Butyl N-[2-(5-bromo-3-fluoro-2-pyridyl)-2-hydroxy-ethyl]-N-(2-hydroxyethyl)carbamate To a solution of 1-(5-bromo-3-fluoro-2-pyridyl)-2-(2-hydroxyethylamino)ethanol (5.0 g, 17.9 mmol) in a mixture of THF (50 mL) and H$_2$O (30 mL) were added di-tert-butyl dicarbonate (5.8 g, 26.9 mmol, CAS: 24424-99-5) and K$_2$CO$_3$ (4.9 g, 36 mmol). The solution was stirred at room temperature overnight. The reaction solution was diluted with water (50 mL). The mixture was extracted with ethyl acetate (100 mL×2). The combined organic layers were washed with brine (100 mL), dried over Na$_2$SO$_4$, and concentrated under reduced pressure. The residue was purified through silica gel column chromatography (CH$_2$Cl$_2$/MeOH=100/1~50/1 by volume) to give tert-butyl N-[2-(5-bromo-3-fluoro-2-pyridyl)-2-hydroxy-ethyl]-N-(2-hydroxyethyl)carbamate (5.2 g, 77% yield) as a yellow oil.

MS (ESI): 278.9 ([{$^{79}$Br}M-Boc+H]$^+$), 280.9 ([{$^{81}$Br}M-Boc+H]$^+$).

e) tert-Butyl 2-(5-bromo-3-fluoro-2-pyridyl)morpholine-4-carboxylate

To a solution of tert-butyl N-[2-(5-bromo-3-fluoro-2-pyridyl)-2-hydroxy-ethyl]-N-(2-hydroxyethyl)carbamate (5.2 g, 13.7 mmol) in toluene (100 mL) were added PPh$_3$ (4.3 g, 16.4 mmol) and Et$_3$N (3.46 g, 34.25 mmol) at room temperature. Then a solution of DIAD (3.32 g, 16.4 mmol) in toluene (30 mL) was added at 0~5° C. The solution was stirred at room temperature overnight. The reaction solution was diluted with water (100 mL) and extracted with ethyl acetate (100 mL×2). The combined organic layers were washed with aqueous NaHCO$_3$ (100 mL×3) and brine (100 mL×2), dried over Na₂SO₄, and concentrated under reduced pressure. The residue was purified through silica gel column chromatography (Petroleum ether/Ethyl acetate=20/1~5/1 by volume) to give tert-butyl 2-(5-bromo-3-fluoro-2-pyridyl)morpholine-4-carboxylate (3.2 g, 65% yield) as a white solid.

MS (ESI): 361.0 ([{$^{79}$Br}M+H]$^+$), 363.0 ([{$^{81}$Br}M+H]$^+$).

f) (RS)—N-(5-Chloro-2-pyridyl)-5-fluoro-6-morpholin-2-yl-pyridin-3-amine

To a solution of tert-butyl 2-(5-bromo-3-fluoro-2-pyridyl)morpholine-4-carboxylate (80 mg, 0.221 mmol) and 2-amino-5-chloropyridine (28.4 mg, 0.221 mmol, CAS: 1072-98-6) in dioxane (1 mL) were added Xantphos (4,5-bis(diphenylphosphino)-9,9-dimethylxanthene, 38.4 mg, 0.066 mmol, CAS: 161265-03-8), Cs₂CO₃ (216 mg, 0.663 mmol), and tris(dibenzylideneacetone) dipalladium(0) (20 mg, 0.022 mmol, CAS: 51364-51-3) under N₂ atmosphere. The mixture was stirred at 80° C. overnight. Then the solution was poured into water (100 mL). The mixture was extracted with CH₂Cl₂ (150 mL×2). The combined organic layers were dried over Na₂SO₄ and concentrated under reduced pressure. The residue was dissolved in CH₂Cl₂ (1 mL). Then trifluoroacetic acid (1 mL) was added. The solution was stirred at room temperature for 3 hours.

The reaction solution was concentrated under reduced pressure. The residue was purified through Prep-HPLC (0.5% TFA in CH₃CN) to give (RS)—N-(5-Chloro-2-pyridyl)-5-fluoro-6-morpholin-2-yl-pyridin-3-amine (44 mg) as a white solid.

¹H NMR (400 MHz, Methanol-d⁴): δ 8.45 (m, 2H), 8.22 (d, 1H), 7.64 (dd, 1H), 6.88 (d, 1H), 5.12 (m, 1H), 4.12 (m, 1H), 3.98 (m, 1H), 3.67 (m, 1H), 3.48 (m, 1H), 3.33 (m, 1H), 3.31 (m, 1H).

MS (ESI): 308.9 ([{$^{35}$Cl}M+H]$^+$), 310.9 ([{$^{37}$Cl}M+H]$^+$).

Example 111

(RS)-5-Fluoro-6-morpholin-2-yl-N-[5-(trifluoromethyl)-2-pyridyl]pyridin-3-amine

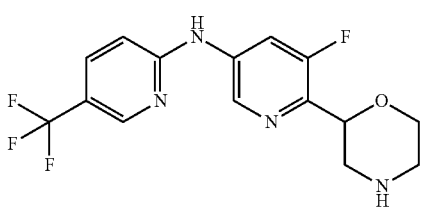 [SMILES: Fc1cc(Nc2ccc(C(F)(F)F)cn2)cnc1C1CNCCO1]

The title compound was obtained in analogy to example 110 using 2-amino-5-trifluoromethylpyridine (CAS: 74784-70-6) instead of 2-amino-5-chloropyridine in step (f). White solid.

MS (ESI): 343.0 (M+H)$^+$.

Example 112

(RS)-1-(3-Chlorophenyl)-3-(5-fluoro-6-morpholin-2-yl-3-pyridyl)urea

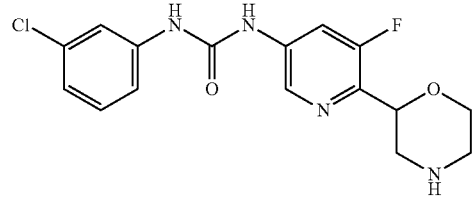 [SMILES: O=C(Nc1cccc(Cl)c1)Nc1cnc(C2CNCCO2)c(F)c1]

a) tert-Butyl 2-[5-(benzhydrylideneamino)-3-fluoro-2-pyridyl]morpholine-4-carboxylate To a solution of tert-butyl 2-(5-bromo-3-fluoro-2-pyridyl)morpholine-4-carboxylate (0.6 g, 1.66 mmol) and benzophenone imine (300 mg, 1.66 mmol, CAS: 1013-88-3) in dioxane (30 mL) were added Xantphos (4,5-bis(diphenylphosphino)-9,9-dimethylxanthene, 288 mg, 0.5 mmol, CAS: 161265-03-8), Cs₂CO₃ (1.62 g, 4.98 mmol) and tris(dibenzylideneacetone)dipalladium(0) (152 mg, 0.166 mmol, CAS: 51364-51-3) under N₂ atmosphere. The mixture was stirred at 85° C. overnight. Then the reaction mixture was filtered. The filtrate was concentrated under vacuum to give crude tert-butyl 2-[5-(benzhydrylideneamino)-3-fluoro-2-pyridyl]morpholine-4-carboxylate (766 mg, 100% yield) as a yellow oil, which was used for the next step directly.

b) tert-Butyl 2-(5-amino-3-fluoro-2-pyridyl)morpholine-4-carboxylate

To a solution of tert-butyl 2-[5-(benzhydrylideneamino)-3-fluoro-2-pyridyl]morpholine-4-carboxylate (766 mg, 1.66 mmol) in methanol (20 mL) were added sodium acetate (681 mg, 8.3 mmol) and hydroxylamine hydrochloride (173 mg, 2.5 mmol). The mixture was stirred at room temperature for 2 hours. The solution was poured into water (50 mL) and extracted with CH₂Cl₂ (100 mL×2). The combined organic layers were dried over Na₂SO₄, concentrated under vacuum, and purified through column chromatography (CH₂Cl₂/methanol=100/1~50/1 by volume) to give tert-butyl 2-(5-amino-3-fluoro-2-pyridyl)morpholine-4-carboxylate (350 mg, 71% yield) as a yellow solid.

MS (ESI): 242.0 (M-56+H)$^+$, 298.0 (M+H)$^+$.

c) (RS)-1-(3-Chlorophenyl)-3-(5-fluoro-6-morpholin-2-yl-3-pyridyl)urea

To a solution of tert-butyl 2-(5-amino-3-fluoro-2-pyridyl)morpholine-4-carboxylate (70 mg, 0.235 mmol) in dichloromethane (1 mL) were added Et₃N (48 mg, 0.47 mmol) and 3-chlorophenyl isocyana (36 mg, 0.24 mmol, CAS: 2909-38-8). The solution was stirred at room temperature overnight. The reaction solution was diluted with dichloromethane (50 mL). Then the solution was washed with brine (50 mL×2), dried over Na₂SO₄, concentrated under reduced pressure, and dried under high vacuum. The residue was dissolved in dichloromethane (1 mL) and trifluoroacetic acid (1 mL). The solution was stirred at room temperature for 2 hours. The reaction solution was concentrated under reduced pressure. The residue was purified through prep-HPLC (0.5% TFA in CH₃CN) to give (RS)-1-(3-Chlorophenyl)-3-(5-fluoro-6-morpholin-2-yl-3-pyridyl)urea (52 mg) as a white solid.

$^1$H NMR (400 MHz, Methanol-d⁴): δ 8.41 (s, 1H), 8.06 (dd, 1H), 7.67 (s, 1H), 7.29 (m, 2H), 7.05 (m, 1H), 5.13 (dd, 1H), 4.12 (m, 1H), 3.98 (m, 1H), 3.69 (m, 1H), 3.51 (dd, 1H), 3.35~3.30 (m, 2H).

MS (ESI): 351.1 ([{³⁵Cl}M+H]⁺), 353.1 ([{³⁷Cl}M+H]⁺).

Example 113

(RS)—N-(5-Fluoro-6-morpholin-2-yl-3-pyridyl)-2-(trifluoromethyl)pyridine-4-carboxamide

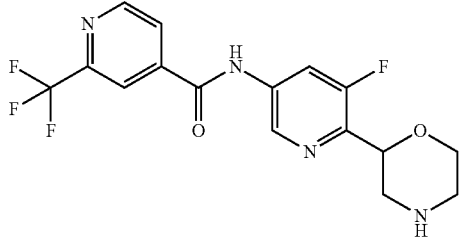 [SMILES: O=C(Nc1cnc(C2CNCCO2)c(F)c1)c1ccnc(C(F)(F)F)c1]

To a solution of 2-(trifluoromethyl)pyridine-4-carboxylic acid (57 mg, 0.30 mmol, CAS: 131747-41-6) in DMF (1 mL) were added HATU (112.2 mg, 0.295 mmol, CAS: 148893-10-1), N,N-diisopropylethylamine (104 mg, 0.804 mmol, CAS: 7087-68-5) and tert-butyl 2-(5-amino-3-fluoro-2-pyridyl)morpholine-4-carboxylate (80 mg, 0.27 mmol). The solution was stirred at room temperature overnight. The reaction mixture was diluted with dichloromethane (50 mL). The solution was then washed with water (50 mL) and brine (50 mL), dried over Na₂SO₄, concentrated under reduced pressure, and dried under high vacuum. The residue was dissolved in dichloromethane (1 mL) and trifluoroacetic acid (1 mL). The solution was stirred at room temperature for 2 hours. The reaction solution was concentrated under reduced pressure. The residue was purified through prep-HPLC (0.5% TFA in CH₃CN) to give (RS)—N-(5-fluoro-6-morpholin-2-yl-3-pyridyl)-2-(trifluoromethyl)pyridine-4-carboxamide (10 mg) as a white solid.

$^1$H NMR (400 MHz, Methanol-d⁴): δ 8.94 (d, 1H), 8.77 (d, 1H), 8.34~8.30 (m, 2H), 8.15 (d, 1H), 5.19 (dd, 1H), 4.14 (m, 1H), 4.06 (m, 1H), 3.71 (m, 1H), 3.55 (m, 1H), 3.36~3.30 (m, 2H).

MS (ESI): 393.0 (M+Na)⁺, 371.0 (M+H)⁺.

Example 114

(RS)-4-Chloro-N-(5-fluoro-6-morpholin-2-yl-3-pyridyl)-3-propyl-1H-pyrazole-5-carboxamide

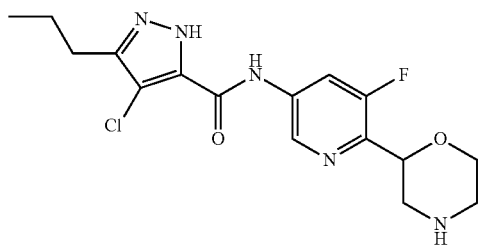 [SMILES: CCCc1n[nH]c(C(=O)Nc2cnc(C3CNCCO3)c(F)c2)c1Cl]

The title compound was obtained in analogy to example 113 using 4-chloro-5-propyl-1H-pyrazole-3-carboxylic acid (CAS: 1340578-20-2) instead of 2-(trifluoromethyl)pyridine-4-carboxylic acid. White solid. MS (ESI): 370.0 ([{³⁷Cl}M+H]⁺), 368.0 ([{³⁵Cl}M+H]⁺).

Example 115

4-Chloro-3-isopropyl-N-[6-[(2R)-morpholin-2-yl]-3-pyridyl]-1H-pyrazole-5-carboxamide

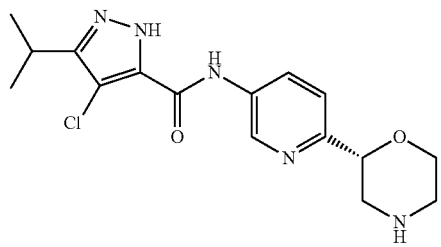 [SMILES: CC(C)c1n[nH]c(C(=O)Nc2ccc([C@H]3CNCCO3)nc2)c1Cl]

The title compound was obtained in analogy to example 66 using 4-chloro-5-propan-2-yl-2H-pyrazole-3-carboxylic acid (CAS: 1291271-55-0) instead of 3-ethyl-4-methyl-1H-pyrazole-5-carboxylic acid. White solid.

MS (ESI): 350.0 ({³⁵Cl}M+H)⁺, 352.0 ({³⁷Cl}M+H)⁺.

Example 116

4-Fluoro-3-isopropyl-N-[6-[(2R)-morpholin-2-yl]-3-pyridyl]-1H-pyrazole-5-carboxamide

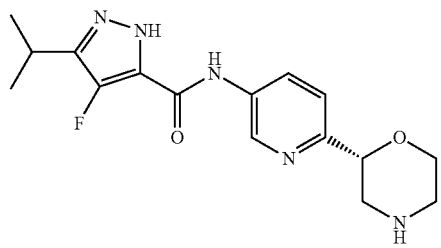 [SMILES: CC(C)c1n[nH]c(C(=O)Nc2ccc([C@H]3CNCCO3)nc2)c1F]

a) Ethyl 4-fluoro-3-isopropyl-1H-pyrazole-5-carboxylate

To a solution of ethyl 3-isopropyl-1H-pyrazole-5-carboxylate (5.0 g, 0.027 mmol, CAS: 78208-72-7) in CH₃CN (300 mL) was added Selectfluor® (12.7 g, 35.7 mmol, CAS: 140681-55-6) at 0° C. Then the solution was heated to 70° C. Stirring was continued for 15 hours. The reaction solution was cooled to room temperature and concentrated under reduced pressure. The residue was diluted with aqueous HCl (3N, 200 mL) and extracted with dichloromethane (100 mL×2). The combined organic layers were washed with brine (50 mL), dried over Na₂SO₄, and concentrated under reduced pressure. Purification through silica gel column chromatography (dichloromethane/MeOH=200/1~100/1 by volume) gave ethyl 4-fluoro-3-isopropyl-1H-pyrazole-5-carboxylate (900 mg, 17% yield) as a yellow oil.

MS (ESI): 223.1 (M+Na)⁺, 201.1 (M+H)⁺.

b) 4-Fluoro-3-isopropyl-1H-pyrazole-5-carboxylic acid

To a solution of ethyl 4-fluoro-3-isopropyl-1H-pyrazole-5-carboxylate (900 mg, 4.49 mmol) in THF/MeOH (10/10 mL) was added 1M aq NaOH (9 mL, 9 mmol) at 0° C. Then the solution was refluxed for 3 hours. The reaction solution was poured into water. The pH was adjusted to 1 with concentrated HCl. The mixture was extracted with ethyl acetate (100 mL×2). The combined organic layers were washed with brine, and concentrated under vacuum. The residue was recrystallized from ethyl acetate (10 mL) to give 4-fluoro-3-isopropyl-1H-pyrazole-5-carboxylic acid (450 mg, 58% yield) as a white solid.

$^1$H NMR (400 MHz, Methanol-d$^4$): δ 3.08 (m, 1H), 1.32 (d, 6H).
MS (ESI): 173.1 (M+H)$^+$.

c) 4-Fluoro-3-isopropyl-N-[6-[(2R)-morpholin-2-yl]-3-pyridyl]-1H-pyrazole-5-carboxamide The title compound was obtained in analogy to example 66 using 4-fluoro-3-isopropyl-1H-pyrazole-5-carboxylic acid instead of 3-ethyl-4-methyl-1H-pyrazole-5-carboxylic acid. White solid.

$^1$H NMR (400 MHz, Methanol-d$^4$): δ 8.93 (d, 1H), 8.27 (dd, 1H), 7.59 (d, 1H), 4.87 (m, 1H), 4.24 (dd, 1H), 4.01 (t, 1H), 3.67 (d, 1H), 3.34 (m, 1H), 3.30 (m, 2H), 3.11 (m, 1H), 1.35 (d, 6H).
MS (ESI): 334.1 (M+H)$^+$.

Example 117

(RS)—N-(5-Methyl-6-morpholin-2-yl-3-pyridyl)-2-(trifluoromethyl)pyridine-4-carboxamide

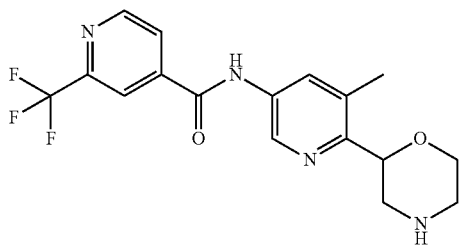 [SMILES: Cc1cc(NC(=O)c2ccnc(C(F)(F)F)c2)cnc1C1CNCCO1]

a) tert-Butyl 2-[5-(benzhydrylideneamino)-3-methyl-2-pyridyl]morpholine-4-carboxylate To a solution of tert-butyl 2-(5-bromo-3-methyl-2-pyridyl)morpholine-4-carboxylate (0.28 g, 0.78 mmol) and benzophenone imine (156 mg, 0.86 mmol, CAS: 1013-88-3) in dioxane (20 mL) were added Xantphos (4,5-bis(diphenylphosphino)-9,9-dimethylxanthene, 90 mg, 0.156 mmol, CAS: 161265-03-8), Cs$_2$CO$_3$ (0.77 g, 2.34 mmol) and tris (dibenzylideneacetone)dipalladium(0) (72 mg, 0.078 mmol, CAS: 51364-51-3) under N$_2$ atmosphere. The mixture was stirred at 90° C. for 12 hours. Then the reaction mixture was diluted with water (50 mL) and extracted with ethyl acetate (100 mL×2). The combined organic layers were washed with brine, dried over Na$_2$SO$_4$, and concentrated under reduced pressure. Further drying under high vacuum gave tert-butyl 2-[5-(benzhydrylideneamino)-3-methyl-2-pyridyl]morpholine-4-carboxylate (360 mg) as a yellow oil, which was used for the next step directly.

b) tert-Butyl 2-(5-amino-3-methyl-2-pyridyl)morpholine-4-carboxylate

To a solution of tert-butyl 2-[5-(benzhydrylideneamino)-3-methyl-2-pyridyl]morpholine-4-carboxylate (360 mg, 0.78 mmol) in methanol (10 mL) were added sodium acetate (250 mg, 2.34 mmol) and hydroxylamine hydrochloride (82 mg, 1.17 mmol). The mixture was stirred at room temperature for 3 hours. The solution was poured into water (50 mL) and extracted with CH$_2$Cl$_2$ (100 mL×2). The combined organic layers were dried over Na$_2$SO$_4$, concentrated under vacuum, and purified through column chromatography (CH$_2$Cl$_2$/methanol=100/1~50/1 by volume) to give tert-butyl 2-(5-amino-3-methyl-2-pyridyl)morpholine-4-carboxylate (150 mg, 65% yield) as an off-white solid.

c) (RS)—N-(5-Methyl-6-morpholin-2-yl-3-pyridyl)-2-(trifluoromethyl)pyridine-4-carboxamide To a solution of 2-(trifluoromethyl)pyridine-4-carboxylic acid (29 mg, 0.15 mmol, CAS: 131747-41-6) in DMF (1 mL) were added HATU (56 mg, 0.15 mmol, CAS: 148893-10-1), N,N-diisopropylethylamine (52 mg, 0.40 mmol, CAS: 7087-68-5) and tert-butyl 2-(5-amino-3-methyl-2-pyridyl)morpholine-4-carboxylate (40 mg, 0.14 mmol). The solution was stirred at room temperature overnight. The reaction solution was diluted with dichloromethane (50 mL). The solution was then washed with water (50 mL) and brine (50 mL), dried over Na$_2$SO$_4$, concentrated under reduced pressure, and dried under high vacuum. The residue was dissolved in dichloromethane (1 mL) and trifluoroacetic acid (1 mL). The solution was stirred at room temperature for 2 hours. The reaction solution was concentrated under reduced pressure. The residue was purified through prep-HPLC (0.5% TFA in CH$_3$CN) to give (RS)—N-(5-methyl-6-morpholin-2-yl-3-pyridyl)-2-(trifluoromethyl)pyridine-4-carboxamide (4 mg) as a white solid.

$^1$H NMR (400 MHz, Methanol-d$^4$): δ 8.95 (d, 1H), 8.85 (d, 1H), 8.34 (s, 1H), 8.15 (dd, 1H), 5.13 (dd, 1H), 4.04 (m, 2H), 3.77 (m, 1H), 3.61 (dd, 1H), 3.38~3.30 (m, 2H), 2.49 (s, 3H).
MS (ESI): 367.1 (M+H)$^+$.

Example 118

(RS)-4-Chloro-N-(5-methyl-6-morpholin-2-yl-3-pyridyl)-3-propyl-1H-pyrazole-5-carboxamide

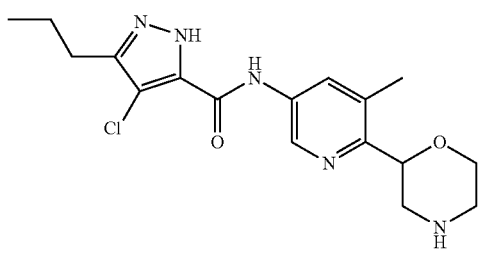 [SMILES: CCCc1n[nH]c(C(=O)Nc2cnc(C3CNCCO3)c(C)c2)c1Cl]

The title compound was obtained in analogy to example 117 using 4-chloro-5-propyl-1H-pyrazole-3-carboxylic acid (CAS: 1340578-20-2) instead of 2-(trifluoromethyl)pyridine-4-carboxylic acid. White solid. MS (ESI): 366.0 ([{$^{37}$Cl}M+H]$^+$), 364.0 ([{$^{35}$Cl}M+H]$^+$).

Example 119

(RS)-1-(3-Chlorophenyl)-3-(5-methyl-6-morpholin-2-yl-3-pyridyl)urea

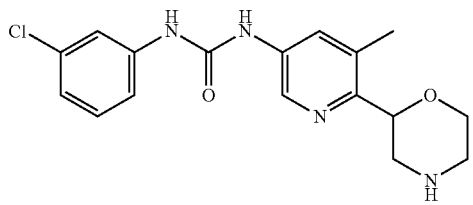 [SMILES: Cc1cc(NC(=O)Nc2cccc(Cl)c2)cnc1C1CNCCO1]

To a solution of tert-butyl 2-(5-amino-3-methyl-2-pyridyl)morpholine-4-carboxylate (30 mg, 0.1 mmol) in dichloromethane (1 mL) were added Et$_3$N (30 mg, 0.3 mmol) and 3-chlorophenyl isocyanate (16 mg, 0.1 mmol, CAS: 2909-38-8). The solution was stirred at room temperature overnight. The reaction solution was diluted with dichloromethane (50 mL). Then the solution was washed with brine (50 mL×2), dried over Na$_2$SO$_4$, concentrated under reduced pressure, and dried under high vacuum. The residue was dissolved in dichloromethane (1 mL) and trifluoroacetic acid (1 mL). The solution was stirred at room temperature for 2 hours. The reaction solution was concentrated under reduced pressure. The residue was purified through prep-HPLC (0.5% TFA in CH$_3$CN) to give (RS)-1-(3-chlorophenyl)-3-(5-methyl-6-morpholin-2-yl-3-pyridyl)urea (32 mg) as a white solid.

$^1$H NMR (400 MHz, DMSO-d$^6$): δ 9.36 (d, 2H), 9.04 (m, 1H), 8.47 (s, 1H), 7.84 (d, 1H), 7.73 (s, 1H), 7.32 (m, 2H), 7.05 (m, 1H), 4.91 (dd, 1H), 4.00 (m, 1H), 3.89 (m, 1H), 3.58 (m, 2H), 3.27 (d, 1H), 3.15 (m, 1H), 2.35 (s, 3H).

MS (ESI): 347.0 ([{$^{35}$Cl}M+H]$^+$), 349.0 ([{$^{37}$Cl}M+H]$^+$).

Example 120

4-Chloro-3-isopropyl-N-[6-[(2S)-morpholin-2-yl]-3-pyridyl]-1H-pyrazole-5-carboxamide

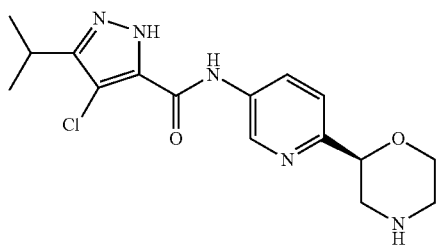 [SMILES: CC(C)c1n[nH]c(C(=O)Nc2ccc([C@@H]3CNCCO3)nc2)c1Cl]

The title compound was obtained in analogy to example 67 using 4-chloro-5-propan-2-yl-2H-pyrazole-3-carboxylic acid (CAS: 1291271-55-0) instead of 3-ethyl-4-methyl-1H-pyrazole-5-carboxylic acid. White solid.

MS (ESI): 350.1 ({$^{35}$Cl}M+H)$^+$, 352.1 ({$^{37}$Cl}M+H)$^+$.

Example 121

4-Fluoro-3-isopropyl-N-[6-[(2S)-morpholin-2-yl]-3-pyridyl]-1H-pyrazole-5-carboxamide

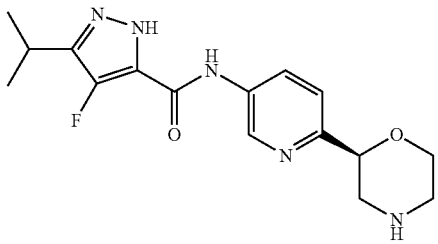 [SMILES: CC(C)c1n[nH]c(C(=O)Nc2ccc([C@@H]3CNCCO3)nc2)c1F]

The title compound was obtained in analogy to example 67 using 4-fluoro-3-isopropyl-1H-pyrazole-5-carboxylic acid instead of 3-ethyl-4-methyl-1H-pyrazole-5-carboxylic acid. White solid.

MS (ESI): 334.2 (M+H)$^+$.

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the tests given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Radioligand Binding Assay on Rat TAAR1

Membrane Preparation and Radioligand Binding.

HEK-293 cells stably expressing rat TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated $K_d$ value, that was usually around 2.3 nM, resulting in the binding of approximately 0.2% of the radioligand and a specific binding representing approximately 85% of the total binding. Nonspecific binding was defined as the amount of $^3$[H]—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 □µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]—(S)-4-[(ethyl-phenyl-amino)-methyl]-4,5-dihydro-oxazol-2-ylamine at a concentration of $3.3 \times K_d$ in nM and 500 µl of the membranes (re-suspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated $K_d$ value, that was usually around 0.7 nM, resulting in the binding of approximately 0.5% of the radioligand and a specific binding representing approximately 70% of the total binding. Nonspecific binding was defined as the amount of $^3$[H]—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]—(S)-4-[(ethyl-phenyl-amino)-methyl]-4,5-dihydro-oxazol-2-ylamine at a concentration of $3.3 \times K_d$ in nM and 500 µl of the membranes (resuspended at 60 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

The compounds show a $K_i$ value (µM) in mouse or rat on TAAR1 (in µM) as shown in the table below.

| Example | $K_i$ (µM) mouse/rat |
|---|---|
| 1 | 0.0017/0.071 |
| 2 | 0.0018/0.0437 |
| 3 | 0.0048/0.3735 |
| 4 | 0.0034/0.0794 |
| 5 | 0.0065/0.3721 |
| 6 | 0.0033/0.0159 |
| 7 | 0.0038/0.0745 |
| 8 | 0.0021/0.0047 |
| 9 | 0.0071/0.0106 |
| 10 | 0.0042/0.0029 |
| 11 | 0.0038/0.0047 |
| 12 | 0.0051/0.0889 |
| 13 | 0.0124/0.3284 |
| 14 | 0.0084/0.917 |
| 15 | 0.0056/0.0189 |
| 16 | 0.0185/0.1452 |
| 17 | 0.0382/0.466 |
| 18 | 0.0015/0.043 |
| 19 | 0.0027/0.0032 |

| Example | $K_i$ (μM) mouse/rat |
|---|---|
| 20 | 0.0019/0.0751 |
| 21 | 0.002/0.0324 |
| 22 | 0.0126/0.2466 |
| 23 | 0.0124/0.1541 |
| 24 | 0.0124/0.182 |
| 25 | 0.0048/0.0254 |
| 26 | 0.0118/0.4241 |
| 27 | 0.074/1.0981 |
| 28 | 0.1096/0.6061 |
| 29 | 0.0035/0.0103 |
| 30 | 0.0034/0.0208 |
| 31 | 0.003/0.1019 |
| 32 | 0.0028/0.0338 |
| 33 | 0.0056/0.052 |
| 34 | 0.0427/0.147 |
| 35 | 0.0056/0.0107 |
| 36 | 0.0066/0.0278 |
| 37 | 0.1388/1.4667 |
| 38 | 0.0263/0.0727 |
| 39 | 0.007/0.0146 |
| 40 | 0.0089/0.0428 |
| 41 | 0.0016/0.005 |
| 42 | 0.0038/0.003 |
| 43 | 0.0474/0.0838 |
| 44 | 0.0239/0.4425 |
| 45 | 0.162/1.1255 |
| 46 | 0.0188/0.651 |
| 47 | 0.0039/0.1645 |
| 48 | 0.0199/1.3742 |
| 49 | 0.0052/0.066 |
| 50 | 0.005/0.1224 |
| 51 | 0.0039/0.2117 |
| 52 | 0.0045/0.0922 |
| 53 | 0.0061/0.0718 |
| 54 | 0.0329/0.2833 |
| 55 | 0.0064/0.0221 |
| 56 | 0.0075/0.0334 |
| 57 | 0.673/2.3954 |
| 58 | 0.0373/0.6848 |
| 59 | 0.0063/0.021 |
| 60 | 0.0096/0.0448 |
| 61 | 0.0035/0.0132 |
| 62 | 0.0035/0.0077 |
| 63 | 0.0495/0.0613 |
| 64 | 0.018/1.5684 |
| 65 | 0.3444/4.4706 |
| 66 | 0.0113/0.0534 |
| 67 | 0.0147/0.2704 |
| 68 | 0.0731/0.0469 |
| 69 | 0.0762/0.0512 |
| 70 | 0.0186/1.4541 |
| 71 | 0.0072/0.1948 |
| 72 | 0.0058/4.9282 |
| 73 | 0.0059/1.9634 |
| 74 | 0.0041/0.066 |
| 75 | 0.0048/0.0133 |
| 76 | 0.0063/0.0384 |
| 77 | 0.0121/0.302 |
| 78 | 0.0056/0.041 |
| 79 | 0.0074/0.0568 |
| 80 | 0.0065/0.0856 |
| 81 | 0.006/0.0152 |
| 82 | 0.0039/0.0925 |
| 83 | 0.0083/0.7565 |
| 84 | 0.0063/0.0685 |
| 85 | 0.0046/0.1504 |
| 86 | 0.0074/0.1556 |
| 87 | 0.0053/0.0291 |
| 88 | 0.0113/0.011 |
| 89 | 0.0133/0.0297 |
| 90 | 0.0038/0.0269 |
| 91 | 0.0031/0.0061 |
| 92 | 0.2624/0.0597 |
| 93 | 0.0215/0.0023 |
| 94 | 0.0216/0.1069 |
| 95 | 0.0113/0.0534 |

-continued

| Example | $K_i$ (μM) mouse/rat |
|---|---|
| 96 | 0.0035/ 0.0554 |
| 97 | 0.0043/ 0.0387 |
| 98 | 0.24/ 0.0442 |
| 99 | 0.0242/ 0.0041 |
| 100 | 0.0158/ 0.1233 |
| 101 | 0.0094/ 0.0225 |
| 102 | 0.1785/ 0.4612 |
| 103 | 0.0677/ 0.1224 |
| 104 | 0.0837/ 0.4546 |
| 105 | 0.0054/ 0.0176 |
| 106 | 0.0085/ 0.1366 |
| 107 | 0.1432/ 0.3706 |
| 108 | 0.0241/ 0.0321 |
| 109 | 0.0543/ 0.019 |
| 110 | 0.0245/ 1.0957 |
| 111 | 0.0128/ 0.1757 |
| 112 | 0.0102/ 0.0286 |
| 113 | 0.0557/ 1.3143 |
| 114 | 0.0048/ 0.0221 |
| 115 | 0.0087/ 0.009 |
| 116 | 0.015/ 0.1203 |
| 117 | 0.464/ 1.4065 |
| 118 | 0.0468/ 0.597 |
| 119 | 0.0533/ 0.2431 |
| 120 | 0.0311/ 0.0203 |
| 121 | 0.0239/ 0.0954 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |

-continued

Capsule Formulation

| Item | Ingredients | mg/capsule | | | |
|---|---|---|---|---|---|
| | | 5 mg | 25 mg | 100 mg | 500 mg |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

We claim:
1. A compound of formula

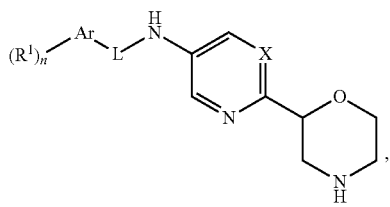

wherein
X is CR;
R is hydrogen, halogen or lower alkyl;
L is a bond, —C(O)— or —C(O)NH—;
Ar is phenyl or a five or six membered heteroaryl group, containing one or two N atoms;
R¹ is halogen, lower alkyl, lower alkyl substituted by halogen, lower alkoxy, lower alkoxy substituted by halogen or cycloalkyl;
n is 0, 1, 2 or 3;
or, a pharmaceutically suitable acid addition salt thereof, a racemic mixture, an enantiomer or mixture thereof.

2. The compound of formula I according to claim 1, wherein "L" is a bond.

3. The compound of formula I according to claim 2, wherein the compound is:
(RS)—N-(4-Chlorophenyl)-6-morpholin-2-yl-pyridin-3-amine;
(RS)—N-(4-Bromophenyl)-6-morpholin-2-yl-pyridin-3-amine;
(RS)—N-(4-Ethoxyphenyl)-6-morpholin-2-yl-pyridin-3-amine;
(RS)—N-(3-Chlorophenyl)-6-morpholin-2-yl-pyridin-3-amine;
(RS)—N-(4-Fluorophenyl)-6-morpholin-2-yl-pyridin-3-amine;
(RS)-6-Morpholin-2-yl-N-[4-(trifluoromethyl)phenyl]pyridin-3-amine;
(RS)—N-(6-Morpholin-2-yl-3-pyridyl)-2-(trifluoromethyl)pyrimidin-4-amine;
N-(4-Chlorophenyl)-6-[(2S)-morpholin-2-yl]pyridin-3-amine;
6-[(2S)-Morpholin-2-yl]-N-[4-(trifluoromethyl)phenyl]pyridin-3-amine;
N-(5-Chloro-2-pyridyl)-6-[(2S)-morpholin-2-yl]pyridin-3-amine;
N-(5-Bromo-2-pyridyl)-6-[(2S)-morpholin-2-yl]pyridin-3-amine;
6-[(2S)-Morpholin-2-yl]-N-[6-(trifluoromethyl)-3-pyridyl]pyridin-3-amine;
6-[(2S)-Morpholin-2-yl]-N-[4-(trifluoromethyl)-2-pyridyl]pyridin-3-amine;
N-(4-Chlorophenyl)-6-[(2R)-morpholin-2-yl]pyridin-3-amine;
6-[(2R)-Morpholin-2-yl]-N-[4-(trifluoromethyl)phenyl]pyridin-3-amine;
N-(5-Chloro-2-pyridyl)-6-[(2R)-morpholin-2-yl]pyridin-3-amine;
6-[(2R)-Morpholin-2-yl]-N-[6-(trifluoromethyl)-3-pyridyl]pyridin-3-amine;
6-[(2R)-Morpholin-2-yl]-N-[4-(trifluoromethyl)-2-pyridyl]pyridin-3-amine;
N-[6-[(2S)-Morpholin-2-yl]-3-pyridyl]-5-(trifluoromethyl)pyridin-2-amine;
N-[6-[(2S)-Morpholin-2-yl]-3-pyridyl]-6-(trifluoromethyl)pyridin-2-amine;
N-(5-Bromo-2-pyridyl)-6-[(2R)-morpholin-2-yl]pyridin-3-amine;
N-[6-[(2R)-Morpholin-2-yl]-3-pyridyl]-5-(trifluoromethyl)pyridin-2-amine;
N-[6-[(2R)-Morpholin-2-yl]-3-pyridyl]-6-(trifluoromethyl)pyridin-2-amine;
(RS)-5-Chloro-N-(5-chloro-2-pyridyl)-6-morpholin-2-yl-pyridin-3-amine;
(RS)-5-Chloro-6-morpholin-2-yl-N-[5-(trifluoromethyl)-2-pyridyl]pyridin-3-amine;
(RS)-5-Methyl-6-morpholin-2-yl-N-[5-(trifluoromethyl)-2-pyridyl]pyridin-3-amine;
(RS)—N-(5-Chloro-2-pyridyl)-5-fluoro-6-morpholin-2-yl-pyridin-3-amine; or,
(RS)-5-Fluoro-6-morpholin-2-yl-N-[5-(trifluoromethyl)-2-pyridyl]pyridin-3-amine.

4. The compound of formula I according to claim 1, wherein L is —C(O)—.

5. The compound of formula I according to claim 4, wherein the compound is:
(RS)-4-Chloro-N-(6-morpholin-2-yl-3-pyridyl)benzamide;
(RS)-3-Chloro-N-(6-morpholin-2-yl-3-pyridyl)benzamide;
(RS)-4-Ethoxy-N-(6-morpholin-2-yl-3-pyridyl)benzamide;
(RS)-4-Fluoro-N-(6-morpholin-2-yl-3-pyridyl)benzamide;
(RS)-4-Chloro-N-(6-morpholin-2-yl-3-pyridyl)-3-propyl-1H-pyrazole-5-carboxamide;
(RS)—N-(6-Morpholin-2-yl-3-pyridyl)-2-(trifluoromethyl)pyridine-4-carboxamide;
4-Chloro-N-[6-[(2S)-morpholin-2-yl]-3-pyridyl]benzamide;
3-Chloro-N-[6-[(2S)-morpholin-2-yl]-3-pyridyl]benzamide;
N-[6-[(2S)-Morpholin-2-yl]-3-pyridyl]-4-(trifluoromethyl)benzamide;
N-[6-[(2S)-Morpholin-2-yl]-3-pyridyl]-2-(trifluoromethyl)pyridine-4-carboxamide;
N-[6-[(2S)-Morpholin-2-yl]-3-pyridyl]-3-(trifluoromethyl)benzamide;
N-[6-[(2S)-Morpholin-2-yl]-3-pyridyl]-6-(2,2,2-trifluoroethoxy)pyridine-3-carboxamide;
2-Ethyl-N-[6-[(2S)-morpholin-2-yl]-3-pyridyl]pyrimidine-5-carboxamide;

3-Isopropyl-N-[6-[(2S)-morpholin-2-yl]-3-pyridyl]-1H-pyrazole-5-carboxamide;
4-Chloro-N-[6-[(2S)-morpholin-2-yl]-3-pyridyl]-3-propyl-1H-pyrazole-5-carboxamide;
4-Chloro-3-cyclopropyl-N-[6-[(2S)-morpholin-2-yl]-3-pyridyl]-1H-pyrazole-5-carboxamide;
4-Chloro-N-[6-[(2S)-morpholin-2-yl]-3-pyridyl]-3-(trifluoromethyl)-1H-pyrazole-5-carboxamide;
4-Chloro-3-methyl-N-[6-[(2S)-morpholin-2-yl]-3-pyridyl]-1H-pyrazole-5-carboxamide;
4-Methyl-N-[6-[(2S)-morpholin-2-yl]-3-pyridyl]-1H-pyrazole-5-carboxamide;
4-Chloro-1-methyl-N-[6-[(2S)-morpholin-2-yl]-3-pyridyl]-5-propyl-pyrazole-3-carboxamide;
4-Chloro-1-methyl-N-[6-[(2R)-morpholin-2-yl]-3-pyridyl]-5-propyl-pyrazole-3-carboxamide;
4-Chloro-N-[6-[(2R)-morpholin-2-yl]-3-pyridyl]benzamide;
3-Chloro-N-[6-[(2R)-morpholin-2-yl]-3-pyridyl]benzamide;
N-[6-[(2R)-Morpholin-2-yl]-3-pyridyl]-4-(trifluoromethyl)benzamide;
N-[6-[(2R)-Morpholin-2-yl]-3-pyridyl]-2-(trifluoromethyl)pyridine-4-carboxamide;
N-[6-[(2R)-Morpholin-2-yl]-3-pyridyl]-3-(trifluoromethyl)benzamide;
N-[6-[(2R)-Morpholin-2-yl]-3-pyridyl]-6-(2,2,2-trifluoroethoxy)pyridine-3-carboxamide;
2-Ethyl-N-[6-[(2R)-morpholin-2-yl]-3-pyridyl]pyrimidine-5-carboxamide;
3-Isopropyl-N-[6-[(2R)-morpholin-2-yl]-3-pyridyl]-1H-pyrazole-5-carboxamide;
4-Chloro-N-[6-[(2R)-morpholin-2-yl]-3-pyridyl]-3-propyl-1H-pyrazole-5-carboxamide;
4-Chloro-3-cyclopropyl-N-[6-[(2R)-morpholin-2-yl]-3-pyridyl]-1H-pyrazole-5-carboxamide;
4-Chloro-N-[6-[(2R)-morpholin-2-yl]-3-pyridyl]-3-(trifluoromethyl)-1H-pyrazole-5-carboxamide;
4-Chloro-3-methyl-N-[6-[(2R)-morpholin-2-yl]-3-pyridyl]-1H-pyrazole-5-carboxamide;
4-Methyl-N-[6-[(2R)-morpholin-2-yl]-3-pyridyl]-1H-pyrazole-5-carboxamide;
(R)-3-Ethyl-4-methyl-N-(6-(morpholin-2-yl)pyridin-3-yl)-1H-pyrazole-5-carboxamide;
(S)-3-Ethyl-4-methyl-N-(6-(morpholin-2-yl)pyridin-3-yl)-1H-pyrazole-5-carboxamide;
(R)-6-Methyl-N-(6-(morpholin-2-yl)pyridin-3-yl)-2-(trifluoromethyl)pyrimidine-4-carboxamide;
(S)-6-Methyl-N-(6-(morpholin-2-yl)pyridin-3-yl)-2-(trifluoromethyl)pyrimidine-4-carboxamide;
(RS)-4-Chloro-3-ethoxy-N-(6-morpholin-2-yl-3-pyridyl)-1H-pyrazole-5-carboxamide;
(RS)-4-Chloro-N-(6-morpholin-2-yl-3-pyridyl)-3-(2,2,2-trifluoroethoxy)-1H-pyrazole-5-carboxamide;
4-Chloro-3-ethyl-N-[6-[(2S)-morpholin-2-yl]-3-pyridyl]-1H-pyrazole-5-carboxamide;
3-Ethyl-4-fluoro-N-[6-[(2S)-morpholin-2-yl]-3-pyridyl]-1H-pyrazole-5-carboxamide;
4-Bromo-3-ethyl-N-[6-[(2S)-morpholin-2-yl]-3-pyridyl]-1H-pyrazole-5-carboxamide;
4-Fluoro-N-[6-[(2S)-morpholin-2-yl]-3-pyridyl]-3-propyl-1H-pyrazole-5-carboxamide;
3-Cyclopropyl-4-fluoro-N-[6-[(2S)-morpholin-2-yl]-3-pyridyl]-1H-pyrazole-5-carboxamide;
4-Bromo-3-cyclopropyl-N-[6-[(2S)-morpholin-2-yl]-3-pyridyl]-1H-pyrazole-5-carboxamide;
4-Chloro-3-ethyl-N-[6-[(2R)-morpholin-2-yl]-3-pyridyl]-1H-pyrazole-5-carboxamide;
3-Ethyl-4-fluoro-N-[6-[(2R)-morpholin-2-yl]-3-pyridyl]-1H-pyrazole-5-carboxamide;
4-Bromo-3-ethyl-N-[6-[(2R)-morpholin-2-yl]-3-pyridyl]-1H-pyrazole-5-carboxamide;
4-Fluoro-N-[6-[(2R)-morpholin-2-yl]-3-pyridyl]-3-propyl-1H-pyrazole-5-carboxamide;
3-Cyclopropyl-4-fluoro-N-[6-[(2R)-morpholin-2-yl]-3-pyridyl]-1H-pyrazole-5-carboxamide;
4-Bromo-3-cyclopropyl-N-[6-[(2R)-morpholin-2-yl]-3-pyridyl]-1H-pyrazole-5-carboxamide;
3-Isobutyl-N-[6-[(2S)-morpholin-2-yl]-3-pyridyl]-1H-pyrazole-5-carboxamide;
4-Fluoro-3-isobutyl-N-[6-[(2S)-morpholin-2-yl]-3-pyridyl]-1H-pyrazole-5-carboxamide;
3-Butyl-4-fluoro-N-[6-[(2S)-morpholin-2-yl]-3-pyridyl]-1H-pyrazole-5-carboxamide;
3-Butyl-N-[6-[(2S)-morpholin-2-yl]-3-pyridyl]-1H-pyrazole-5-carboxamide;
5-Isopropyl-N-[6-[(2S)-morpholin-2-yl]-3-pyridyl]-2-(2,2,2-trifluoroethyl)pyrazole-3-carboxamide;
2-Isopropyl-N-[6-[(2S)-morpholin-2-yl]-3-pyridyl]-5-(2,2,2-trifluoroethoxy)pyrazole-3-carboxamide;
3-Isobutyl-N-[6-[(2R)-morpholin-2-yl]-3-pyridyl]-1H-pyrazole-5-carboxamide;
4-Fluoro-3-isobutyl-N-[6-[(2R)-morpholin-2-yl]-3-pyridyl]-1H-pyrazole-5-carboxamide;
3-Butyl-4-fluoro-N-[6-[(2R)-morpholin-2-yl]-3-pyridyl]-1H-pyrazole-5-carboxamide;
3-Butyl-N-[6-[(2R)-morpholin-2-yl]-3-pyridyl]-1H-pyrazole-5-carboxamide;
5-Isopropyl-N-[6-[(2R)-morpholin-2-yl]-3-pyridyl]-2-(2,2,2-trifluoroethyl)pyrazole-3-carboxamide;
2-Isopropyl-N-[6-[(2R)-morpholin-2-yl]-3-pyridyl]-5-(2,2,2-trifluoroethoxy)pyrazole-3-carboxamide;
4-Chloro-3-ethoxy-N-[6-[(2R)-morpholin-2-yl]-3-pyridyl]-1H-pyrazole-5-carboxamide;
4-Chloro-N-[6-[(2S)-morpholin-2-yl]-3-pyridyl]-3-(2,2,2-trifluoroethoxy)-1H-pyrazole-5-carboxamide;
4-Chloro-3-ethoxy-N-[6-[(2S)-morpholin-2-yl]-3-pyridyl]-1H-pyrazole-5-carboxamide;
(RS)—N-(5-Chloro-6-morpholin-2-yl-3-pyridyl)-2-(trifluoromethyl)pyridine-4-carboxamide;
(RS)-4-Chloro-N-(5-chloro-6-morpholin-2-yl-3-pyridyl)-3-propyl-1H-pyrazole-5-carboxamide;
(RS)—N-(5-Fluoro-6-morpholin-2-yl-3-pyridyl)-2-(trifluoromethyl)pyridine-4-carboxamide;
(RS)-4-Chloro-N-(5-fluoro-6-morpholin-2-yl-3-pyridyl)-3-propyl-1H-pyrazole-5-carboxamide;
4-Chloro-3-isopropyl-N-[6-[(2R)-morpholin-2-yl]-3-pyridyl]-1H-pyrazole-5-carboxamide;
4-Fluoro-3-isopropyl-N-[6-[(2R)-morpholin-2-yl]-3-pyridyl]-1H-pyrazole-5-carboxamide;
(RS)—N-(5-Methyl-6-morpholin-2-yl-3-pyridyl)-2-(trifluoromethyl)pyridine-4-carboxamide;
(RS)-4-Chloro-N-(5-methyl-6-morpholin-2-yl-3-pyridyl)-3-propyl-1H-pyrazole-5-carboxamide;
4-Chloro-3-isopropyl-N-[6-[(2S)-morpholin-2-yl]-3-pyridyl]-1H-pyrazole-5-carboxamide; or,
4-Fluoro-3-isopropyl-N-[6-[(2S)-morpholin-2-yl]-3-pyridyl]-1H-pyrazole-5-carboxamide.

6. The compound of formula I according to claim 1, wherein L is —C(O)NH—.

7. The compound of formula I according to claim 6, wherein the compounds is:

(RS)-1-(3-Chlorophenyl)-3-(6-morpholin-2-yl-3-pyridyl)
urea;

(RS)-1-(4-Fluorophenyl)-3-(6-morpholin-2-yl-3-pyridyl)
urea;

(RS)-1-(6-Morpholin-2-yl-3-pyridyl)-3-[4-(trifluoromethyl)phenyl]urea;

(RS)-1-(4-Chlorophenyl)-3-(6-morpholin-2-yl-3-pyridyl)
urea;

1-(3-Chlorophenyl)-3-[6-[(2S)-morpholin-2-yl]-3-pyridyl]urea;

1-[6-[(2S)-Morpholin-2-yl]-3-pyridyl]-3-[3-(trifluoromethyl)phenyl]urea;

1-(3-Chlorophenyl)-3-[6-[(2R)-morpholin-2-yl]-3-pyridyl]urea;

1-[6-[(2R)-Morpholin-2-yl]-3-pyridyl]-3-[3-(trifluoromethyl)phenyl]urea;

(RS)-1-(5-Chloro-6-morpholin-2-yl-3-pyridyl)-3-(3-chlorophenyl)urea;

(RS)-1-(3-Chlorophenyl)-3-(5-fluoro-6-morpholin-2-yl-3-pyridyl)urea; or, (RS)-1-(3-Chlorophenyl)-3-(5-methyl-6-morpholin-2-yl-3-pyridyl)urea.

8. A process for the manufacture of a compound of formula I in claim 1 which process comprises:

a) reacting a compound of formula 14 wherein X is CR with a carboxylic acid of formula 15-a to afford a compound of formula 16-a and;

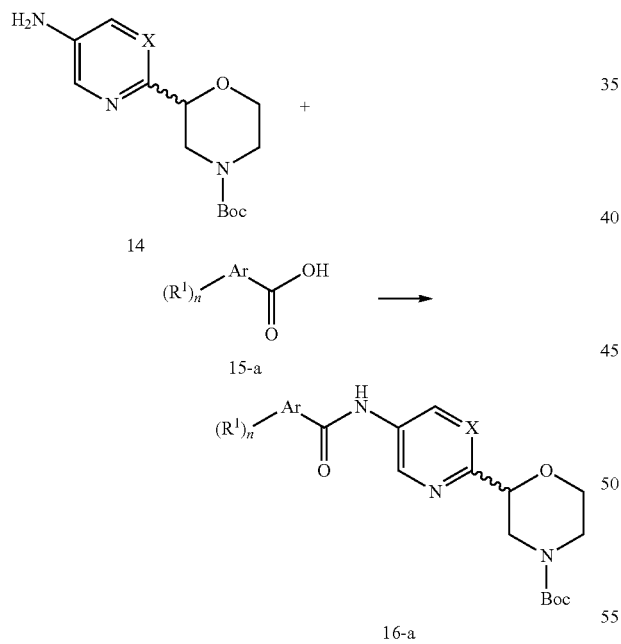

b) deprotecting the Boc group to afford a compound of claim 1 wherein L is —(CO)— and optionally converting 16-a to a pharmaceutically acceptable acid addition salt.

9. A process for the manufacture of a compound of formula I in claim 1 which process comprises:

a) reacting a compound of formula 14 wherein X is CR with a isocyanate of formula 15-b to afford a compound of formula 16-a and;

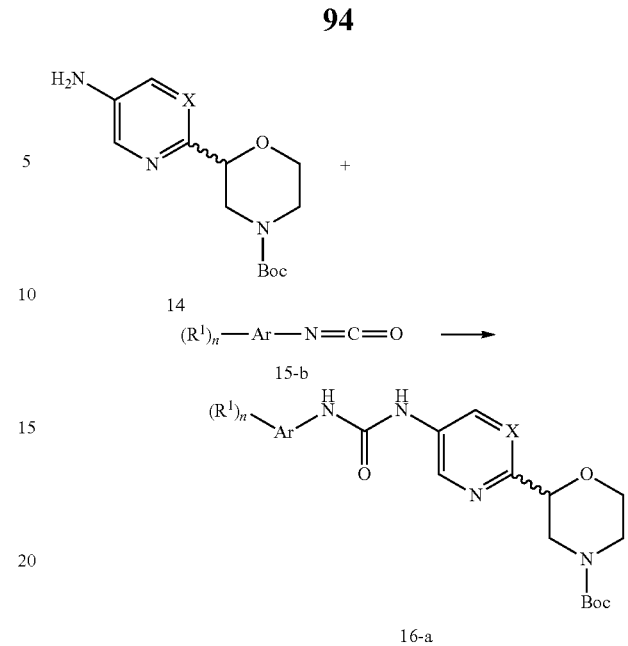

b) deprotecting the Boc group to afford a compound of claim 1 wherein L is —NHC(O)— and optionally converting 16-a to a pharmaceutically acceptable acid addition salt.

10. A process for the manufacture of a compound of formula I in claim 1 which process comprises:

a) reacting a compound of formula 8 wherein X is CR, or an enantiomer thereof, with a amine of formula 11 to afford a compound of formula 12 and;

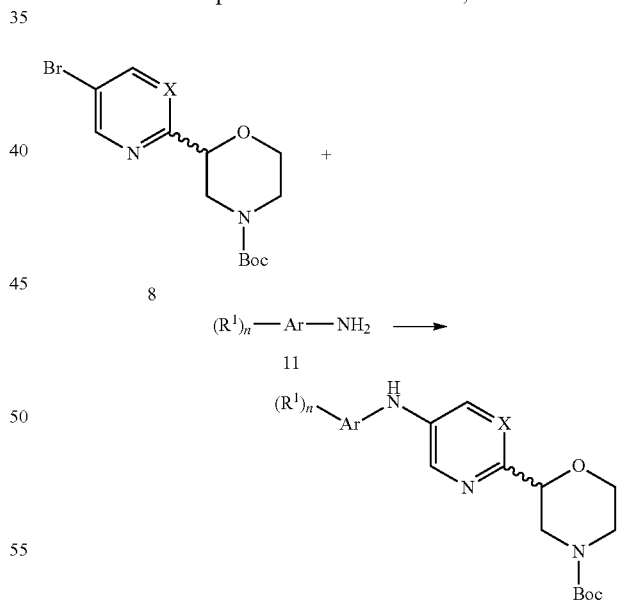

b) deprotecting the Boc group to afford a compound of claim 1 wherein L is a bond and optionally converting 12, or an enantiomer thereof, to a pharmaceutically acceptable acid addition salt.

11. A pharmaceutical composition comprising a compound of claim 1 and a pharmaceutical acceptable carrier and/or adjuvant.

12. A method of treating a disease associated with trace amine associated receptors selected from the group consisting of depression, anxiety disorders, bipolar disorder, attention deficit hyperactivity disorder (ADHD), stress-related disorders, psychotic disorders, schizophrenia, neurological diseases, Parkinson's disease, neurodegenerative disorders, Alzheimer's disease, epilepsy, migraine, hypertension, substance abuse, metabolic disorders, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders, comprising administering a therapeutically effective amount of a compound according to claim 1 to a patient in need thereof.

* * * * *